US006586583B1

(12) United States Patent
Vierling, Jr.

(10) Patent No.: US 6,586,583 B1
(45) Date of Patent: Jul. 1, 2003

(54) SOYBEAN PEROXIDASE GENE FAMILY AND AN ASSAY FOR DETECTING SOYBEAN PEROXIDASE ACTIVITY

(75) Inventor: Richard A. Vierling, Jr., Lafayette, IN (US)

(73) Assignee: Indiana Crop Improvement Association, Lafayette, IN (US)

(*) Notice: Subject to any disclaimer, the term of this patent is extended or adjusted under 35 U.S.C. 154(b) by 0 days.

(21) Appl. No.: 09/207,914

(22) Filed: Dec. 9, 1998

Related U.S. Application Data

(63) Continuation-in-part of application No. 08/868,577, filed on Jun. 4, 1997, now Pat. No. 5,866,695, which is a continuation-in-part of application No. 08/671,320, filed on Oct. 27, 1995, now Pat. No. 5,840,558.

(51) Int. Cl.$^7$ .............................................. C07H 21/04
(52) U.S. Cl. ..................... 536/24.1; 536/23.1; 435/320.1
(58) Field of Search ............................... 536/24.1, 23.1; 435/320.1

(56) References Cited

U.S. PATENT DOCUMENTS

| 5,112,752 A | | 5/1992 | Johnson et al. ............. 435/192 |
|---|---|---|---|
| 5,447,858 A | * | 9/1995 | Key et al. ................. 435/172.3 |
| 5,773,692 A | * | 6/1998 | Johnson-Flanagan et al. .... 800/205 |

FOREIGN PATENT DOCUMENTS

| CA | 2211018 | * | 3/1998 |
|---|---|---|---|
| WO | WO 97/15656 | | 5/1997 |
| WO | WO 98/55629 | | 12/1998 |

OTHER PUBLICATIONS

Tebbutt et al. Sexual Plant Reproduction (1995) vol. 8, No. 4, pp. 242–246.*
Dalton, David A., et al., "Isolation and Characterization of the Gene for Soybean Cytosolic Ascorbate Peroxidase," *Plant Physiology*, 105 (1 Suppl.): 152 (1994).

Eckes, Peter, et al., "Overproduction of alfalfa glutamine synthetase in transgenic tobacco plants," *Mol. Gen. Genet.*, 217:263–268 (1989).

Gijzen, Mark, "A deletion mutation at the *ep* locus causes low seed coat peroxidase activity in soybean," *The Plant Journal*, 12(5):991–998 (1997).

Scharff, Matthew D., et al., "Hybridomas As a Source of Antibodies," *Hospital Practice*, pp. 61–66 (Jan., 1981).

Tyson, Hugh, "Relationships, derived from optimum alignments, among amino acid sequences of plant peroxidases," *Can. J. Bot.* 70:543–556 (1992).

Vierling, R.A., and Wilcox, J.R., "Microplate assay for soybean seed coat peroxidase activity," *Seed Sci. & Technol.*, 24:485–494 (1996).

Vierling, Richard A., et al., "Non Peroxidase Oxidation of Guaiacol," *Seed Technology*, 20:91–93 (1998).

* cited by examiner

Primary Examiner—W. Gary Jones
Assistant Examiner—Juliet C. Einsmann
(74) Attorney, Agent, or Firm—Jondle & Associates PC

(57) ABSTRACT

The present invention relates to the genomic DNA and promoters of soybean peroxidases and their use as promoters for producing transgenic plants, including transgenic soybeans. The invention also relates to immunoassays or oligouncleotide assays which utilize soybean peroxidase as a marker. The invention further relates to the use of third antibody, an anti-soybean peroxidase antibody, in immunoassays. Soybean peroxidase may be bound to the anti-soybean peroxidase antibody prior to binding of this antibody with the second antibody (anti-antibody) in the assay. Alternatively, the anti-soybean peroxidase antibody is bound to the second antibody (anti-antibody) and then the soybean peroxidase bound by its specific antibody.

27 Claims, 40 Drawing Sheets

```
                                          sEP a1  ATG GGA AGC
                                          sEP a2  ... ... ...
                                              p1   M   G   S
                                              p2   .   .   .
AAC TTG AGG TTT TTG AGT CTT TGC CTC TTG GCA TTG ATT GCA TCG ACT CAT GCT
... ..C ... ... ... ... .. . .. . ... ... ... ... ..A ..C ... ...          -1
 N   L   R   F   L   S   L   C   L   L   A   L   I   A   S   T   H   A
 .   F   .   .   .   .   .   .   .   .   .   .   .   .   .   .   .   .
CAA CTT CAG CTT GGT TTT TAT GCT AAC AGT TGC CCA AAA GCA GAG CAA ATT GTT
... ... ... ... ... ... ... ..C ..G ... ... ... ..C ..T ... ... ..C ...
 Q   L   Q   L   G   F   Y   A   N   S   C   P   K   A   E   Q   I   V    18
 .   .   .   .   .   .   .   .   K   .   .   .   N   .   .   .   .   .
TTG AAA TTT GTT CAT GAC CAT ATC CAC AAT GCT CCA TCA CTA GCA GCA GCA TTA
... ... ... ..C ... ... ... ... ... ... ... ... ... ... ... ... ... ..G
 L   K   F   V   H   D   H   I   H   N   A   P   S   L   A   A   A   L    36
 .   .   .   .   .   .   .   .   .   .   .   .   .   .   .   .   .   .
ATA AGA ATG CAC TTT CAT GAC TGT TTT GTA AGG GGA TGT GAT GCA TCA GTC CTT
... ... ... ... ..C ... ... ... ... ... ... ... ... ... ... ... ... ...
 I   R   M  |H   F   H   D   C   F   V|  R   G   C   D   A   S   V   L    54
 .   .   .  .─── ─── ─── ─── ─── ─── ───.  .   .   .   .   .   .   .   .
CTG AAC TCA ACA ACC AAT CAG GCT GAG AAG AAT GCT CCT CCA AAT CTC ACA GTA
... ... ... ... ... ... ..A ... ..A ... ... ... ... ... ... ... ... ...
 L   N   S   T   T   N   Q   A   E   K   N   A   P   P   N   L   T   V    72
 .   .   .   .   .   .   .   .   .   .   .   .   .   .   .   .   .   .
AGA GGC TTT GAC TTC ATT GAC AGA ATA AAG AGC CTT GTT GAA GCT GAA TGC CCT
... ... ... ... ... ... ... ... ... ... ... ..G ..A ... ... ... ... ...
 R   G   F   D   F   I   D   R   I   K   S   L   V   E   A   E   C   P    90
 .   .   .   .   .   .   .   .   .   .   .   .   .   .   .   .   .   ‾
GGT GTG GTC TCT TGT GCT GAT ATC CTC ACT TTG GCT GCC AGA GAC ACT ATT GTA
... ... ... ... ... ... ... ... ... ... ..T ... ... ... ... ... ... ...
 G   V   V   S   C   A   D   I   L   T   L   A|  A   R   D   T   I   V   108
 .   .   .   .   .   .   .   .   .   .   .   S|  .   .   .   .   .   .
GCC ACA GGT GGA CCT TTT TGG AAA GTT CCA ACT GGT CGA AGG GAT GGG GTC GTC
... ... ... ..A ... ... ... ... ... ..A ... ... ..A ... ... ... ... A..
 A   T   G   G   P   F   W   K   V   P   T   G   R   R   D   G   V   V   126
 .   .   .   .   .   .   .   .   .   .   .   .   .   .   .   .   .   I
TCT AAC TTG ACG GAA GCC AGA AAT AAC ATT CCT GCT CCA TCT TCC AAC TTT ACC
... ... ... ... ... ... ... ..G ... ... ... ... ... ... ..T ... ... ...
 S   N   L   T   E   A   R   N   I   P   A   P   S   S   N   F   T       144
 .   .   .   .   .   .   .   D   .   .   .   .   .   .   .   .   .
```

FIG. 5A

```
ACC CTA CAA ACA CTC TTT GCT AAC CAA GGA CTT GAT TTG AAG GAC TTG GTC CTG
... ... ... ... ... ... ... ..C ... ... ... ... ... ... ... ... ... ...
 T   L   Q   T   L   F   A   N   Q   G   L   D   L   K  |D   L   V   L| 162
 .   .   .   .   .   .   .   .   .   .   .   .   .   . |.   .   .   .|
CTC TCT GGT GCT CAC ACA ATT GGT ATC GCT CAT TGC TCA TCA TTA TCA AAC CGG
... ... ... ... ... ... ... ... ... ... ... ... ... ..G ... ... ... ..C
|L   S   G   A   H   T   I|  G   I   A   H   C   S   S   L   S   N   R  180
 .   .   .   .   .   .   .   .   .   .   .   .   .   .   .   .   .   .
TTG TTC AAT TTC ACT GGC AAG GGT GAT CAA GAC CCG TCA CTA GAT AGT GAA TAT
... ... ... ... ... ... ... ... ... ... ... ... ..T ..C ... ... ... ...
 L   F   N   F   T   G   K   G   D   Q   D   P   S   L   D   S   E   Y  198
 .   .   .   .   .   .   .   .   .   .   .   .   .   .   .   .   .   .
GCT GCA AAT TTG AAA GCA TTC AAG TGC ACA GAC CTC AAC AAG TTG AAC ACC ACA
... ... ... C.. ... ..C ... ... ..G ... ... ... ..T ... ... ... ... ...
 A   A   N   L   K   A   F   K   C   T   D   L   N   K   L   N   T   T  216
 .   .   .   .   .   .   .   .   .   .   .   .   .   .   .   .   .   .
AAA ATT GAG ATG GAC CCT GGA AGT CGC AAG ACA TTT GAT CTT AGC TAC TAT AGT
... ... ... ... ... ... ... ... ... ... ... ... ... ... ... ... ... ...
 K   I   E   M   D   P   G   S   R   K   T   F   D   L   S   Y   Y   S  234
 .   .   .   .   .   .   .   .   .   .   .   .   .   .   .   .   .   .
CAC GTT ATT AAG AGA AGG GGT CTA TTT GAG TCA GAT GCT GCA TTA TTG ACT AAC
... ... ... ... ... ... ... ... ... ... ... ... ..G ... ..A ... ... ...
 H   V   I   K   R   R   G   L   F   E   S   D   A   A   L   L   T   N  252
 .   .   .   .   .   .   .   .   .   .   .   .   .   .   .   .   .   .
TCA GTT ACA AAG GCA CAA ATC ATC CAA TTG CTT GAA GGG TCA GTT GAA AAT TTC
... ... ... ... .G. ... ... ... ..T ..G ... ... ... ... ... ... ... ...
 S   V   T   K   A   Q   I   I   Q   L   L   E   G   S   V   E   N   F  270
 .   .   .   .   .   .   .   .   E   .   .   .   .   .   .   .   .   .
TTT GCT GAG TTT GCA ACC TCC ATC GAG AAA ATG GGA AGA ATT AAT GTG AAG ACA
... ... ... ... ... ... ... ..G ... ... ... ... ... ... ... ... ... ...
 F   A   E   F   A   T   S   I   E   K   M   G   R   I   N   V   K   T  288
 .   .   .   .   .   .   .   M   .   .   .   .   .   .   .   .   .   .
GGC ACA GAA GGA GAG ATC AGG AAG CAT TGT GCA TTT ATA AAT AGC TAA
..G ... ... ... ... ... ... ... ... ..C ... ... ... ... ... ...
 G   T   E   G   E   I   R   K   H   C   A   F   I   N   S  end
 .   .   .   .   .   .   .   .   .   .   .   .   L   .   .  end
```

FIG. 5B

```
                                                    sEP b1  ATG GCT GTC ATG
                                                    sEP b2  ... ... ... ...
                                                       p3   M   A   V   M
                                                       p4   .   .   .   .
GGT GCA TTC TTG AAT TTG ATC ATC *** TTT TCA GTA GTC TCT ACA ACA GGC AAG
... ... ... ... ... ... ... ... ATG ... ... ... ... ... *** ... ...        -1
 V   A   F   L   N   L   I   I   *   F   S   V   V   S   T   T   G   K
 .   .   .   .   .   .   .   .   M   .   .   .   .   .   *   .   .   .
TCA CTG AGC TTA AAC TAC TAT GCA AAA ACA TGC CCT AAT GTG GAG TTC ATT GTT
... ... ... ... ... ... T.. ... ... ... ... ... G.. ... ..A .G. ... ...    18
 S   L   S   L   N   Y   Y   A   K   T   C   P   N   V   E   F   I   V
 .   .   .   .   .   .   .   .   S   .   .   .   D   .   .   C   .   .
GCC AAG GCA GTA AAG GAT GCC ACT GCT AGG GAC AAA ACT GTT CCA GCA GCA ATT
... ... ... ..G ... ... ... ... ... ... ... ... ... ... ..T ... C.. ...    36
 A   K   A   V   K   D   A   T   A   R   D   K   T   V   P   A   A   I
 .   .   .   .   .   .   .   .   .   .   .   .   .   .   .   .   .   L
CTG CGA ATG CAC TTC CAT GAT TGT TTC GTT CGG GGG TGT GAT GCC TCT GTG CTG
... ... ... ... ... ..C ... ... ... ... ... ... .G. ... ... ... ... ...    54
 L   R   M  |H   F   H   D   C   F   V|  R   G   C   D   A   S   V   L
 .   .   .  |.   .   .   .   .   .   .|  .   .   G   .   .   .   .   .
CTA AAT TCA AAA GGA AAC AAC AAA GCA GAA AAA GAC GGG CCA CCA AAT GTT TCT
... ... ... ..G ... ... ... ... ... ... ... ..T ... ... ... ... ... ...    72
 L   N   S   K   G   N   N   K   A   E   K   D   G   P   P   N   V   S
 .   .   .   .   .   S   .   .   .   .   .   .   .   .   .   .   .   .
TTG CAT GCA TTC TAT GTC ATT GTA GCA GCA AAG AAA GCA CTA GAA GCT TCA TGC
... ... ... ... ... ... .AT ... ..G ... ... ... ... ... ... ... ... ...    90
 L   H   A   F   Y   V   I   V   A   A   K   K   A   L   E   A   S  |C
 .   .   .   .   .   .   D   .   .   .   .   .   .   .   .   .   .  |.
CCT GGT GTG GTC TCT TGT GCT GAC ATC CTT GCT CTG GCA GCA AGG GTC GCA GTT
..A ... ... ... ... ... ... ... ... ... ..A ... ... ... .AT ... ... ...    ##
 P   G   V   V   S   C   A   D   I   L   A   L|  A   R   V   A   V
 .   .   .   .   .   .   .   .   .   .   .   .|  .   D   .   .   .
TTT CTG TCA GGA GGA CCT ACA TGG GAT GTT CCT AAA GGA AGA AAG GAT GGT AGA
... ... ... ... ... ... ... ... .AA ... ... ... ... ... ..C ... ... ...   ##
 F   L   S   G   G   P   T   W   D   V   P   K   G   R   K   D   G   R
 .   .   .   .   .   .   .   .   E   .   .   .   .   .   .   .   .   .
ACA TCT AAA GCC AGT GAA ACC AGA CAA TTG CCA GCA CCA ACC TTC AAC TTA TCA
... ... ... ..C ... ... ... ... ..A ... ... ... ... ... ... ... ... ...   ##
 T   S   K   A   S   E   T   R   Q   L   P   A   P   T   F   N   L   S
 .   .   .   .   .   .   .   .   .   .   .   .   .   .   .   .   .   .
```

FIG. 6A

```
CAA CTG CGG CAA AGT TTC TCT CAA AGA GGA CTG TCA GGG GAA GAC CTG GTA GCT
... ... ... ... ... ..C ... ... ... ... ... ... ... ... ... ... ... ...
 Q   L   R   Q   S   F   S   Q   R   G   L   S   G   E  |D   L   V   A |  ##
 .   .   .   .   .   .   .   .   .   .   .   .   .   .  |.   .   .   . |
CTG TCA GGG GGG CAC ACT TTG GGT TTC TCT CAC TGC TCA TCT TTC AAG AAC AGA
... ... ... ... ... ... ... ... ... ... ... ... ... ... ... ... ... ...
|L   S   G   G   H   T |  L   G   F   S   H   C   S   S   F   K   N   R   ##
 .   .   .   .   .   .   .   .   .   .   .   .   .   .   .   .   .   .
ATC CAC AAC TTC AAT GCA ACA CAT GAT GTT GAC CCT TCA TTA AAT CCA TCA TTT
... ... ... ... ... ... ...T... ... ... .AA... ... ... ... ... ... ...
 I   H   N   F   N   A   T   H   D   V   D   P   S   L   N   P   S   F   ##
 .   .   .   .   .   .   .   E   .   .   .   .   .   .   .   .   .   .
GCA GCA AAA CTG ATC TCA ATT TGT CCA CTA AAA AAT CAG GCA AAA AAT GCA GGC
...A... ... ... ... ...A... ... ... ... ... ... ... ... ... ... ... ...
 A   A   K   L   I   S   I   C   P   L   K   N   Q   A   K   N   A   G   ##
 .   T   .   .   .   .   .   .   .   .   .   .   .   .   .   .   .   .
ACC TCT ATG GAC CCT TCA ACA ACA ACT TTT GAT AAT ACA TAT TAC AGG TTG ATC
... ... ... ... ... ... ... ... ... ... ... ... ... ... ... ... ... ...
 T   S   M   D   P   S   T   T   T   F   D   N   T   Y   Y   R   L   I   ##
 .   .   .   .   .   .   .   .   .   .   .   .   .   .   .   .   .   .
CTC CAA CAG AAA GGC TTG TTT TCT TCT GAT CAA GTT TTG CTT GAC AAC CCA GAC
... ... ... ... ... ... ... ... ... ... ... ... ... ... ... ... ... ...
 L   Q   Q   K   G   L   F   S   S   D   Q   V   L   L   D   N   P   D   ##
 .   .   .   .   .   .   .   .   .   .   .   .   .   .   .   .   .   .
ACT AAA AAT CTG GTT ACA AAG TTT GCC ACC TCA AAA AAG GCT TTT TAT GAG GCT
... ... ... ... ... ...G.G ... ... ... ... ... ... ... ... ... ..C ...
 T   K   N   L   V   T   K   F   A   T   S   K   K   A   F   Y   E   A   ##
 .   .   .   .   .   A   .   .   .   .   .   .   .   .   .   .   D   .
TTT GCG AAG TCC ATG ATC AGA ATG AGT AGC TAC AAT GGT GGA CAG GAG GTT AGA
... ... ... ... ... ...A. ... ... ...AT. ... ... ... ... ... ... ...
 F   A   K   S   M   I   R   M   S   S   Y   N   G   G   Q   E   V   R   ##
 .   .   .   .   .   .   K   .   .   .   I   .   .   .   .   .   .   .
AGG ACT GCA GAA TGA
... ... ... ..G ...
 R   T   A   E   end
 .   .   .   .   end
```

FIG. 6B

FIG. 9A  SP-THREE ANTIBODY SYSTEM

FIG. 9B  STANDARD TWO ANTIBODY SYSTEM

Dot Blot Comparison of 3 antibody SBP and 2 antibody HRP systems

Western Blot A, a 2 antibody system using Horseradish Peroxidase
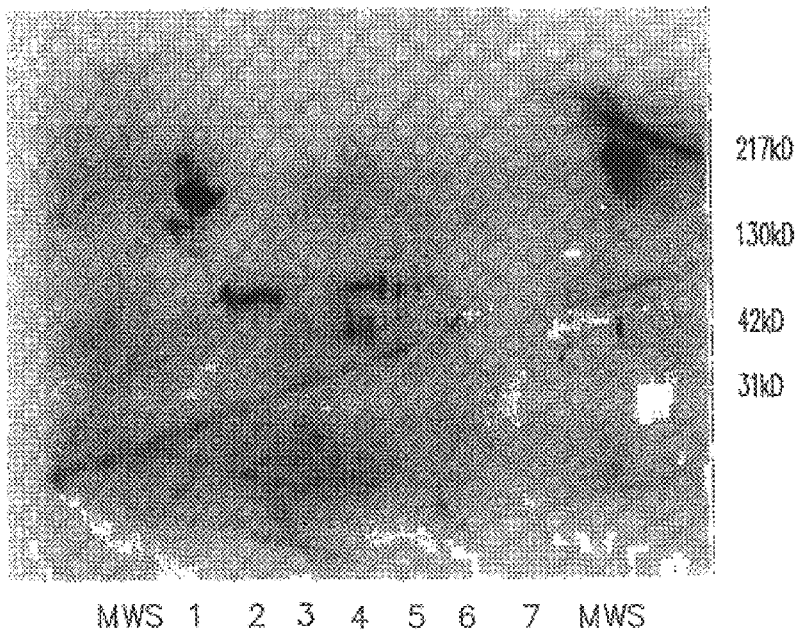
MWS 1 2 3 4 5 6 7 MWS
Western Blot B, a 3 antibody system using Soybean Peroxidase-Antiperoxidase
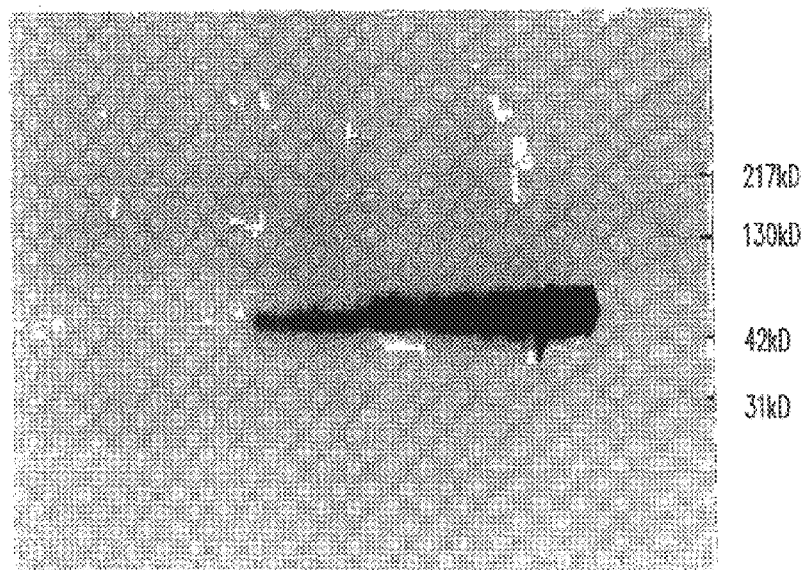
Lane1=.25ug Fetuin
Lane2=.50ug Fetuin
Lane3= 1ug Fetuin
Lane4= 2ug Fetuin
Lane5= 4ug Fetuin
Lane6= 8ug Fetuin
MWS 1 2 3 4 5 6 7 MWS
Lane 7 = 16ug Fetuin
MWS = Kaleidoscope Molecular
Weight Standard
FIG. 13

```
   1  TCAATGTCAG AATGATACTG ACAGATCTAA TTTCGGTTAA TTTGATTACT
  51  AATTAGTAGG TGCCAGTGGC ATAAATTGAA TAAGAAATAA AAATAATTCA
 101  TTATCAATTC AAATGAAGGA AAAATATATT GTGTCAAAAG GATATTAATT
 151  ATCAAGATTC AAAGGAAAAA ATAGTATACT CTTTTTTATA AATACACTAC
 201  TGAGTAATTT AACCAAATTT AAATTATAAT TTTAATGCTC AGTTTACTTC
 251  AATGGCTATA CCTTTTTTTT ATATATTCAA TGGCTATACC TATAAATTGT
 301  AATATTCAAG CATTGTTTTA ATGGAAGCAA ACAAGGCATC ACATATGGCT
 351  AGGAAGAATT GAACAAAAAC AAATTAGCTA CATACATTAA GCTCTTAATA
 401  TTATAAAAAC ATGCCGATGA TATATGTCCA TAGATTTCAA GGGAGCTAAT
 451  ACCGGAAAGT GTCAAGGATT TATACTTTAC AGCTAAAGTT TCAGTCTCAA
 501  AGAAAATGAT GACACTGTAT CATTGAGCAG ACACAATGAG TTACATCACA
 551  AAACCAGCCT GTAGGGATAC ATGACTCATA TTCCTTGTCA AATATCGCTG
 601  CCTCAATGTG CATAGCGATT ATAGTAATGG ATTCACAGTA AAGGAGCAGG
 651  TAAGCCAATT TTTTATTCTT AAATTCCCTG TTGAGACTAC ATTATATTTT
 701  TGAATTGCGA GATATTCAAG GATTACTTGT TATATATGTT AAGCCGCCGC
 751  ATACTGTTTA AAGTATTAAT GATATATCAT TGTTACTATA AAATATTTTT
 801  ACACAATGCA AGGTAAATAT TTCTATTACA TGTTGACATA AAAATATCTT
 851  ACGTAAACTA AACTAAACTC TTGTTTAAAA TGGTACTAGT ATCTATACAA
 901  CGAGATTAAA GCTACAAAAA TATGATACAA AGAGGGAGAT TTTGTATAGT
 951  ATCCTATGCT TGAAGAACGT ATCAACATCC AGTATCTCGA AAATTCAGTA
1001  CTAAAATGTA AAATCTATTG ATGTGTACTG AAGGATTCAG AAATTCAACT
1051  ATTTTGAACT CGCTGTATAT TAATTTGTCC ATATAAGGTC ACAGCAGCCA
1101  ACTAATCATT TTTTATTAG AGACTAGATA CAATTATTAC ATGCAAATGG
1151  ATAATAAAGT AGCATGTAGC ATCACCTTAT CGCACATGTT AGTTAGCTGC
1201  ATGGACCATC TGTATGATTT GTGATGTGTC TTGTAGCTTA ACTTAAGCAC
1251  TATATATCAC TGATCAGTGT TGTGGAAACA GCGAAGAGAA ATGAAATTGC
1301  CTCTTTCAAG AAGCATCTGA GTGTTTACTA TTTTGTACTA TATTTATATA
```

Figure 14A

```
1351  TAGTCACTCA AGCTTCTAGG ATTTCTGCCT GCTGCATCAA AATGGGAAGC
1401  AACTTGAGGT TTTTGAGTCT TTGCCTCTTG GCATTGATTG CATCAACTCA
1451  TGCTCAACTT CAGCTTGGTT TTTATGCTAA CAGTTGCCCA AAAGCAGAGC
1501  AAATTGTTTT GAAATTTGTT CATGACCATA TCCACAATGC TCCATCACTA
1551  GCAGCTGCAT TAATAAGAAT GCACTTCCAT GACTGTTTTG TAAGGGTATG
1601  TGGTTCAAGC CTATAATTTT CTTTCATTTT TTACTTAACA AGTACCATAT
1651  ATGTTAGATT AAAGAACTAA CTAAGATGAA GTATTTCAGG GATGTGATGC
1701  ATCAGTCCTT CTGAACTCAA CAACCAATCA GGCTGAGAAG AATGCTCCTC
1751  CAAATCTCAC AGTAAGAGGC TTTGACTTCA TTGACAGAAT AAAGAGCCTT
1801  GTTGAAGCTG AATGCCCTGG TGTGGTCTCT TGTGCTGATA TCCTCACTTT
1851  GGCTGCCAGA GACACTATTG TAGCCACAGT AAGTACTCAA TTGCTATCAG
1901  GAAAATCTTA AGAGTATAAG CACAACTTCT GCTTCACCTT TATATCTTTA
1951  CACTTCTTTT TGAGAACAAG ATGACCCATT TGCTGGTTTA TGCCATTACT
2001  GACATTGGTG TTCAGGGTGG ACCTTTTTGG AAAGTTCCAA CTGGTCGAAG
2051  GGATGGGGTC GTCTCTAACT TGACGGAAGC CAGAAATAAC ATTCCTGCTC
2101  CATTTTCCAA CTTCACCACC CTACAGACAC TCTTTGCTAA CCAAGGACTT
2151  GATTTGAAGG ACTTGGTCCT GCTCTCTGGT ATCATTTATG AAACAAATCC
2201  TAAGCATTAT TGTTGAAAGA CTAACACGTT TTTGAGTCCC TCATGGTAAC
2251  GCCAGGTTTC CAGTCACGAC GTTGTAAAAC GACGGCCAGT GAGCGCGCAG
2301  TAATACGACT CACTATAGGC GAATTGGAGC TCCAGCGGTG GCGGCCGCTC
2351  TAGAACTAGT GGATCCCCCG GCTGCAGGT TTTCGATATC AAGCTTATCG
2401  ATACCGTCGA CACCTCGAGT TGGAAATATG TCTAAATATC TGCAATTTCA
2451  ACATGAATAA TTTATTTTTT AGGAATTTAT TAACTACATT TTAAATTTTC
2501  AGGATATTGA TTTGATAATT CTTATTATTT AGACTTTAGG ACACTATCAG
2551  TTTGTTTAAT TTCAAGGTTA AGATGTGTTA TATTTGAAT TTTGCATTAC
2601  ATTATTTCAT TTTAAAAAAT AAAACCAACA AATTGGCATG AATTATACAT
2651  TGTTCTTGGG CTTGTAATGA GCAAGAGTTC AAATTGTTTC AGGTGCTCAC
```

Figure 14B

```
2701  ACAATTGGTA TCGCTCATTG CTCATCATTA TCAAACCGGT TGTTCAATTT
2751  CACTGGCAAG GGTGATCAAG ACCCGTCACT AGATAGTGAA TATGCTGCAA
2801  ATTTGAAAGC ATTCAAGTGC ACAGACCTCA ACAAGTTGAA CACCACAAAA
2851  ATTGAGATGG ACCCTGGAAG TCGCAAGACA TTTGATCTTA GCTACTATAG
2901  TCACGTTATT AAGAGAAGGG GTCTATTTGA GTCAGATGCT GCATTATTGA
2951  CTAACTCAGT TACAAAGGCA CAAATCATCC AATTGCTTGA AGGGTCAGTT
3001  GAAAATTTCT TTGCTGAGTT TGCAACCTCC ATCGAGAAAA TGGGAAGAAT
3051  TAATGTGAAG ACAGGGACAG AAGGAGAGAT CAGGAAGCAT TGTGCATTTA
3101  TAAATAGCTA AGAATCTTGT CTTGTTCATG GATGAATCTT GTATCATTTA
3151  TTTTTTGGGG TTTGATTATT TATGCTATGC CATGTTTTTT GATTAGTTAT
3201  GCTATGCCAT GTGGTCTCTG TCTACATACG TGTGATCCTT TATGGTATGG
3251  TTGTTGTATG TGTGTTGGAA TAAGTGGGCT CTTAAGTTAT TCATATTTCC
3301  AACTTTGCTG GTAGATCATG CTCTTGTAAT AAGAACCAGA A
SEQ ID NO:18
```

Figure 14C

```
   1  CAATAATTAT AGTTTGATAG CCTGCTACCA TCAAGGATTG CAATGCAAGC
  51  TTTGGCACCA AAAACAAAAT TACGATGGCT CAACCTCAAC CTTAACTACC
 101  GCATACATTG GTATAACTCA GGCGCAGTTT GGTTTGCTAG TGAAACCACT
 151  AGTGATTTGG TTAGTGCTGA TCAGACTTTG AGTGACTTTT TTATGTCGTG
 201  CCATTTTCAA TTAAATGTCT AAAATTTTA AGATAATTAA ACAACTTTTT
 251  TATTTTAAA AAGCTAAAAC ACAAAAGAA ATGAGTACTT TTCTTGTAAA
 301  TTGACAATAA TGGTTTTTTT TATAAAAAAA AAAATAAGTG TCTTACAAAA
 351  GAAAATTATC CAAACATAAC ACTAATATGG CATGGACAAT TGGCCACGAG
 401  GCTGTTGGCC TCAATTTCCG TTGAAAAGCC TAAACTGAAA TATGGCAAGA
 451  GTTTGATCAC AGAAAAAAAT GGTCGGGGTA AAATCAAACT TTCACTTATT
 501  ACATTAGGAC AATAGGAGAA AGACCAAGGA TAATGTCATA ATCAACGAAT
 551  CATAATTATG TATCATGGGG TGGAGGATGA CATCGTGATT TGTGATATTA
 601  CCAACTACTC TTGAAGAGTT TAGACCATGA AACTATAGCT TAAGACTGGA
 651  TTTAGCATGA ATATGTAATT AAATTATTCT GGATCGAGAG TAACATACCA
 701  ATAAAAAAAA AAGAAGAGGA ACATCACAAG CCACAGAAAG CTACCGGAGG
 751  CTTAAAAAGT TTAAGGTTCA TTAGGACGGA GCATAAAGTG GATTGTCTTT
 801  TAGTAATGAG AATGCTTCAA CATTACTACT CTTGATTGAC AGTACTTCTT
 851  AACGAATTGA TTTCTAGGGC CACATTATCT CAAACAATAA TTGATCTCTT
 901  TTATATCTAT AAAAATTCAT TTTCCCCATC TTTGATTTCC ACGGCTAAAA
 951  GCTAAATATC ATCAAAGTAC TCAAATTAGC ATGGCTGTCA TGGTTGCATT
1001  CTTGAATTTG ATCATCATGT TTTCAGTAGT CTCTACAACA GGCAAGTCAC
1051  TGAGCTTAAA CTACTATGCA AAAACATGCC CTAATGTGGA GTTCATTGTT
1101  GCCAAGGCAG TAAAGGATGC CACTGCTAGG AAAAAACTGT TCCAGCAGCA
1151  ATTCTGCGAA TGCACTTCCA TGATTGTTTC GTTCGGGTAA TGCTATTTTG
1201  ACCCCTCCTC CCTCCTTTCC TCTTGACCGT TCCGCCTCAT TTGATGCATC
1251  ATGAAATCAA ATCATATTGT TTTCTTTTTT CCTATACTCT TGAAGGGGTG
1301  TGATGCCTCT GTGCTGCTAA ATTCAAAAGG AAACAACAAA GCAGAAAAAG
```

Figure 15A

```
1351  ACGGGCCACC AAATGTTTCT TTGCATGCAT TCTATGTCAT TGATGCAGCA
1401  AAGAAAGCAC TAGAAGCTTC ATGCCCTGGT GTGGTCTCTT GTGCTGACAT
1451  CTCTGCTCTG GCAGCAAGGG TCGCAGTTTT TCTGGTAAGA AAACTTTGAA
1501  AAGTACCAAA TTTCTCATCA TTCAGATCCT AAACTAAACA ATCATTATGT
1551  CTTCGAGAAT TGACAAATGC AGCTAAGGTG GCTTGTATTT GGAAGTCTTG
1601  ACTAATTGTA TAAAATATAT TCTGCAGTCA GGAGGACCTA CATGGGATGT
1651  TCCTAAAGGA AGAAAGGATG GTAGAACATC TAAAGCCAGT GAAACCAGAC
1701  AATTGCCAGC ACCAACCTTC AACTTATCAC AACTGCGGCA AGTTTCTCT
1751  CAAAGAGGAC TGTCAGGGGA AGACCTGGTA GCTCTGTCAG GTAAGCTATT
1801  CCTAAAGTCA AAACTGCCAA AACTTGACCA TTTTTCATTT ATTCCAATTT
1851  ATATCTGAAT AGAGTTTAGA GTTTCTCCTT TGACTCATAT GTAGGGGGC
1901  ACACTTTGGG TTTCTCTCAC TGCTCATCTT TCAAGAACAG AATCCACAAC
1951  TTCAATGCAA CACATGATGT TGACCCTTCA TTAAATCCAT CATTTGCAGC
2001  AAAACTGATC TCAATTTGTC CACTAAAAAA TCAGGCAAAA AATGCAGGCA
2051  CCTCTATGGA CCCTTCAACA ACAACTTTTG ATAATACATA TTACAGGTTG
2101  ATCCTCCAAC AGAAAGGCTT GTTTTCTTCT GATCAAGTTT TGCTTGACAA
2151  CCCAGACACT AAAAATCTGG TTACAAAGTT TGCCACCTCA AAAAAGGCTT
2201  TTTATGAGGC TTTTGCGAAG TCCATGATCA GAATGAGTAG CTACAATGGT
2251  GGACAGGAGG TTAGAAGGAC TGCTGAATGA tcaattaata agtcttaaat
2301  caattcaagt taaattgatg ttccaaacaa gttggatcaa atttcctaga
2351  tgccaagaat attatgtctt tttcctctat taaagaaata tgtatattta
2401  tctg    SEQ ID NO:19
```

Figure 15B

*GmEPA1*

```
     tcaatgtcagaatgatactgacagatctaatttcggttaatttgattactaattagtagg
     tgccagtggcataaattgaataagaaataaaaataattcattatcaattcaaatgaagga
     aaaatatattgtgtcaaaaggatattaattatcaagattcaaaggaaaaaatagtatact
     cttttttataaatacactactgagtaatttaaccaaatttaaattataattttaatgctc
                    repeat I                       repeat I
agtttacttcaatggctatacctttttttatatattcaatggctatacctataaattgt
     aatattcaagcattgttttaatggaagcaaacaaggcatcacatatggctaggaagaatt
                                                          repeat II
     gaacaaaaacaaattagctacatacattaagctcttaatattataaaaacatgccgatga
                                                     repeat III
     tatatgtccatagatttcaagggagctaataccggaaagtgtcaaggatttatactttac
     agctaaagtttcagtctcaaagaaaatgatgacactgtatcattgagcagacacaatgag
     ttacatcacaaaaccagcctgtagggatacatgactcatattccttgtcaaatatcgctg
     cctcaatgtgcatagcgattatagtaatggattcacagtaaaggagcaggtaagccaatt
                                                          repeat III
     ttttattcttaaattccctgttgagactacattatattttgaattgcgagatattcaag
                                                      repeat II
     gattacttgttatatatgttaagccgccgcatactgtttaaagtattaatgatatatcat
     tgttactataaaatattttacacaatgcaaggtaaatatttctattacatgttgacata
     aaaatatcttacgtaaactaaactaaactcttgtttaaaatggtactagtatctatacaa
     cgagattaaagctacaaaaatatgatacaaagagggagattttgtatagtatcctatgct
     tgaagaacgtatcaacatccagtatctcgaaaattcagtactaaaatgtaaaatctattg
                             repeat IV
     atgtgtactgaaggattcagaaattcaactattttgaactcgctgtatattaatttgtcc
     atataaggtcacagcagccaactaatcatttttttattagagactagatacaattattac
     atgcaaatggataataaagtagcatgtagcatcaccttatcgcacatgttagttagctgc
     atggaccatctgtatgatttgtgatgtgtcttgtagcttaacttaagcactatatcac
     tgatcagtgttgtggaaacagcgaagagaaatgaaattgcctcttcaagaagcatctga
           repeat IV
     gtgtttactattttgtactatatttatatatagtcactcaagcttctaggatttctgcct
     gctgcatcaaaATGGGAAGCAACTTGAGGTTTTTGAGTCTTTGCCTCTTGGCATTGATTG
                 M  G  S  N  L  R  F  L  S  L  C  L  L  A  L  I  A
     CATCAACTCATGCTCAACTTCAGCTTGGTTTTTATGCTAACAGTTGCCCAAAAGCAGAGC
       S  T  H  A  Q  L  Q  L  G  F  Y  A  N  S  C  P  K  A  E  Q
     AAATTGTTTTGAAATTTGTTCATGACCATATCCACAATGCTCCATCACTAGCAGCTGCAT
         I  V  L  K  F  V  H  D  H  I  H  N  A  P  S  L  A  A  A  L
     TAATAAGAATGCACTTCCATGACTGTTTTGTAAGGgtatgtggttcaagcctataatttt
         I  R  M  H  F  H  D  C  F  V  R
     ctttcattttttacttaacaagtaccatatatgttagattaaagaactaactaagatgaa
     gtatttcagGGATGTGATGCATCAGTCCTTCTGAACTCAACAACCAATCAGGCTGAGAAG
                G  C  D  A  S  V  L  L  N  S  T  T  N  Q  A  E  K
     AATGCTCCTCCAAATCTCACAGTAAGAGGCTTTGACTTCATTGACAGAATAAAGAGCCTT
       N  A  P  P  N  L  T  V  R  G  F  D  F  I  D  R  I  K  S  L
     GTTGAAGCTGAATGCCCTGGTGTGGTCTCTTGTGCTGATATCCTCACTTTGGCTGCCAGA
       V  E  A  E  C  P  G  V  V  S  C  A  D  I  L  T  L  A  A  R
     GACACTATTGTAGCCACAgtaagtactcaattgctatcaggaaaatcttaagagtataag
       D  T  I  V  A  T
     cacaacttctgcttcacctttatatctttacacttcttttttgagaacaagatgacccatt
     tgctggtttatgccattactgacattggtgttcagGGTGGACCTTTTTGGAAAGTTCCAA
                                          G  G  P  F  W  K  V  P  T
     CTGGTCGAAGGGATGGGGTCGTCTCTAACTTGACGGAAGCCAGAAATAACATTCCTGCTC
         G  R  R  D  G  V  V  S  N  L  T  E  A  R  N  N  I  P  A  P
     CATTTTCCAACTTCACCACCCTACAGACACTCTTTGCTAACCAAGGACTTGATTTGAAGG
         F  S  N  F  T  T  L  Q  T  L  F  A  N  Q  G  L  D  L  K  D
     ACTTGGTCCTGCTCTCTGgtatcatttatgaaacaaatcctaagcattattgttgaaaga
         L  V  L  L  S  G
     ctaacacgttttgagtccctcatggtaacgccaggtttccagtcacgacgttgtaaaac
     gacggccagtgagcgcgcagtaatacgactcactataggcgaattggagctccagcggtg
     gcggccgctctagaactagtggatccccgggctgcaggttttcgatatcaagcttatcg
     ataccgtcgacacctcgagttggaaatatgtctaaatatctgcaatttcaacatgaataa
```

Figure 16A1

```
tttattttttaggaatttattaactacattttaaattttcaggatattgatttgataatt
cttattatttagactttaggacactatcagtttgtttaatttcaaggttaagatgtgtta
tattttgaattttgcattacattatttcattttaaaaaataaaaccaacaaattggcatg
aattatacattgttcttgggcttgtaatgagcaagagttcaaattgtttcagGTGCTCAC
                                                     A  H
ACAATTGGTATCGCTCATTGCTCATCATTATCAAACCGGTTGTTCAATTTCACTGGCAAG
 T  I  G  I  A  H  C  S  S  L  S  N  R  L  F  N  F  T  G  K
GGTGATCAAGACCCGTCACTAGATAGTGAATATGCTGCAAATTTGAAAGCATTCAAGTGC
 G  D  Q  D  P  S  L  D  S  E  Y  A  A  N  L  K  A  F  K  C
ACAGACCTCAACAAGTTGAACACCACAAAAATTGAGATGGACCCTGGAAGTCGCAAGACA
 T  D  L  N  K  L  N  T  T  K  I  E  M  D  P  G  S  R  K  T
TTTGATCTTAGCTACTATAGTCACGTTATTAAGAGAAGGGGTCTATTTGAGTCAGATGCT
 F  D  L  S  Y  Y  S  H  V  I  K  R  R  G  L  F  E  S  D  A
GCATTATTGACTAACTCAGTTACAAAGGCACAAATCATCCAATTGCTTGAAGGGTCAGTT
 A  L  L  T  N  S  V  T  K  A  Q  I  I  Q  L  L  E  G  S  V
GAAAATTTCTTTGCTGAGTTTGCAACCTCCATCGAGAAAATGGGAAGAATTAATGTGAAG
 E  N  F  F  A  E  F  A  T  S  I  E  K  M  G  R  I  N  V  K
ACAGGGACAGAAGGAGAGATCAGGAAGCATTGTGCATTTATAAATAGCtaagaatcttgt
 T  G  T  E  G  E  I  R  K  H  C  A  F  I  N  S
cttgttcatggatgaatcttgtatcatttattttttggggtttgattatttatgctatgc
catgttttttgattagttatgctatgccatgtggtctctgtctacatacgtgtgatcctt
tatggtatggttgttgtatgtgtgttggaataagtgggctcttaagttattcatatttcc
aactttgctggtagatcatgctcttgtaataagaaccagaa
```

Figure 16A2

*GmEPB1*

```
caataattatagtttgatagcctgctaccatcaaggattgcaatgcaagctttggcacca
aaaacaaaattacgatggctcaacctcaaccttaactaccgcatacattggtataactca
   ggcgcagtttggtttgctagtgaaaccactagtgatttggttagtgctgatcagactttg
       repeat I
   agtgactttttatgtcgtgccattttcaattaaatgtctaaaattttaagataattaa
       repeat I
   acaactttttattttaaaaagctaaaacacaaaaagaaatgagtacttttcttgtaaa
                    repeat II
   ttgacaataatggttttttttataaaaaaaaaataagtgtcttacaaaagaaaattatc
   caaacataacactaatatggcatggacaattggccacgaggctgttggcctcaatttccg
   ttgaaaagcctaaactgaaatatggcaagagtttgatcacagaaaaaaatggtcggggta
   aaatcaaactttcacttattacattaggacaataggagaaagaccaaggataatgtcata
   atcaacgaatcataattatgtatcatggggtggaggatgacatcgtgatttgtgatatta
     repeat III
   ccaactactcttgaagagtttagaccatgaaactatagcttaagactggatttagcatga
                                     repeat II
   atatgtaattaaattattctggatcgagagtaacataccaataaaaaaaaaagaagagga
   acatcacaagccacagaaagctaccggaggcttaaaaagtttaaggttcattaggacgga
                      repeat III
   gcataaagtggattgtctttagtaatgagaatgcttcaacattactactcttgattgac
   agtacttcttaacgaattgatttctagggccacattatctcaaacaataattgatctctt
   ttatatctataaaaattcattttccccatctttgatttccacggctaaaagctaaatatc
   atcaaagtactcaaattagcATGGCTGTCATGGTTGCATTCTTGAATTTGATCATCATGT
                        M  A  V  M  V  A  F  L  N  L  I  I  M  F
TTTCAGTAGTCTCTACAACAGGCAAGTCACTGAGCTTAAACTACTATGCAAAAACATGCC
 S  V  V  S  T  T  G  K  S  L  S  L  N  Y  Y  A  K  T  C  P
CTAATGTGGAGTTCATTGTTGCCAAGGCAGTAAAGGATGCCACTGCTAGGAAAAAAACTG
 N  V  E  F  I  V  A  K  A  V  K  D  A  T  A  R  K  K  T  V
TTCCAGCAGCAATTCTGCGAATGCACTTCCATGATTGTTTCGTTCGGgtaatgctatttt
 P  A  A  I  L  R  M  H  F  H  D  C  F  V  R
gacccctcctccctcctttcctcttgaccgttccgcctcatttgatgcatcatgaaatca
aatcatattgttttcttttttcctatactcttgaagGGGTGTGATGCCTCTGTGCTGCTA
                                      G  C  D  A  S  V  L  L
AATTCAAAAGGAAACAACAAAGCAGAAAAAGACGGGCCACCAAATGTTTCTTTGCATGCA
 N  S  K  G  N  N  K  A  E  K  D  G  P  P  N  V  S  L  H  A
TTCTATGTCATTGTAGCAGCAAAGAAAGCACTAGAAGCTTCATGCCCTGGTGTGGTCTCT
 F  Y  V  I  V  A  A  K  K  A  L  E  A  S  C  P  G  V  V  S
TGTGCTGACATCTCTGCTCTGGCAGCAAGGGTCGCAGTTTTTCTGgtaagaaaactttga
 C  A  D  I  S  A  L  A  A  R  V  A  V  F  L
aaagtaccaaatttctcatcattcagatcctaaactaaacaatcattatgtcttcgagaa
ttgacaaatgcagctaaggtggcttgtatttggaagtcttgactaattgtataaaatata
ttctgcagTCAGGAGGACCTACATGGGATGTTCCTAAAGGAAGAAAGGATGGTAGAACAT
         S  G  G  P  T  W  D  V  P  K  G  R  K  D  G  R  T  S
CTAAAGCCAGTGAAACCAGACAATTGCCAGCACCAACCTTCAACTTATCACAACTGCGGC
 K  A  S  E  T  R  Q  L  P  A  P  T  F  N  L  S  Q  L  R  Q
AAAGTTTCTCTCAAAGAGGACTGTCAGGGGAAGACCTGGTAGCTCTGTCAGgtaagctat
 S  F  S  Q  R  G  L  S  G  E  D  L  V  A  L  S  G
tcctaaagtcaaaactgccaaaacttgaccatttttcatttattccaatttatatctgaa
tagagtttagagtttctcctttgactcatatgtagGGGGGCACACTTTGGGTTTCTCTCA
                                     G  H  T  L  G  F  S  H
CTGCTCATCTTTCAAGAACAGAATCCACAACTTCAATGCAACACATGATGTTGACCCTTC
 C  S  S  F  K  N  R  I  H  N  F  N  A  T  H  D  V  D  P  S
ATTAAATCCATCATTTGCAGCAAAACTGATCTCAATTTGTCCACTAAAAAATCAGGCAAA
 L  N  P  S  F  A  A  K  L  I  S  I  C  P  L  K  N  Q  A  K
AAATGCAGGCACCTCTATGGACCCTTCAACAACAACTTTTGATAATACATATTACAGGTT
 N  A  G  T  S  M  D  P  S  T  T  T  F  D  N  T  Y  Y  R  L
GATCTCCAACAGAAAGGCTTGTTTTCTTCTGATCAAGTTTTGCTTGACAACCCAGACAC
 I  L  Q  Q  K  G  L  F  S  S  D  Q  V  L  L  D  N  P  D  T
TAAAAATCTGGTTACAAAGTTTGCCACCTCAAAAAAGGCTTTTTATGAGGCTTTTGCGAA
 K  N  L  V  T  K  F  A  T  S  K  K  A  F  Y  E  A  F  A  K
```

Figure 16B1

```
GTCCATGATCAGAATGAGTAGCTACAATGGTGGACAGGAGGTTAGAAGGACTGCTGAAtg
 S   M   I   R   M   S   S   Y   N   G   G   Q   E   V   R   R   T   A   E
atcaattaataagtcttaaatcaattcaagttaaattgatgttccaaacaagttggatca
aatttcctagatgccaagaatattatgtcttttcctctattaaagaaatatgtatattt
atctgaagttaataaaatc
```

Figure 16B2

*GmEPC*

```
           aaaatgggatataattttttctcagatgttgtttatactgttttttttaatcagaattaaaa
                 repeat I                  repeat I
           ttaatctttaattatcgacataatttttttggtgaatattatcgacataattatttaat
acaaattttttattgtacatagaagtgatacttcaattttaatattggagaacagtacgaa
           aacataaaaaaactgttattagaagaaaaaaatatatggaaaaggttagctacatatatt
           agctaaattagttgttctaattggctatataaacccctattgtactctttgtaatctcacc
           tttttcatttaaatacatttctactttttaagttctatattttctctcaatttttcttcga
           taaaccatgaaatttaacatggtatatcagcgataccacccactttgaaagccatgtatg
           gctagtatgggcagccaaaatttgccctggttcaagcaaagcaagtgtttatatagatgt
           gactttgttgaggaactcatgccaatggtactgattgtgaaactgagaaaactaatttg
           gagaatttgaattatgatcattaaatactcctctcctgactaccttcgtccctcaaattt
                                                        repeat II
           gtaccatcattatttcccaaaaatttgattacaatgcactaattaatgaatgtttcttac
           attatcatattatcatatctgacattttgttttttactttttataataattattttaaaaa
           gtcatacatgcaaataatttttttaatagtttacagttaaattttttacagtaaaaatgcat
           gaaaattaaacttattttttccaagtcatcatttagtcaaatcccaaaacaatgattatt
              repeat II
           ttttgcaaatgaatgtttattgaacatttaaatgtagcctaattaattctggttatggtg
           tcaatgttccaaaacctaatgcaagatcttagcaagtacatacatagatctaattttaaa
           cttatctttacgcaagagatataaagattatacatctagttttaaacattaacttttgtt
                                                        repeat III & IV
           tttgtgttaaaaaacagtaacattttcttaattttgtagagtgacgtgctccaaccatat
           taacgaagatttttaattggtattcaagttcatgaacttagtaaataagttttggtcttca
           gttttcaattttcattacaacatttatgtaaaatatcaacgtttttctgaaatttgttgct
              repeat III
           tgtgtgctccaaccacatttaagagattatagaaattaattttcaagaagataagattcc
           tactcttgcctggccctaccatagtacaataaatccactcataaatcaacaagtcgtcgt
           cataggcaattgggcatcatatcataaacaatacgtacgtgatattatctagtgtctctc
           agtttacttttatgagaaattattttttctttaaaaaaagttaattaataaaaacatttgcg
           ataccgtgagttacaagaaatccgccgaattcatctctataaataaaaggatctatatga
                        repeat IV
           gaggtaaaatcatattaactcaaaATGGGTTCCATGCGTCTATTAGTAGTGGCATTGTTG
                                     M  G  S  M  R  L  L  V  V  A  L  L
TGTGCATTTGCTATGCATGCAGGTTTTTCAGTCTCTTATGCTCAGCTTACTCCTACGTTC
 C  A  F  A  M  H  A  G  F  S  V  S  Y  A  Q  L  T  P  T  F
TACAGAGAAACATGTCCAAATCTGTTCCCTATTGTGTTTGGAGTAATCTTCGATGCTTCT
 Y  R  E  T  C  P  N  L  F  P  I  V  F  G  V  I  F  D  A  S
TTCACCGATCCCCGAATCGGGGCCAGTCTCATGAGGCTTCATTTTCATGATTGCTTTGTT
 F  T  D  P  R  I  G  A  S  L  M  R  L  H  F  H  D  C  F  V
CAAgtacgtacttttttttttccttccaaaatgccctgcatatttaacaagattgctttg
 Q
ttcacctagaaaaatgtgttttttttcaacgatcttacgtacgtttgtttggtttgaaaaa
taaatcagaaagagatcaagaaaatagctagaaagaaagcaacgttttttttaaaaggtat
ttagtgtgagaaaaatattaaaactgaagagaaagaaattaaataagcttttcttgaatg
atatttacatgtcttattaacttaaagtcaccttttttctttaagttgtgcttgaagaaa
aaagatgtctttcagtttagttttgattaatgctaattatattttttaattaattaattaa
tactatatatctatttaccatattaattattactatatttcatgatgacaacagacaagt
attctaaagaggtatcggtagatgattaattttttttataaaaaaatcttttgcgtgtata
gatattcttttataattggtgcagaaacttgtaatgctaattgcaattaatcttacattg
attaactaatagctataatcaatatttaggttaggtataggagacaaatcaagtgatctg
aacaaattaagttgttatatttgcattgtgacagGGTTGTGATGGATCAGTTTTGCTGAA
                                     G  C  D  G  S  V  L  L  N
CAACACTGATACAATAGAAAGCGAGCAAGATGCACTTCCAAATATCAACTCAATAAGAGG
 N  T  D  T  I  E  S  E  Q  D  A  L  P  N  I  N  S  I  R  G
ATTGGACGTTGTCAATGACATCAAGACAGCGGTGGAAAATAGTTGTCCAGACACAGTTTC
 L  D  V  V  N  D  I  K  T  A  V  E  N  S  C  P  D  T  V  S
TTGTGCTGATATTCTTGCTATTGCAGCTGAAATAGCTTCTGTTCTGgtaattaataactc
 C  A  D  I  L  A  I  A  A  E  I  A  S  V  L
ctaattaattcccaaccattaaaaagttgcatgattggattcaaaattctatggtattgg
ggttctgatataaatttgtaattaaattgcactaaaaaaaattatcatatactttttaata
```

Figure 16C1

```
aaaaaaatttatctaatttaatttattattaaaactatttttaaaattcaatcctaactc
tttttaatcggagcatgtaagctggcacccaccgtatatcgttggaagatgctataaaa
ccatttaattaatggatggaatcagtcaaaacatttaattcaaaatactcttaattgtga
ttagtaatcatgttcgggcaagttacgttgtgtataattaatttgacttaatcagataaa
aaaacaaatggacgcaagccggttggtatagatatcactggcctgtagaatatgtggttt
ttcacgtttaaataaaagctagctactatattatatttagtcttttttttttcttaaaccc
atttaacgtgatttattgactgtgaaacatgtttccacacacaggcttagaaactcctcg
caactaacatctccaaaatttgactatttatttatgaagataattcatctatgatgttca
actctattatatatgtatcatcgcagtattaagaattataatagtcaaatatagaagt
atatcgggtaaatgtagttgcatgtgcgacctgtttcgtgtaaaatgcttattctatata
gcttttttattggaaaataacgatgaactaaaaacgaaagggtatcatatagtttgact
tttatgttagagagagacatcttaatttggtcatatgttaaataattaattacaatgcat
acacaaatatttatgccatatctaaaaaatgataaaatatcataggtatactcaactata
tgatatccccataacagaaattgtacttttcttcaggcaatgaacttaacatttctgttt
gctaaaaacaaacatccacttaaagtggttcaacatatttatgtaataatttacagGGAG
                                                         G  G
GAGGTCCAGGATGGCCAGTTCCATTAGGAAGAAGGGACAGCTTAACAGCAAACCGAACCC
   G  P  G  W  P  V  P  L  G  R  R  D  S  L  T  A  N  R  T  L
TTGCAAATCAAAACCTTCCAGCACCTTTCTTCAACCTCACTCAACTTAAAGCTTCCTTTG
   A  N  Q  L  P  A  P  F  F  N  L  T  Q  L  K  A  S  F  A
CTGTTCAAGGTCTCAACACCCTTGATTTAGTTACACTCTCAGgtatacataatcaatttt
   V  Q  G  L  N  T  L  D  L  V  T  L  S  G
ttatttgctattagctagcaataaaaagtctctgatacagacatatttagataaattaat
ttctccataaacatttataataaaattatcaatttatgtacttaaaaattatggattgaa
gctcttttcatccaactttttactaaagttaaggtgcatataatataaaataaactatctc
ttgtttcttataaaagattgaagataagttaaagtctacttataaatcattaatatatg
tatagGTGGTCATACGTTTGGAAGAGCTCGGTGCAGTACATTCATAAACCGATTATACAA
     G  H  T  F  G  R  A  R  C  S  T  F  I  N  R  L  Y  N
CTTCAGCAACACTGGAAACCCTGATCCAACTCAACAACATACTTAGAAGTATTGCG
 F  S  N  T  G  N  P  D  P  T  L  N  T  T  Y  L  E  V  L  R
TGCAAGATGCCCCCAGAATGCAACTGGGGATAACCTCACCAATTTGGACCTGAGCACACC
 A  R  C  P  Q  N  A  T  G  D  N  L  T  N  L  D  L  S  T  P
TGATCAATTTGACAACAGATACTACTCCAATCTTCTGCAGCTCAATGGCTTACTTCAGAG
 D  Q  F  D  N  R  Y  Y  S  N  L  L  Q  L  N  G  L  L  Q  S
TGACCAAGAACTTTTCTCCACTCCTGGTGCTGATACCATTCCCATTGTCAATAGCTTCAG
 D  Q  E  L  F  S  T  P  G  A  D  T  I  P  I  V  N  S  F  S
CAGTAACCAGAATACTTTCTTTTCCAACTTTAGAGTTTCAATGATAAAAATGGGTAATAT
 S  N  Q  N  T  F  F  S  N  F  R  V  S  M  I  K  M  G  N  I
TGGAGTGCTGACTGGGGATGAAGGAGAAATTCGCTTGCAATGTAATTTTGTGAATGGAGA
 G  V  L  T  G  D  E  G  E  I  R  L  Q  C  N  F  V  N  G  D
CTCGTTTGGATTAGCTAGTGTGGCGTCCAAAGATGCTAAACAAAAGCTTGTTGCTCAATC
 S  F  G  L  A  S  V  A  S  K  D  A  K  Q  K  L  V  A  Q  S
TAAAtaaaccaataattaatggggatgtgcatgctagctagcatgtaaaggcaaattagg
 K
ttgtaaacctctttgctagctatattgaaataaaccaaaggagtagtgtgcatgtcaatt
cgattttgccatgtacctcttggaata
```

Figure 16C2

|  | | Exon I | | Exon II | | Exon III | | Exon IV |
|---|---|---|---|---|---|---|---|---|
| *A. thaliana* | M | FVN/R | GCD | VT/II | A/SGG | ALS | GG/AH | SM |
| Horseradish | M | FVN/R | GCD | VT/VI | A/SGG | ALS | GGH | VN |
| Rice | M | FVN | GCD | VLF | SGG | VLS | GGH | VNS |
| *GmEPA1* | M | FVR | GCD | VAT | GGP | LLS | AHT | INS |
| *GmEPB1* | M | FVR | GCD | VFL | SGG | ALS | GHT | TAE |
| *GmEPC* | M | FVQ | GCD | SVL | GGG | TLS | GHT | GSK |
| Tomato | M | FVD | GCD | V/LAK | LGG | ALAGAH | | IG |
| Wheat | M | F | GCD | VVA | LGG | ALSGAH | | VN |

Figure 17

A.
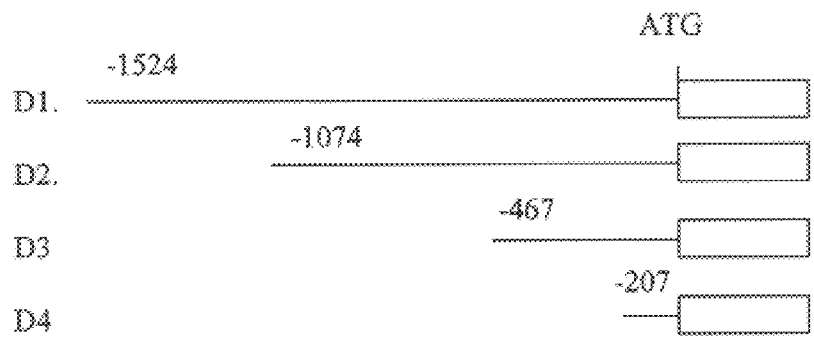
B.
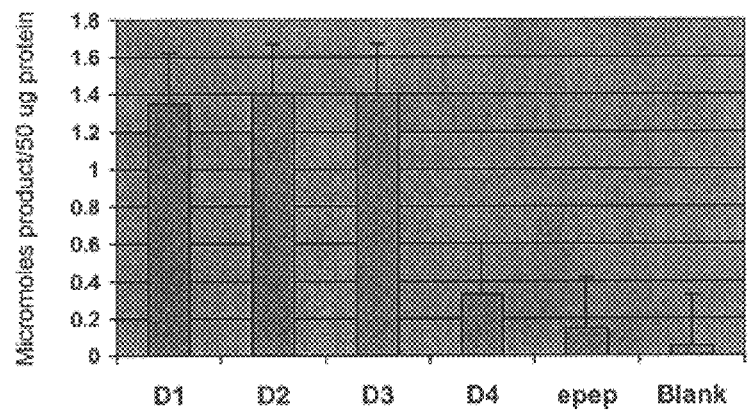
Figures 19

Seed coat
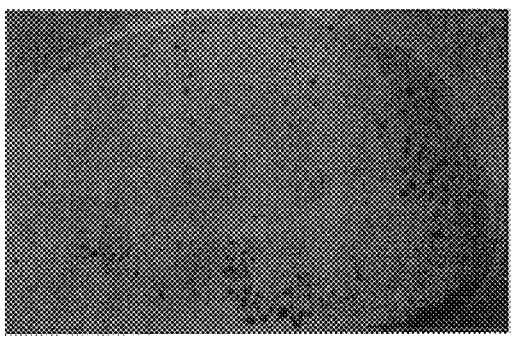
Root
Figures 20

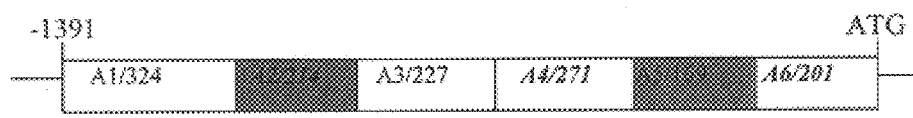
Promoter A1
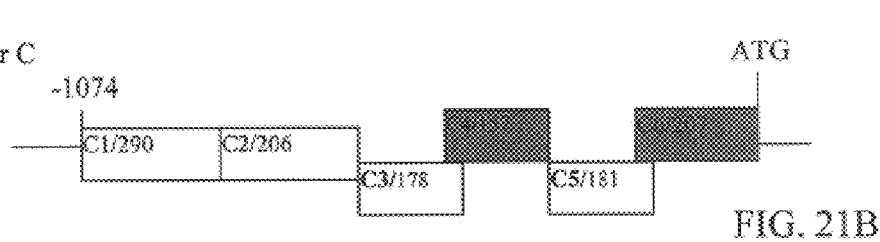
Promoter C
FIG. 21A
FIG. 21B
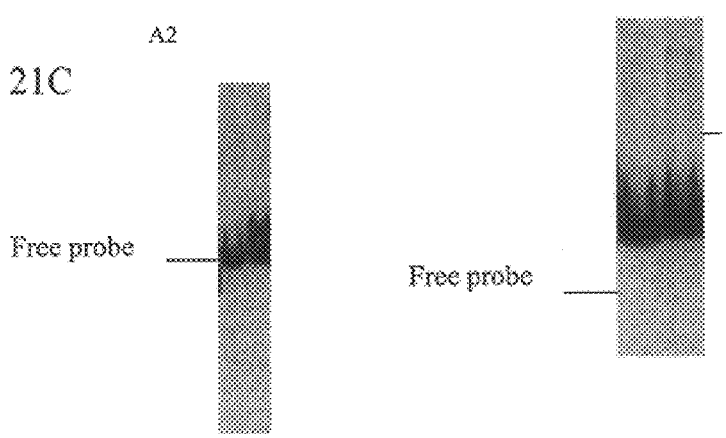
FIG. 21C
FIG. 21D

Genomic sequence of GC

```
   1  tagataaaaa aatgggatat aatttttctc agatgttgtt tatactgttt
  51  ttttaatcag aattaaaatt aatctttaat tatcgacata attttttttg
 101  gtgaatatta tcgacataat tatttaatac aaatttttat tgtacataga
 151  agtgatactt caatttttaat attggagaac agtacgaaaa cataaaaaaa
 201  ctgttattag aagaaaaaaa tatatggaaa aggttagcta catatattag
 251  ctaaattagt tgttctaatt ggctatataa accctattgt actctttgta
 301  atctcacctt tttcatttaa atacatttct acttttaag ttctatattt
 351  tctctcaatt ttcttcgata aaccatgaaa tttaacatgg tatatcagcg
 401  ataccaccca ctttgaaagc catgtatggc tagtatgggc agccaaaatt
 451  tgccctggtt caagcaaagc aagtgtttat atagatgtga cttttgttga
 501  ggaactcatg ccaatggtac tgattgtgaa actgagaaaa ctaatttgga
 551  gaatttgaat tatgatcatt aaatactcct ctcctgacta ccttcgtccc
 601  tcaaatttgt accatcatta tttcccaaaa atttgattac aatgcactaa
 651  ttaatgaatg tttcttacat tatcatatta tcatatctga cattttgttt
 701  ttactttta taataattat tttaaaaagt catacatgca aataattttt
 751  taatagttta cagttaaatt tttacagtaa aaatgcatga aaattaaact
 801  ttattttttcc aagtcatcat ttagtcaaat cccaaaacaa tgattatttt
 851  ttgcaaatga atgtttattg aacatttaaa tgtagcctaa ttaattctgg
 901  ttatggtgtc aatgttccaa aacctaatgc aagatcttag caagtacata
 951  catagatcta atttaaaact tatctttacg caagagatat aaagattata
1001  catctagttt taaacattaa cttttgtttt tgtgttaaaa aacagtaaca
1051  ttttcttaat tttgtagagt gacgtgctcc aaccatatta acgaagattt
1101  taattggtat tcaagttcat gaacttagta aataagtttt ggtcttcagt
1151  tttcaatttt cattacaaca tttatgtaaa atatcaacgt tttctgaaat
1201  ttgttgcttg tgtgctccaa ccacatttaa gagattatag aaattaattt
1251  tcaagaagat aagattccta ctcttgcctg gccctaccat agtacaataa
1301  atccactcat aaatcaacaa gtcgtcgtca taggcaattg ggcatcatat
1351  cataaacaat acgtacgtga tattatctag tgtctctcag tttactttat
1401  gagaaattat ttttctttaa aaaaagttaa ttaataaaaa catttgcgat
1451  accgtgagtt acaagaaatc cgccgaattc atctctataa ataaaaggat
1501  ctatatgaga ggtaaaatca tattaactca aaATGGGTTC CATGCGTCTA
1551  TTAGTAGTGG CATTGTTGTG TGCATTTGCT ATGCATGCAG GTTTTTCAGT
```

Figure 23A

1601 CTCTTATGCT CAGCTTACTC CTACGTTCTA CAGAGAAACA TGTCCAAATC
1651 TGTTCCCTAT TGTGTTTGGA GTAATCTTCG ATGCTTCTTT CACCGATCCC
1701 CGAATCGGGG CCAGTCTCAT GAGGCTTCAT TTTCATGATT GCTTTGTTCA
1751 Agtacgtact tttttttttc cttccaaaat gccctgcata tttaacaaga
1801 ttgctttgtt cacctagaaa aatgtgtttt tttcaacgat cttacgtacg
1851 tttgtttggt ttgaaaaata aatcagaaag agatcaagaa aatagctaga
1901 aagaaagcaa cgttttttta aaaggtattt agtgtgagaa aaatattaaa
1951 actgaagaga aagaaattaa ataagctttt cttgaatgat atttacatgt
2001 cttattaact taaagtcacc tttttctttt aagttgtgct tgaagaaaaa
2051 agatgtcttt cagtttagtt ttgattaatg ctaattatat ttttaattaa
2101 ttaattaata ctatatatct atttaccata ttaattatta ctatatttca
2151 tgatgacaac agacaagtat tctaaagagg tatcggtaga tgattaattt
2201 ttttataaaa aaatctttg cgtgtataga tattcttta taattggtgc
2251 agaaacttgt aatgctaatt gcaattaatc ttacattgat taactaatag
2301 ctataatcaa tatttaggtt aggtatagga gacaaatcaa gtgatctgaa
2351 caaattaagt tgttatattt gcattgtgac agGGTTGTGA TGGATCAGTT
2401 TTGCTGAACA ACACTGATAC AATAGAAAGC GAGCAAGATG CACTTCCAAA
2451 TATCAACTCA ATAAGAGGAT TGGACGTTGT CAATGACATC AAGACAGCGG
2501 TGGAAAATAG TTGTCCAGAC ACAGTTTCTT GTGCTGATAT TCTTGCTATT
2551 GCAGCTGAAA TAGCTTCTGT TCTGgtaatt ataactcct aattaattcc
2601 caaccattaa aaagttgcat gattggattc aaaattctat ggtattgggg
2651 ttctgatata aatttgtaat taaattgcac taaaaaaat tatcatatac
2701 ttttaataaa aaaaatttat ctaatttaat ttattattaa aactattttt
2751 aaaattcaat cctaactctt ttttaatcgg agcatgtaag ctggcaccca
2801 ccgtatatcg ttggaagatg ctataaaacc atttaattaa tggatggaat
2851 cagtcaaaac atttaattca aaatactctt aattgtgatt agtaatcatg
2901 ttcgggcaag ttacgttgtg tataattaat ttgacttaat cagataaaaa
2951 aacaaatgga cgcaagccgg ttggtataga tatcactggc ctgtagaata
3001 tgtggttttt cacgtttaaa taaaagctag ctactatatt atatttagtc
3051 tttttttttc ttaaacccat ttaacgtgat ttattgactg tgaaacatgt
3101 ttccacacac aggcttagaa actcctcgca actaacatct ccaaaatttg
3151 actatttatt tatgaagata attcatctat gatgttcaac tctattatat
3201 atatgtatca tcgcagtatt aagaattata atagtcaaat atagaagtat
3251 atcgggtaaa tgtagttgca tgtgcgacct gtttcgtgta aaatgcttat

Figure 23B 3301 tctatatagc ttttttattt ggaaaataac gatgaactaa aaacgaaagg
3351 gtatcatata gtttgactt tatgttagag agagacatct taatttggtc
3401 atatgttaaa taattaatta caatgcatac acaaatattt atgccatatc
3451 taaaaaatga taaaatatca taggtatact caactatatg atatccccat
3501 aacagaaatt gtacttttct tcaggcaatg aacttaacat ttctgtttgc
3551 taaaaacaaa catccactta aagtggttca acatatttat gtaataattt
3601 acagGGAGGA GGTCCAGGAT GGCCAGTTCC ATTAGGAAGA AGGGACAGCT
3651 TAACAGCAAA CCGAACCCTT GCAAATCAAA ACCTTCCAGC ACCTTTCTTC
3701 AACCTCACTC AACTTAAAGC TTCCTTTGCT GTTCAAGGTC TCAACACCCT
3751 TGATTTAGTT ACACTCTCAG gtatacataa tcaattttt atttgctatt
3801 agctagcaat aaaaagtctc tgatacagac atatttagat aaattaattt
3851 ctccataaac atttataata aaattatcaa tttatgtact taaaaattat
3901 ggattgaagc tcttttcatc caacttttac taaagttaag gtgcatataa
3951 tataaaataa actatctctt gtttcttata aaagattga agataagtta
4001 aagtctactt ataaatcatt aatatatgta tagGTGGTCA TACGTTTGGA
4051 AGAGCTCGGT GCAGTACATT CATAAACCGA TTATACAACT TCAGCAACAC
4101 TGGAAACCCT GATCCAACTC TGAACACAAC ATACTTAGAA GTATTGCGTG
4151 CAAGATGCCC CCAGAATGCA ACTGGGGATA ACCTCACCAA TTTGGACCTG
4201 AGCACACCTG ATCAATTTGA CAACAGATAC TACTCCAATC TTCTGCAGCT
4251 CAATGGCTTA CTTCAGAGTG ACCAAGAACT TTTCTCCACT CCTGGTGCTG
4301 ATACCATTCC CATTGTCAAT AGCTTCAGCA GTAACCAGAA TACTTTCTTT
4351 TCCAACTTTA GAGTTTCAAT GATAAAAATG GGTAATATTG GAGTGCTGAC
4401 TGGGGATGAA GGAGAAATTC GCTTGCAATG TAATTTTGTG AATGGAGACT
4451 CGTTTGGATT AGCTAGTGTG GCGTCCAAAG ATGCTAAACA AAAGCTTGTT
4501 GCTCAATCTA AAtaaaccaa taattaatgg ggatgtgcat gctagctagc
4551 atgtaaaggc aaattaggtt gtaaacctct tgctagcta tattgaaata
4601 aaccaaagga gtagtgtgca tgtcaattcg attttgccat gtacctcttg
4651 gaata

Figure 23C

```
ATGGGTTCCATGCGTCTATTAGTAGTGGCATTGTTGTGTGCATTTGCTATGCATGCAGGTTTTTCAGTCTCTTATGCTCA
GCTTACTCCTACGTTCTACAGAGAAACATGTCCAAATCTGTTCCCTATTGTGTTTGGAGTAATCTTCGATGCTTCTTTCA
CCGATCCCCGAATCGGGGCCAGTCTCATGAGGCTTCATTTTCATGATTGCTTTGTTCAAGGTTGTGATGGATCAGTTTTG
CTGAACAACACTGATACAATAGAAAGCGAGCAAGATGCACTTCCAAATATCAACTCAATAAGAGGATTGGACGTTGTCAA
TGACATCAAGACAGCGGTGGAAAATAGTTGTCCAGACACAGTTTCTTGTGCTGATATTCTTGCTATTGCAGCTGAAATAG
CTTCTGTTCTGGGAGGAGGTCCAGGATGGCCAGTTCCATTAGGAAGAAGGGACAGCTTAACAGCAAACCGAACCCTTGCA
AATCAAAACCTTCCAGCACCTTTCTTCAACCTCACTCAACTTAAAGCTTCCTTTGCTGTTCAAGGTCTCAACACCCTTGA
TTTAGTTACACTCTCAGGTGGTCATACGTTTGGAAGAGCTCGGTGCAGTACATTCATAAACCGATTATACAACTTCAGCA
ACACTGGAAACCCTGATCCAACTCTGAACACAACATACTTAGAAGTATTGCGTGCAAGATGCCCCCAGAATGCAACTGGG
GATAACCTCACCAATTTGGACCTGAGCACACCTGATCAATTTGACAACAGATACTACTCCAATCTTCTGCAGCTCAATGG
CTTACTTCAGAGTGACCAAGAACTTTTCTCCACTCCTGGTGCTGATACCATTCCCATTGTCAATAGCTTCAGCAGTAACC
AGAATACTTTCTTTTCCAACTTTAGAGTTTCAATGATAAAAATGGGTAATATTGGAGTGCTGACTGGGGATGAAGGAGAA
ATTCGCTTGCAATGTAATTTTGTGAATGGAGACTCGTTTGGATTAGCTAGTGTGGCGTCCAAAGATGCTAAACAAAGCT
TGTTGCTCAATCTAAA
```

SOYBEAN PEROXIDASE GENE FAMILY AND AN ASSAY FOR DETECTING SOYBEAN PEROXIDASE ACTIVITY

CROSS-REFERENCE TO RELATED APPLICATION

The present application is a continuation-in-part application of application Ser. No. 08/868,577, filed Jun. 4, 1997, now U.S. Pat. No. 5,866,695, which is a continuation-in-part of Ser. No. 08/671,320, filed Oct. 27, 1995, now U.S. Pat. No. 5,840,558.

BACKGROUND OF THE INVENTION

The present invention relates to the DNA sequences of the soybean peroxidase, and to the enzymatic assay of peroxidase activity. The invention further relates to the use of soybean peroxidase in immunoassays or oligonucleotide detection. The invention also relates to medical, environmental diagnostics and generally to oligonucleotides employing anti-soybean peroxidase monoclonal antibody. In addition, the present invention is directed to a promoter and regulatory sequences within the promoter. The present invention is also directed to DNA molecules including one or more of said regulatory sequences or full length promoter, such as a DNA construct comprising the regulatory region or full length promoter operably linked to one or more genes or antisense DNA. The invention is further directed to transformed plant tissue including the DNA molecule and to transformed plants and seeds thereof.

The publications and other materials used herein to illuminate the background of the invention or provide additional details respecting the practice of the invention, are incorporated by reference, and for convenience are respectively grouped in the appended list of references.

Function of Peroxidase in Biological Systems

Peroxidase is a class of proteins whose primary function is to oxidize a variety of hydrogen donors at the expense of peroxide or molecular oxygen. Areas where peroxidase could have an immediate use are: pulp and paper bleaching; on-site waste destruction; soil remediation; organic synthesis; and diagnostic chemistries.

At present, pulp and paper is bleached using chloride ions as a chemical agent. Soybean peroxidase has several advantages over chlorine bleach: lower cost; environmentally friendly; and hydroxyl ions produced by peroxidase have twice the oxidation power of chlorine ions.

In waste water and soil treatments, peroxidase has advantages since many organic compounds are toxic, inhibitory, or refractory to microbes, and certain organic compounds may result in the production of microbial products that produce toxic or offensive effluent.

The use of oxidation to achieve on-site destruction or detoxification of contaminated water and waste will increase in the future. If carried out to its ultimate stage, oxidation can completely oxidize organic compounds to carbon dioxide, water and salts.

Peroxidase has several uses in organic synthesis. Using peroxidase, researchers synthesized conductive polyaniline that produced only water as a by-product. Peroxidase can also be used in the manufacturing of adhesive and antioxidant intermediates.

Enzymes are now widely used in medical and environmental diagnostics. Horseradish peroxidase has been one of the most satisfactory enzymes but is relatively expensive. It has now been found that soybean peroxidase can be readily harvested from soybean hulls at minimal expense and be substituted for horseradish peroxidase in these diagnostic chemistries.

Several diagnostic chemistries using the enzymatic activity of horseradish peroxidase and polyclonal antibodies have been described in the literature. Horseradish peroxidase has been used for diagnostic determinations of various analytes and has been used as a label in enzyme labeled antibodies used in the determination of immunologically reactive species (i.e., immunoassays). Such determinations can be carried out in solution or in dry analytical elements.

One type of useful assay utilizes enzymatic reactions wherein the analyte, upon contact with the appropriate reagents, reacts with oxygen in the presence of a suitable enzyme to produce hydrogen peroxide in proportion to the concentration of the analyte. A detectable product such as a visible or fluorescent dye is then produced by the reaction of hydrogen peroxide in proportion to the concentration of the analyte in the tested liquids. Peroxidase is generally used in such assays to catalyze the oxidation of the interactive composition by hydrogen peroxide. One example of such an assay is a glucose assay using glucose oxidase. Glucose is oxidized in the presence of oxygen by the enzyme, glucose oxidase, to produce glucolactone and hydrogen peroxide. In the presence of peroxidase, the hydrogen peroxide oxidizes a colorless dye such as tetramethylbenzidine to produce a colored product.

Another type of assay utilizes an immunologically reactive compound such as an antibody. These chemistries can be generally classified into two groups, namely, conjugate or enzyme labeled antibody procedures, and non-conjugate or unlabeled antibody procedures. In the conjugate procedures, the enzyme is covalently linked to the antibody and applied to a sample containing the immobilized antigen to be detected. Thereafter the enzyme substrate, e.g., hydrogen peroxide, and an oxidizable chromogen such as a leuco dye are applied. In the presence of the peroxidase, the peroxide reacts with the chromogen resulting in the production of color. The production of color indicates the presence and in some cases the amount of the antigen. In another method, a competing substance is used to dislodge an antibody enzyme conjugate from an immobilized substrate, leading to an absence of color.

In a method sometimes referred to as the sandwich assay or enzyme linked immunosorbent assay (ELISA), a first antibody is bound to a solid support surface and contacted with a fluid sample suspected to contain the antigen to be detected and an enzyme-antibody conjugate. The antigen complexes with the antibody and the conjugate bonds to the antigen. Subsequent introduction of the substrate and chromogen produces a visual indication of the presence of the antigen.

Procedures employing non-conjugated enzymes include the enzyme bridge method and the peroxidase-antiperoxidase method. These methods use an antiperoxidase antibody produced by injecting peroxidase into an animal such as a goat, rabbit or guinea pig. The method does not require chemical conjugation of the antibody to the enzyme but consists of binding the enzyme to the antigen through the antigen-antibody reaction of an immunoglobulin-enzyme bridge. In the enzyme bridge method a secondary antibody acts as an immunologic bridge between the primary antibody against the suspected antigen and the antiperoxidase antibody. The antiperoxidase antibody in turn binds the peroxidase which catalyzes the indicator reaction. In the peroxidase-antiperoxidase method, a complex of the peroxidase and the antiperoxidase antibody is formed. This complex can then be used in the immunologic bridge method.

Though peroxidase genes from different biologic sources have been identified, including other plant peroxidase genes from horseradish, tomato, pea, arabidopsis, peanut and turnip, and bacterial lignin peroxidase gene, there have not been any reports regarding identification of peroxidase genes from soybean.

Soybean coats are abundant and inexpensive, making them an excellent source of peroxidase. Therefore, there is substantial interest in cloning soybean peroxidase genes which will open the possibility of characterization of the expression patterns of individual peroxidase isoforms during normal plant development and genetic and molecular manipulations for increased peroxidase activity.

Regulation of Transcription and Translation

Eukaryotic genes consist of a transcription/translation initiation region, a coding region and a termination region. The transcription/translation initiation region is typically located upstream of the coding region, or in other words, entirely to the 5' terminal end of the coding region. This initiation region includes a "promoter" region, which contains the signals for RNA polymerase to begin transcription so that synthesis of the coded protein can proceed. In addition, there are "untranslated sequences" responsible for binding to ribosomes and translation initiation. The translation-related regions of these "upstream" regulatory sequences vary in length and base composition from gene to gene and may be comprised of 100 bp or as much as 1 kbp.

The characteristics of the promoter will determine the level, tissue specificity and timing of transcription. Eukaryotic promoters are complex and are comprised of components which include a "TATA box" at about 35 bp 5' relative to the transcription start site. Further upstream, there can be a promoter element with homology to the consensus sequence CCAAT which, in plants, may be substituted by a consensus sequence which Messing et al. (1983) have termed the AGGA box. Additional DNA sequences in the 5' untranslated region are believed to be involved in the modulation of gene expression. These include DNA sequences which control gene expression in a tissue-specific manner.

Through recombinant techniques, a plant transcription/translation initiation region can be designed to activate expression, by plant tissue, of a nucleic acid sequence of interest, such as a DNA sequence encoding a heterologous or non-naturally occurring gene. By modifying the promoter region of a construct capable of expression in a plant, the timing, tissue specificity and level of expression of transcription can be regulated.

The analysis of promoter-reporter gene fusions is one of the most widely used direct approaches to identify sequences that control the transcriptional regulation of plant genes. Regulatory elements that are involved in tissue-specific and/or developmentally regulated expression have been identified in many plant gene promoters (Mohan et al., 1993; Raghothama et al., 1993; Intapruk et al., 1994; Hatton et al., 1995; Sieburth and Meyerowitz, 1997). Gel retardation and DNA footprinting assays also have been used to study the transcriptional regulation of plant genes. Many nuclear proteins that bind to promoter fragments have been identified and genes encoding for these nuclear proteins have been isolated (Katagiri et al., 1989; Kawaoka et al., 1994; Zhao and Okita, 1995; Liu et al., 1998).

Peroxidase genes have been isolated from *Arabidopsis thaliana* (Intapruk et al., 1991), horseradish (Fujiyama et al., 1988 and 1990), tomato (Roberts and Kolattukudy, 1989), rice and wheat (Baga et al., 1995). Despite the role that plant peroxidases play in plant physiology, the regulatory mechanisms controlling peroxidase gene expression are not well understood. Little is known about the signaling factors or the DNA sequences that control peroxidase gene expression. Hormonal regulation of peroxidase gene expression has been reported in callus tissue, where the anionic peroxidases of potato and tomato were induced by abscisic acid at the transcriptional level (Roberts and Kolaftukudy, 1989). Lagrimini et al. (1991, 1996) demonstrated the importance of proper peroxidase regulation by over-expression and under-expression of an anionic peroxidase in tobacco, which in both cases resulted in aberrant phenotypes of the transgenic plants. Kawaoka et al. (1994) found that one transacting factor that interacts with a G-box element was essential for wound-induced expression of a horseradish peroxidase promoter. Intapruk et al. (1994) reported that multiple cis-elements in the horseradish peroxidase prxEa promoter were involved in regulating transcription of this peroxidase gene.

Recombinant Protein Technology

Recombinant protein technology has expanded to include protein production on a small scale for research purposes as well as large scale production processes for recombinant therapeutic proteins. The development of different protein expression systems reflects the variety of applications for their expressed products and the different features and functions of each. Many current production processes, such as cell culture and fermentation, are limited by poor yield, transient expression, poor folding and post-translational modification, costly manufacture, short shelf life and unpredictable immunogenic response.

Biotechnologists are starting to realize that higher organisms may be the most efficient hosts for production of recombinant proteins. The rapid progress made in development of cloning vectors for plants and animals has been allied with similar advances in cell culture systems for higher organisms. However, neither animal nor plant cells respond well to being suspended in culture media and therefore will attach to available solid support. The resulting cultures have much longer generation times than microbial cultures, limiting the yield of recombinant protein that can be obtained.

Another approach to production of recombinant protein is one that makes use of an intact organism rather than a cell culture. Examples of some methods known in the art for transformation of plant cells include: transformation via *Agrobacterium tumefaciens*, electroporation, microinjection and bombardment with DNA coated particles.

Within the plant biotechnology sector, there is great interest in expressing mammalian proteins in plants in a commercially feasible manner. One of the most important factors to be considered in developing a plant transformation procedure for production of recombinant proteins in plants is the availability of a promoter which provides expression in a tissue-specific manner. For example, for the transformation of plants with DNA encoding therapeutic proteins or vaccines, it is clearly desirable to obtain expression of the introduced gene in a tissue from which the protein product is readily recovered substantially free of other tissues.

The seeds of higher plants are very efficient at protein systhesis, as they accumulate large quantities of storage proteins and other compounds that the young seedling uses as a nutrient supply during the early stages of germination. Many crop plants have been bred specifically for the protein content of their seeds and the genes involved in seed development are quite well understood. If a gene for a natural seed protein is replaced by a gene coding for some useful foreign protein, the foreign protein may accumulate in the seeds. This has been demonstrated by the synthesis of pharmaceutical compounds called enkephalins in the seeds of engineered oilseed rape plants. Enkephalins are small proteins, only a few amino acids in length, and it has yet to be established that larger foreign proteins can be synthesized efficiently in the special environment found within the developing seed. Further success in this area would open up an exciting new area of biotechnology.

BRIEF DESCRIPTION OF THE DRAWINGS

FIG. 5 Comparisons of nucleotide sequences of the coding regions of the GmEPa1 (SEQ ID NO:18) and GmEPa2 (SEQ ID NO:12) genes and the predicted amino acid sequences of GmEPa1 (p1) (SEQ ID NO:11) and GmEPa2 (p2) (SEQ ID NO:13). Amino acid sequences are shown using the single-letter code. The complete coding and predicted amino acid sequences are given only for GmEPa1 (first and third lines, respectively). To emphasize the similarity between the two genes and their products, only those nucleotides in the coding region of GmEPa2 and the predicted amino acid that differ from the corresponding ones in GmEPa1 and p1 are shown. The dots indicate identity of nucleotides and amino acids. For example, a dot under a nucleotide represents the presence of the same nucleotide that is directly above the dot. The signal peptide is shown in bold italics. The start of the mature proteins begins with the [QLXXXFY] motif at position 1. The cysteine residues in disulfide bridges are shaded. Conserved amino acid areas are outlines.

FIG. 6 Comparisons of the nucleotide sequences of the coding regions of the GmEPb1 (SEQ ID NO:14) and GmEPb2 (SEQ ID NO:16) genes and the predicted amino acid sequences of GmEPb1 (p3) (SEQ ID NO:15) and GmEPb2 (p4) (SEQ ID NO:17). Amino acid sequences are shown using the single-lefter code. The complete coding and predicted amino acid sequences are given only for GmEPb1 (first and third lines, respectively). The dots indicate identity of nucleotides and amino acids. The asterisks indicate the gap of nucleotides and amino acids between GmEPb1 and GmEPb2, p3 and p3, respectively. The cysteine residues are shaded and the conserved amino acid areas are outlines. For example, a dot under a nucleotide represents the presence of the same nucleotide that is directly above the dot. The signal peptide is shown in bold italics.

FIG. 13 Immunoblot showing transfer of fetuin to immunlon paper in an immunoblotting procedures using fetuin and MM4 antibody.

FIGS. 14A–C Genomic DNA sequence for GmEPa1 (SEQ ID NO:18) with the ATG start codon underlined.

FIGS. 15A–B Genomic DNA sequence for GmEPb1 (SEQ ID NO:19) with the ATG start codon underlined.

FIGS. 16A–C Nucleotide and deduced amino acid sequences of GmEPA1 (SEQ ID NO:11), GmEPB1 (SEQ ID NO:15) and GmEPC (SEQ ID NO:22), respectively. Untranslated sequences (lowercase), ORF (uppercase), deduced amino acid sequence (below ORF in single letter code), putative TATA box and CAAT box (shaded), direct repeats (outlined) and putative polyadenylatron signals (bold face).

FIG. 17 Comparison of gene structures between soybean peroxidase and other plant peroxidases. Introns shown as bold rectangles.

FIGS. 19A–B Promoter deletion analysis of GmEPC. Peroxidase activity measured using tetramethyl-benzadine as substrate and read at $OD_{405}$ (FIG. 19A). Deletions D1, D2, D3 and D4 (FIG. 19B) were from long-range PCR and full length peroxidase gene. 3' UTR and primers were synthesized.

FIGS. 20A–B Transient assay of GUS activity in seed coat (FIG. 20A) and root (FIG. 20B) after bombardment by Construct A (Table 2).

FIG. 21A–D Gel-retardation assays of GmEPAI (FIG. 21C) and GmEPC (FIG. 21 D) promoter fragments (FIGS. 21A and B, respectively) showing DNA-protein complexes. Assays included non-specific DNA competitors and controls with no nuclear extract (+).

FIGS. 23A–C Genomic DNA sequence for GmEPC (SEQ ID NO:20) with the ATG start codon underlined.

FIG. 25 cDNA nucleic acid sequence for GmEPc (SEQ ID NO:21).

FIG. 26 Amino acid sequence for the protein product of GmEPc (SEQ ID NO:22).

SUMMARY OF SEQUENCE LISTING

Figure 1:
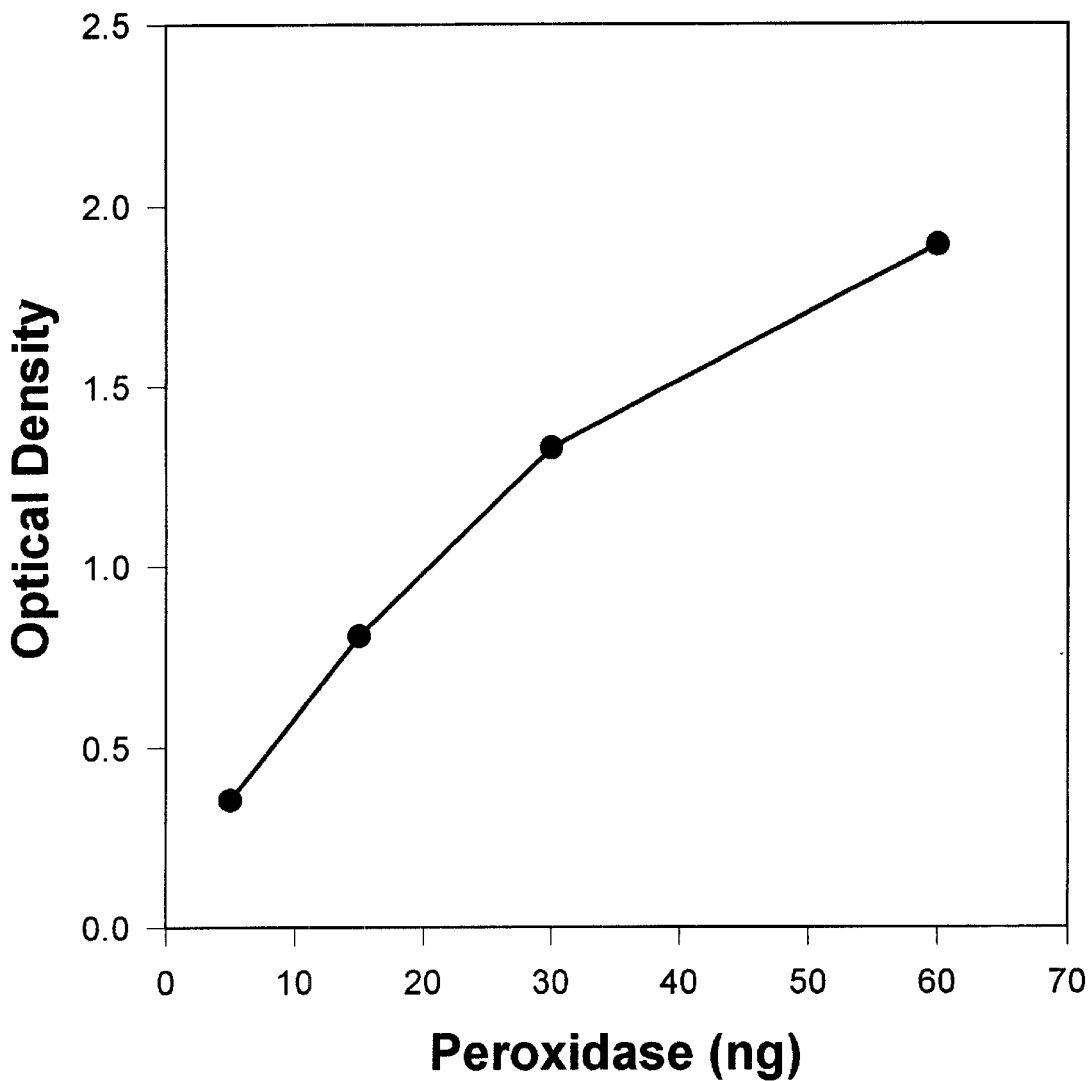
FIG. 1 Average ELISA absorbance (405 nm) of purified peroxidase samples against 1:10 dilution of peroxidase monoclonal antibodies (MAB).

SEQ ID NO:1 is, the conserved amino acid sequence used to generate a plant peroxidase specific primer (PSP).

SEQ ID NO:2 is the nucleotide sequence for PSP.

SEQ ID NO:3 is the nucleotide sequence for the primer used to study expression pattern of GmEPa1.

SEQ ID NO:4 is the nucleotide sequence for the primer used to study expression pattern of GmEPa2.

SEQ ID NO:5 is the nucleotide sequence for the primer used to study expression pattern of GmEPb1.

SEQ ID NO:6 is the nucleotide sequence for the primer used to study expression pattern of GmEPb2.

SEQ ID NO:7 is the amino acid sequence for the $NH_2$ terminus motif of GmEPa1 and GmEPa2.

SEQ ID NO:8 is the amino acid sequence for the putative polyadenylation signal.

SEQ ID NO:9 is the amino acid sequence of a 100% conserved subdomain in plant peroxidases.

SEQ ID NO:10 is the cDNA nucleic acid sequence for GmEPa1.

SEQ ID NO:11 is the amino acid sequence for the protein product of GmEPa1.

SEQ ID NO:12 is the cDNA nucleic acid sequence for GmEPa2.

SEQ ID NO:13 is the amino acid sequence for the protein product of GmEPa2.

SEQ ID NO:14 is the cDNA nucleic acid sequence for GmEPb1.

SEQ ID NO:15 is the amino acid sequence for the protein product of GmEPb1.

SEQ ID NO:16 is the cDNA nucleic acid sequence for GmEPb2.

SEQ ID NO:17 is the amino acid sequence for the protein product of GmEPb2.

SEQ ID NO:18 is the genomic nucleic acid sequence for GmEPa1.

SEQ ID NO:19 is the genomic nucleic acid sequence for GmEPb1.

SEQ ID NO:20 is the genomic nucleic acid sequence for GmEPc.

SEQ ID NO:21 is the cDNA nucleic acid sequence for GmEPc.

SEQ ID NO:22 is the amino acid sequence for the protein product of GmEPc.

SUMMARY OF THE INVENTION

The present invention involves isolated DNA sequences representing a soybean peroxidase gene family. The DNA sequences of the present invention encode amino acids that show homology to other plant peroxidase conserved amino acid regions. Outside the conserved regions the sequences show a high degree of divergence from other plant peroxidases. These peroxidases can be used in immunoassays and oligonucleotide assays.

The method of the present invention further relates to a direct immunoassay method without the secondary enzyme-linked antibody as used in reaction found in ELISA.

The invention also relates to a kit for measuring peroxidase activity outside the laboratory to determine the effect of environment and seed storage on peroxidase activity, and allows direct selection of high peroxidase genotypes in a plant breeding field, grain elevator and processing plant. The kit also allows quantitation and monitoring of peroxidase activity in processes using peroxidase or peroxidase solutions, such as pulp and paper bleaching, on-site waste destruction, soil remediation and organic synthesis.

The present invention also relates to an anti-soybean peroxidase antibody which does not inhibit peroxidase activity which can be used in conventional immunoassays, including but not limited to the following: enzyme capture assay for activity quantification; ELISA for peroxidase concentration; soybean peroxidase capture assay (SPCA) kits for measuring activity outside the lab; ELISA kits for measuring concentration outside the lab; peroxidase-antiperoxidase conjugates; immunohistochemical detection; immunoperoxidase microscopy and immunopurification of peroxidase. The anti-soybean peroxidase antibody is also useful in the immunoassays of the present invention and in assays for oligonucleotides.

The peroxidase-antiperoxidase conjugates of the present invention are useful in the following applications: non-radioactive nucleic acid labeling and detection; conjugating antibody complex in western blot; ELISA reactions; ELISA detection of DNA and RNA; and conjugate to polymerase chain reaction (PCR) products.

The present invention also relates to an immunoassay in which three antibodies are utilized and none of the antibodies are conjugated to an enzyme. The first antibody is specific for the target antigen. The second antibody is an anti-antibody which binds to the first antibody and a third antibody. The third antibody is specific for soybean peroxidase. The third antibody captures soybean peroxidase from a peroxidase solution, eliminating the need to conjugate soybean peroxidase to an antibody and insuring maximal peroxidase activity.

The present invention further relates to isolation of genomic DNA of soybean peroxidases. The genomic sequences include the promoter region and the coding region of the particular soybean peroxidase. The soybean peroxidase promoters can be used for preparing transgenic plants, especially transgenic soybeans.

A further object of the invention relates to the field of plant molecular biology in general and in particular to regulatory sequences and their recombined arrangement within a promoter region such that expression of an operably linked gene or antisense DNA in transformed plants is regulated. This invention also enables regulation of expression of desirable heterologous genes in plants. In the preferred embodiment, regulator sequences are derived from the upstream region of the soybean peroxidase gene.

DETAILED DESCRIPTION OF THE INVENTION

The present invention relates to immunoassays or oligouncleotide assays which utilize soybean peroxidase as a marker. The invention further relates to the use of a third antibody, an anti-soybean peroxidase antibody, in immunoassays. Soybean peroxidase may be bound to the anti-soybean peroxidase antibody prior to binding of this antibody with the second antibody (anti-antibody) in the assay. Alternatively, the anti-soybean peroxidase antibody is bound to the second antibody (anti-antibody) and then the soybean peroxidase bound by its specific antibody.

A further object of the invention relates to the field of plant molecular biology in general and in particular to regulatory sequences and their recombined arrangement within a promoter region such that expression is regulated. This invention enables regulation of expression of desirable heterologous genes in plants. In the preferred embodiment, regulator sequences are derived from the upstream region of the soybean peroxidase gene. The present invention also relates to the genomic DNA and promoters of soybean peroxidases and their use as promoters for producing transgenic plants, including transgenic soybeans.

In order to provide an understanding of several of the terms used in the specification and claims, the following definitions are provided:

"Encode." A polynucleotide is said to "encode" a polypeptide if, in its native state or when manipulated by methods well known to those skilled in the art, it can be transcribed and/or translated to produce the RNA for and/or the polypeptide or a fragment thereof. The anti-sense strand is the complement of such a nucleic acid and the encoding sequence can be deduced therefrom.

"Expression" refers to the transcription and translation of a structural gene so that a protein is synthesized.

"GmEP" refers to cDNA or genomic DNA for peroxidase from Glycine max. cv. Resnick. GmEP has sometimes been referred to herein as "SEP."

"GmEP" refers to the protein product of GmEP gene. GmEP has sometimes been referred to herein as "SEP".

"isolated", "substantially pure" and "substantially homogeneous"—These terms are used int describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95% w/w, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art for purification utilized.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"nondestructive"—The term nondestructive refers to the ability of quantitating peroxidase activity without killing the seed, plant or rendering peroxidase non-enzymatically active.

"Operably linked"—The term operably linked refers to a juxtaposition wherein the components so described are in a relationship permitting them to function in their intended manner, i.e., a promoter is operably linked to a coding sequence if the promoter affects its transcription or expression.

"Plant tissue" includes differentiated and undifferentiated tissues of plants, including, but not limited to, roots, shoots, leaves, pollen, seeds, tumor tissue and various forms of cells in culture, such as single cells, protoplasts, embryos and callus tissue. The plant tissue may be in planta or in organ, tissue or cell culture.

As used herein, a "portion" of the peroxidase promoter regions defined as having a minimal size of at least about 8 nucleotides, or preferably about 15 nucleotides, or more preferably at least about 25 nucleotides, and may have a minimal size of at least about 40 nucleotides. The present invention includes all novel nucleic acids having at least 8 nucleotides derived from SEQ ID NOS:18, 19 or 20, its complement or functionally equivalent nucleic acid sequences. The present invention includes all nucleic acids having at least 8 nucleotides derived from SEQ ID NOS:18, 19 or 20 with the proviso that it does not include nucleic acids existing in the prior art.

A "promoter" refers to the sequences at the 5' end of a structural gene which direct the initiation of transcription. Promoter sequences are necessary, but not always sufficient, to drive the expression of a downstream gene. Eukaryotic promoters generally contain a sequence with homology to the consensus 5'-TATAAT-3' (TATA box) about 10–35 bp 5' to the transcription start (cap) site, which is by convention numbered +1; bases 3' to the cap site are given positive numbers while bases 5' to the cap site receive negative numbers reflecting their distances from the cap site. About 30–70 bp 5' to the TATA box, there is often another promoter component with homology to the canonical form 5'-CCAAT-3' (R. Breathnach and P. Chambon (1981) Ann. Rev. Biochem. 50:349–393). In plants, the CCMT 'box' is sometimes replaced by the AGGA 'box' (Messing et al. (1983) in *Genetic Engineering of Plants,* T. Kosuge et al. (eds.), Plenum Press, Pp. 211–227). Other sequences conferring tissue specificity, response to environmental signals or maximum efficiency of transcription may be found interspersed with these promoter elements or found further in the 5' direction from the cap site. Such sequences are often found within 400 bp of the cap site, but may extend as far as 1000 bp or more.

A truncated promoter refers to the TATA box region comprising proximal sequences necessary for initiating transcription but excluding enhancer sequences.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory control" refers in general to the modulation of gene expression induced by DNA sequence elements, particularly those located upstream of (5' to) the transcription start site. Regulation may be analogous to an on/off switch which responds to environmental conditions or regulation may result in variations in the level of gene expression or its tissue specificity. Placing a structural gene under the regulatory control of a promoter or a regulatory sequence element means positioning the structural gene such that the expression of the gene is controlled by these sequences, i.e., operably linked. Promoters are generally positioned 5' (upstream) to the genes that they control. In the construction of heterologous promoter/structural gene combinations, it is generally preferred to position the promoter at a distance from the gene transcription start site that is approximately the same as the distance between the promoter and the gene it controls in its natural setting, i.e., the gene from which the promoter is derived. As is known in the art, some variation in this distance can be accommodated without loss of promoter function.

"Regulatory sequences" refers to those sequences which affect the expression of the gene (including transcription of the gene, and translation, splicing, stability or the like of the messenger RNA and tissue specificity). These sequences are normally within 100 kb of the coding region of a locus, although they may also be more distant from the coding region, "Substantial homology or similarity"—A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least doubt 14 nucleotide, preferably at least about 65%, more preferably at least about 75% and most preferably at least about 90%. See, Kanehisa, 1984. The length of homology comparison, as described, may be over longer stretches, and in certain embodiments will often be over a stretch of at least about nine nucleotide, usually at least about 20 nucleotide, more usually at least about 24 nucleotide, typically at least about 28 nucleotide, more typically at least about 32 nucleotide, and preferably at least about 36 or more nucleotide.

Nucleic acid hybridization will be affected by such conditions as salt concentration, temperature or organic solvents, in addition to the base composition, length of the complementary strands, and the number of nucleotide base mismatches between the hybridizing nucleic acids, as will be readily appreciated by those skilled in the art. Stringent temperate conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

A "structural gene" is that portion of a gene comprising a DNA segment encoding a protein, polypeptide or a portion thereof. The term can refer to copies of a structural gene naturally found within the cell, but artificially introduced, or the structural gene may encode a protein not normally found in the plant cell into which the gene is introduced, in which case it may be referred to as a heterologous gene.

"Substantially similar function" refers to the function of a modified nucleic acid with reference to the wild-type peroxidase nucleic acid The modified nucleic acid is prepared by conventional techniques and includes nucleic acids with a function substantially similar to the wild-type peroxidase gene.

The practice of the present invention employs, unless otherwise indicated, conventional techniques of chemistry, molecular biology, microbiology, recombinant DNA, genetics, immunology, manipulation of recombinant DNA in plant tissue and the culture and regeneration of transformed plants. See, e.g., Maniatis et a., 1982; Sambrook et al., 1989; Ausubel et al., 1992; Glover, 1985; Anand, 1992; Guthrie and Fink, 1991, which are expressly herein incorporated by reference.

The present invention is directed to a method of quantitating peroxidase activity, a kit for quantitating peroxidase activity, immunological assays, and DNA sequences regulating and representing a soybean peroxidase gene family.

The method of this invention is adaptable to both solution and dry assays and describes the capture of peroxidase by an antibody from a solution. Antibodies are immobilized on a solid support and unbound matrix is blocked with unreactive proteins. Solutions containing peroxidase are incubated with the immobilized antibodies and then removed. Captured peroxidase is then assayed for activity with any substrate, with or without additives, previously used in horseradish peroxidase assays. This invention does not use a secondary enzyme-linked antibody like an ELISA assay.

The method of this invention can also be practiced with a dry analytical element. The kit may be composed of an absorbent carrier material, e.g. a thin sheet of a self-supporting absorbent or bibulous material, such as filter paper or strips, which contains an immobilized antibody. The element can be divided into multiple zones with different compositions of the antibody incorporated into individual zones of the carrier material. Such elements are known as test strips, diagnostic elements, dip sticks, diagnostic agents and the like.

The assay or test kit can be used to quantitate peroxidase activity in plant fluids from macerated tissue with or without exogenous liquid added. Such fluids include, but are not limited to, fluids from leaves, stems, roots, flowers, seeds, seed coats, embryos, hypocotyls, coleoptiles, seed pods and seed buds. It is also possible to assay fluids from a variety of plant species including, but not limited to, soybean, corn, wheat, sorghum and oats.

This invention allows for the selection of high peroxidase plant genotypes in the field of plant breeding. Since minimal amounts of tissue are needed, unlike other methods of assaying peroxidase activity, e.g. Gilliken and Graham, Plant Physiol. 96:214–220 (1991), this invention is non-destructive to the seed or resulting plant. This greatly accelerates the progress of plant breeding for high peroxidase levels. The non-destructive nature allows high peroxidase plant genotypes to be selected and advanced to the next generation. The non-destructive nature of the assay is unique. In addition to the non-destructive nature of the assay, another unique trait of the present invention is the quantitative nature of the assay. Being quantitative, the present invention allows for the ultimate discriminatory assay for the separation of high peroxidase genotypes. Previous assays are not able to separate high peroxidase genotypes, e.g. Buttery & Buzzell, Crop Science 8:722–725 (1968). The ranking of high peroxidase genotypes, based on activity, will allow for the most efficient selection for high peroxidase genotypes. This invention is unique in that it is the only method that is non-destructive to the seed or plant and also is quantitative.

The assay or kit can be used to monitor peroxidase activity in industrial processes and is an identity preserved system to deliver high peroxidase plant material to processors. In an identity preserved system, kits will be used to identify high peroxidase seeds or to monitor activity from the seed company, to the farmers field, grain elevator, grain truck and finally to the processing facility. The kit also can be used to monitor peroxidase activity in stored peroxidase solutions. In industrial processes that use peroxidase, the kit can be used to monitor peroxidase activity.

In recent years the uses of enzyme-linked immunoassay procedures have become widespread due to their convenience and reduced biohazard risk. Antibodies can be conjugated to enzymes without complete loss of either catalytic or immunological activity. Such enzyme-antibody conjugates can be used in ELISA, histochemical staining reactions and immunoblots (with either substrates that change color, fluoresce or produce light). Luminescing products can be detected using commercially available kits by overlaying the blot with X-ray film. Thus, the invention also can be used to determine antigens using an enzyme-antibody conjugate method. In this embodiment, the enzyme label can be any plant peroxidase that participates in the conversion of a chromogen or luminal to a detectable form. In addition, the present invention improves upon such assays by employing an anti-peroxidase antibody in place of an anti-immunoglobulin antibody-enzyme conjugate. In this instance the anti-peroxidase antibody may be contacted with the peroxidase to bind it prior to the antibody's introduction into the assay. Alternatively, the anti-peroxidase antibody is introduced into the assay and then the peroxidase is added and bound by the anti-peroxidase antibody. The enzyme substrates are then added and assayed according to conventional techniques. An example of this latter method is shown in Example 23.

Theoretically, many different enzymes, such as beta galactosidase and alkaline phosphatase can be used in immunoenzyme conjugates, but in practice, peroxidase is one of the most widely employed. While horseradish peroxidase is the form of choice, other species could be of particular value. It has been discovered that soybean peroxidase possesses properties which offer significant improvement over the standard protocol with horse radish peroxidase. Soybean seed coat peroxidase shows an atypical peroxidase inactivation temperature of 90.5° C. Since soybean peroxidase (SBP) has greater stability, it has the advantage of longer shelf life, and consequently lends itself to the development of clinical kits whose durability provides economic benefits.

Figure 9:
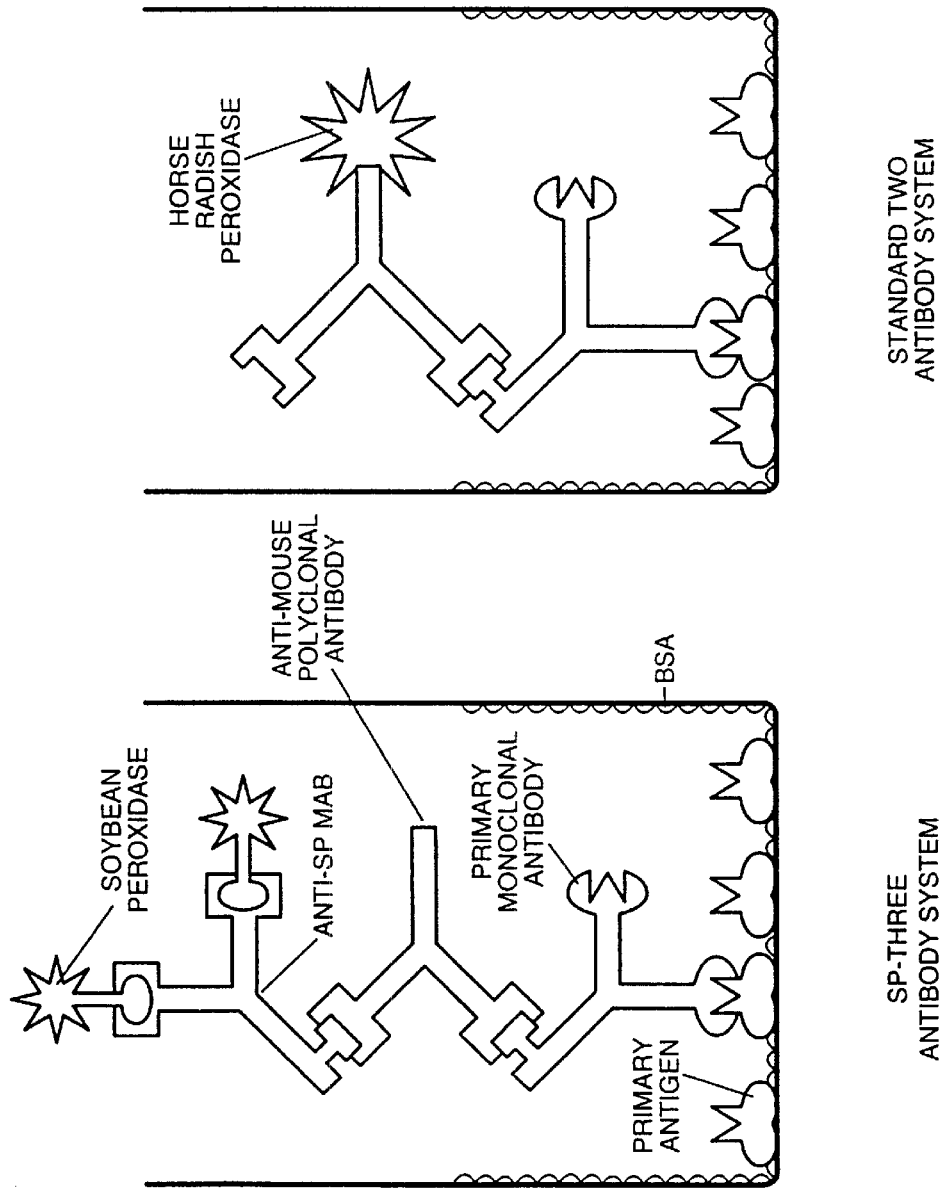
FIG. 9A Illustration of a standard ELISA protocol which employs a specific antibody against a target antigen and an anti-antibody conjugated with an enzyme.
FIG. 9B Illustration of an immunoassay protocol according to the present invention (termed SPAP) which employs a first specific antibody against a target antigen, an anti-antibody against the first antibody and a second antibody against soybean peroxidase and soybean peroxidase.

In addition, in accordance with the present invention, a monoclonal antibody (MAB) against soybean peroxidase was prepared, in order to provide an assay procedure with a higher level of specificity. The standard ELISA protocol employs a specific antibody against a target antigen, which after binding is reacted with a second antibody-enzyme conjugate. See FIG. 9A. The second antibody is generally a polyclonal antibody (PAB) raised in a different species coupled to the enzyme of choice. However, a further aspect of the present invention is the development of an assay which utilizes an additional step. This additional step is the binding of an anti-soybean peroxidase MAB to the PAB bound to the first antibody. See FIG. 9B. The anti-soybean peroxidase MAB may have previously been contacted with soybean peroxidase to produce a soybean peroxidase anti-soybean peroxidase antibody complex (SPAP), prior to its introduction into the assay. In this complex the soybean peroxidase is bound to the antibody and not conjugated to it.

Alternatively, the anti-soybean peroxidase MAB may be introduced into the assay, and then the soybean peroxidase is added and bound by the antibody. The assay is completed by the addition of substrate and detection of the product as in conventional assays. This assay provides results which are superior to prior art assays. An example of this assay is set forth in Example 22.

The soybean peroxidase of the present invention can be used to detect oligonucleotides. Classically, specific oligonucleotides are detected by hybridizing with probes that are radiolabeled by the incorporation of radioactive dNTPs. Although sensitive, the value is compromised by the short half life of radioisotopes and the expense and biological hazard associated with usage and disposal. These drawbacks have occasioned the search for alternative methods.

One such method uses a covalent conjugate of an oligonucleotide and an enzyme as shown in U.S. Pat. Nos. 4,962,029, 5,254,469 and 5,272,077, each incorporated herein by reference. Enzymes that can be used include peroxidase, glucose oxidase, alkaline phosphatase and beta-galactosidase. Chemiluminescent substrates are then used to assay for enzymatic activity and luminescing products can be detected by exposing blots to X-ray film. An alternative method uses a biotinylated, oligonucleotide probe that hybridizes to the target oligonucleotide. A strept- or nutra-avidin enzyme conjugate is bound to the biotinylated probe. Chemiluminescent substrates are then used to assay for enzymatic activity and luminescing products can be detected by exposing blots to X-ray film. Problems associated with these methods are lack of sensitivity and high nonspecific binding. A method according to the present invention using an anti-soybean peroxidase MAB to detect target oligonucleotides is illustrated in Example 21. This method can be further modified as described for other assay procedures described herein.

Other uses of the present invention involve the modification of the peroxidase enzyme, the peroxidase gene or bacteria containing the enzyme. The entire gene with its 5'- and 3'-regulatory regions can be manipulated in a variety of ways to provide for altered expression and enzyme form. In general, expression can be enhanced by including multiple copies of the peroxidase gene in a transformed bacterial or plant host, by using promoters that initiate transcription at increased levels, or by any known means of enhancing peptide expression.

A recombinant gene can be constructed that takes advantage of regulatory regions from other genes and the coding region of the peroxidase genes. The invention also relates to soybean peroxidase promoters. A recombinant gene can be constructed that takes advantage of the peroxidase regulatory regions and coding regions from other genes.

Methods of Use: Regulating Expression of Structural or Heterologous Genes

Regulatory control refers in general to the modulation of gene expression induced by DNA sequence elements, particularly those located upstream of (5' to) the transcription start site. Regulation may be analogous to an off/on switch which responds to environmental conditions, or regulation may result in variations in the level of gene expression or its tissue specificity.

Placing a structural gene under the regulatory control of a promoter or a regulatory sequence element means positioning the structural gene such that the expression of the gene is controlled by these sequences. Promoters are generally positioned 5' (upstream) to the genes that they control. In the construction of heterologous promoter/structural gene combinations, it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e. the genes from which it is derived. Again, as is known in the art, with multiple copies of regulatory elements, some variation in this distance can occur.

A structural gene is that portion of a gene comprising a DNA segment encoding a protein, polypeptide or a portion thereof. The term can refer to copies of a structural gene naturally found within the cell, but artificially introduced, or the structural gene may encode a protein not normally found in the plant cell into which the gene is introduced, in which case it is termed a heterologous gene. A heterologous structural gene may be derived in whole or in part from a bacterial genome or episome, eukaryotic genomic or plastid DNA, cDNA, viral DNA or chemically synthesized DNA. It is possible that a structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bounded by the appropriate plant—functional splice junctions. The structural gene may be a composite of segments derived from a plurality of sources, naturally occurring or synthetic. The structural gene may also encode a fusion protein, so long as the experimental manipulations maintain functionality in the joining of the coding sequences.

Soybean peroxidase promoters may be used by methods known in the art to construct transgenes for regulation of expression. For example, an expression cassette may be inserted into an appropriate vector to accomplish Agrobacterium mediated transformation of soybean (Chee et al., 1989; U.S. Pat. No. 5,376,543).

The promoter regions of the soybean peroxidase genes of the invention are AT-rich, contain several direct repeats, and include sequences similar to the TATA box typical of eukaryotic promoters. Trans-acting factors have been shown to recognize AT-rich elements in the promoters of various plant genes (Jofoku et al., 1987; Jensen et al., 1988; Bustos et al., 1989; Jacobsen et al., 1990; Ponte et al., 1994; Guillen et al., 1998). A putative tobacco seed coat-specific promoter was isolated by T-DNA tagging though a coding region was never identified (Fobert et al., 1994). Comparison of this putative promoter region with the promoters of the present invention showed no similarities. The activation element 1 (as1) of the CaMV 35S promoter (Katagiri et al., 1989) is present at −463 in the 5' flanking region of GmEPC and a G-box like sequence (GACGTG) at −462, overlapping the as1 element, is present in the GmEPC promoter. Since the soybean seed coat peroxidase is expressed in seed coat and the G-box motif is involved in ethylene induction, this deviation from the CACGTG G-box core sequence (Raghothama et al., 1993; Mohan et al., 1993) is not likely to carry a functional G-box. Whether the identified G-box like sequences of the GmEPC promoter are involved in regulation of gene expression may be determined by methods known in the art.

There is growing evidence that promoter region is not the sole region for the regulation of gene expression. Regions in structural genes, introns, 3'-untranslated portions and even regions on different chromosomes may play roles in control of gene expression (Mizukami and Ma, 1997; Sieburth and Meyerowitz, 1997; Taylor, 1997; Liu et al., 1998). The availability of epep genotype and the nature of the gene product enable the use of peroxidase itself as a reporter to conduct 5' sequential promoter deletion analysis. It was determined that the deletion of the promoter sequences from −1524 to −467 did not significantly change the expression level in seed coats. Further deletion from −467 to −207 resulted in a dramatic decrease in expression (FIG. 19), and the expression level dropped to approximately the level of epep genotypes. Although the precise nature of the promoter region that resulted in the sharp decrease in gene expression has not been demonstrated, certain features known in the art may be responsible for the decrease in gene expression. A directed repeat (−321/−459, GTGCTCCACCCA), a CAAT box (−248), the activation element 1 (as1) (TGACG, −463) and the element CMCCACA (−315) which is similar to the conserved binding motif of seed-specific genes, are all included in this region. The conserved sequence (A/T/C)AACACA(A/C)(A/T/C) has been proposed to be a cis-control element in soybean seed protein genes by Goldberg (Goldberg, 1986). This conserved binding motif has been reported in rice glutelin genes (Okita et al., 1989; Zhao and Okita, 1995), maize zein genes (Langridge and Feix, 1983; Maier et al., 1988), wheat α/β gliadin genes (Vellanoweth and Okita, 1993), barley B/C hordein genes (Muller and Kundsen, 1993), and soybean glycininl genes (Goldberg, 1986). Since the element at −315 in the GmEPC promoter region contains an additional C, it is not certain whether it can act as the seed-specific binding motif. In the gel retardation assay, a DNA-protein complex was observed when a 157-bp fragment within this region (−467 to −310) was incubated with seed coat nuclear proteins (FIG. 21). However, detection of this complex was not reproducible.

Methods of Use: Transformation of Plants

Transformed plants comprising a recombinant DNA sequence under modified or unmodified transcriptional and translational control of the peroxidase promoter and containing the hydrophobic leader sequence and a sequence encoding a protein or polypeptide may be expressed in the seed coat. Expressed transgenes may be antigenic and act as an animal or human vaccine. Transgenes also may be enzymes or nonenzymatic proteins.

Method of Use: Soybean Seed Coats for the Production of Heterologous Proteins

Soybean seed coats contain very few complex soluble proteins, which simplifies the isolation of heterologous proteins. Seed coats are easily removed and separated in the milling process. The soybean peroxidase gene of the present invention enables the peroxidase protein to be produced and located in the intercellular regions of the seed coat. By operably linking the coding region of a desired structural gene with a portion or all of the peroxidase promoter sequence and the hydrophobic leader sequence, the desired protein may be expressed in the seed coat and transported to the intercellular region, making water extraction of the protein possible.

Examples of structural genes which may be expressed employing the DNA sequences of the present invention include antibodies and vaccines. Antibodies were first produced and correctly folded in plants by Hiaft et al. (1989; 1990). The antibody may be tagged with radioactive particles or chemotherapy agents which would allow targeting of tumor cells, for example. Also, edible vaccines have been expressed in transgenic plants (Lam and Shi, 1996).

EXAMPLES

The following examples are provided to further illustrate the present invention and are not intended to limit the invention beyond the limitations set forth in the appended claims.

Example 1

Peroxidase Extraction and Monoclonal Antibody Production

Peroxidase was extracted from circular pieces of seed coat, roughly 3 mm in diameter. Samples from three seeds per replication were placed separately in micro centrifuge tubes containing 1 ml of water, incubated at room temperature for 2 hours and vortexed.

Purified seed coat peroxidase (>95% pure) and seed coat peroxidase solutions with various levels of known pupurogallin (PPU) activity were kindly provided by Enzymol International (Columbus, Ohio).

Seeds of high and low peroxidase cultivars were grown at the Purdue Agronomy Farm at West Lafayette, and a Resnik x Winchester cross was made during the summer of 1993. $F_1$ seeds were grown in Puerto Rico, $F_2$ seeds were grown in West Lafayette and $F_3$ individual seeds were tested for peroxidase activity.

BALB/c mice (Mus musculus) were subcutaneously injected with a total of 0.1 mg purified seed coat peroxidase (>95% pure) kindly provided by Mead Central Research (Chillicothe, Ohio). Fusions with myeloma parent P3/NS1/1-Ag4-1 (NS-1) were done with polyethylene glycol 4000. Hybridomas were selected on hypoxanthine (100 nM), aminopterin (0.4 nM), and thymidine (16 nM) media and clones were obtained using the limited dilution method. Raw ascites solution was collected and used in all procedures. Hybridomas were initially selected on their antibody's ability to bind peroxidase. Hybridomas were subsequently selected on their antibody's ability to bind peroxidase in such a way as to not affect enzymatic ability. We have selected a hybridoma that has been designated A4.

Example 2

Enzyme-linked Immunosorbent Assay (ELISA)

An indirect detection method using an alkaline phosphatase antimouse immunoglobulin and p-nitrophenyl phosphate as the chromogen was used to detect seed coat peroxidase. Raw ascites was diluted 1:10, 1:100, 1:1000, and 1:5000. Quantitation of three wells per replication was done at 405 nm after 45 minutes of development. ELISA detects protein or enzyme concentration but not enzyme activity, so ELISA is not suitable for plant breeding for higher peroxidase activity, or the detection or monitoring of peroxidase activity (FIG. 1)

Example 3

Peroxidase Capture Assay (PCA)

Figure 2:
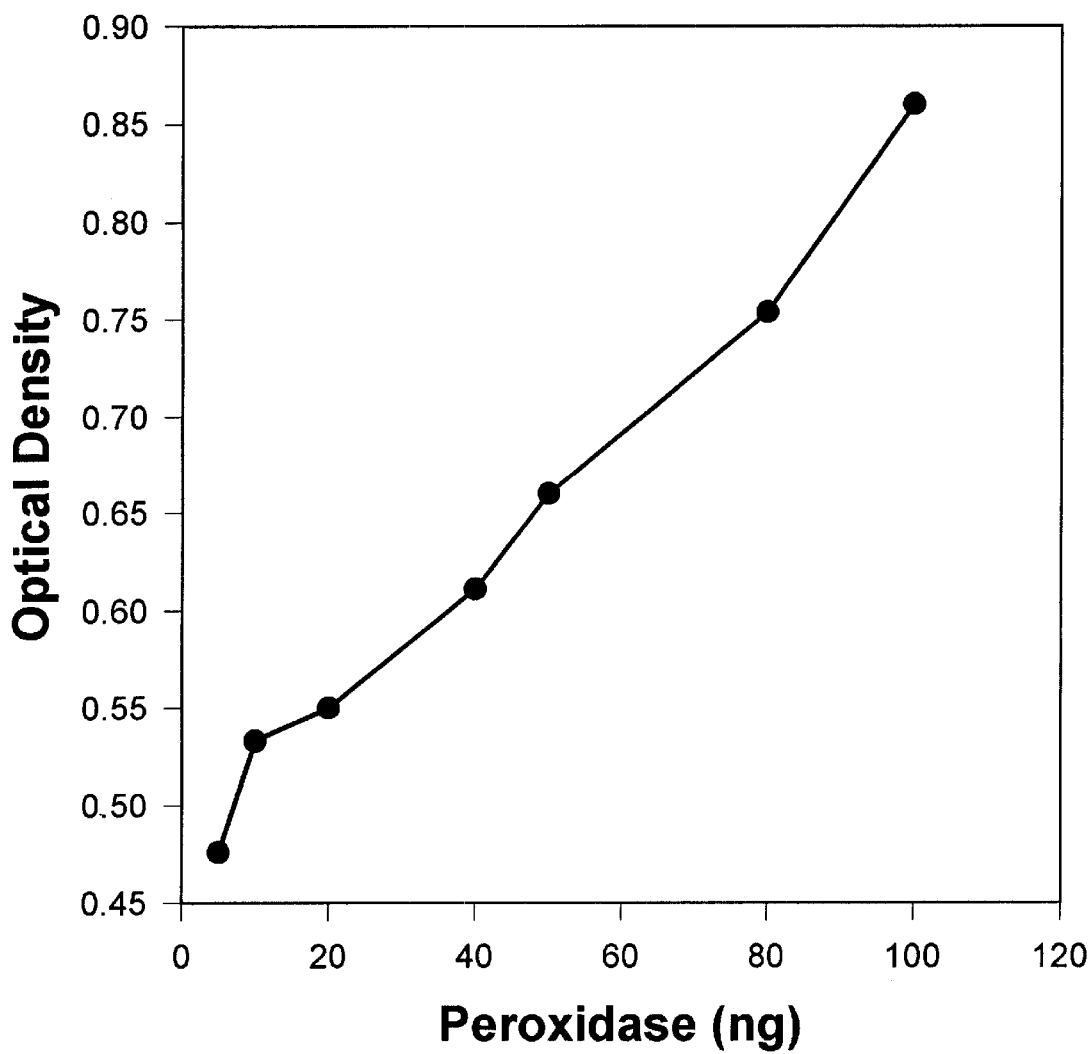
FIG. 2 Average Peroxidase Capture Assay (PCA absorbance (450 nm) of purified peroxidase samples against 1:5000 dilution of peroxidase MAB.

ELISA plate wells were coated with 100 μL of a 1:100, 1:1000, 1:5000, and 1:10,000 dilution of ascites fluid and incubated overnight at 4° C. After incubation, the ascites fluid was removed and 100 μL of 1% (w/v) bovine serum albumin, acting as a blocking agent, was added. After a 1-h incubation at room temperature, wells were washed three times with phosphate-buffered saline (PBS; 137 mM NaCl, 1.47 mM $KH_2PO_4$, 8.10 mM $Na_2HPO_4$, and 2.68 mM KC1, pH 7.4) containing 0.05% (v/v) Tween-20. Peroxidase samples were added to the wells and incubated at room temperature for 1 h. Wells were washed three times with PBS-Tween-20. A soluble, peroxidase chromogenic substrate (100 μL, tetramethylbenzadine) was added to the bound peroxidase. After 30 seconds, the reactions were stopped by the addition of 50 μL of 1N $H_2SO_4$ and three wells per replication were read at 450 nm (FIG. 2).

Example 4

Guaiacol Method

Figure 3:
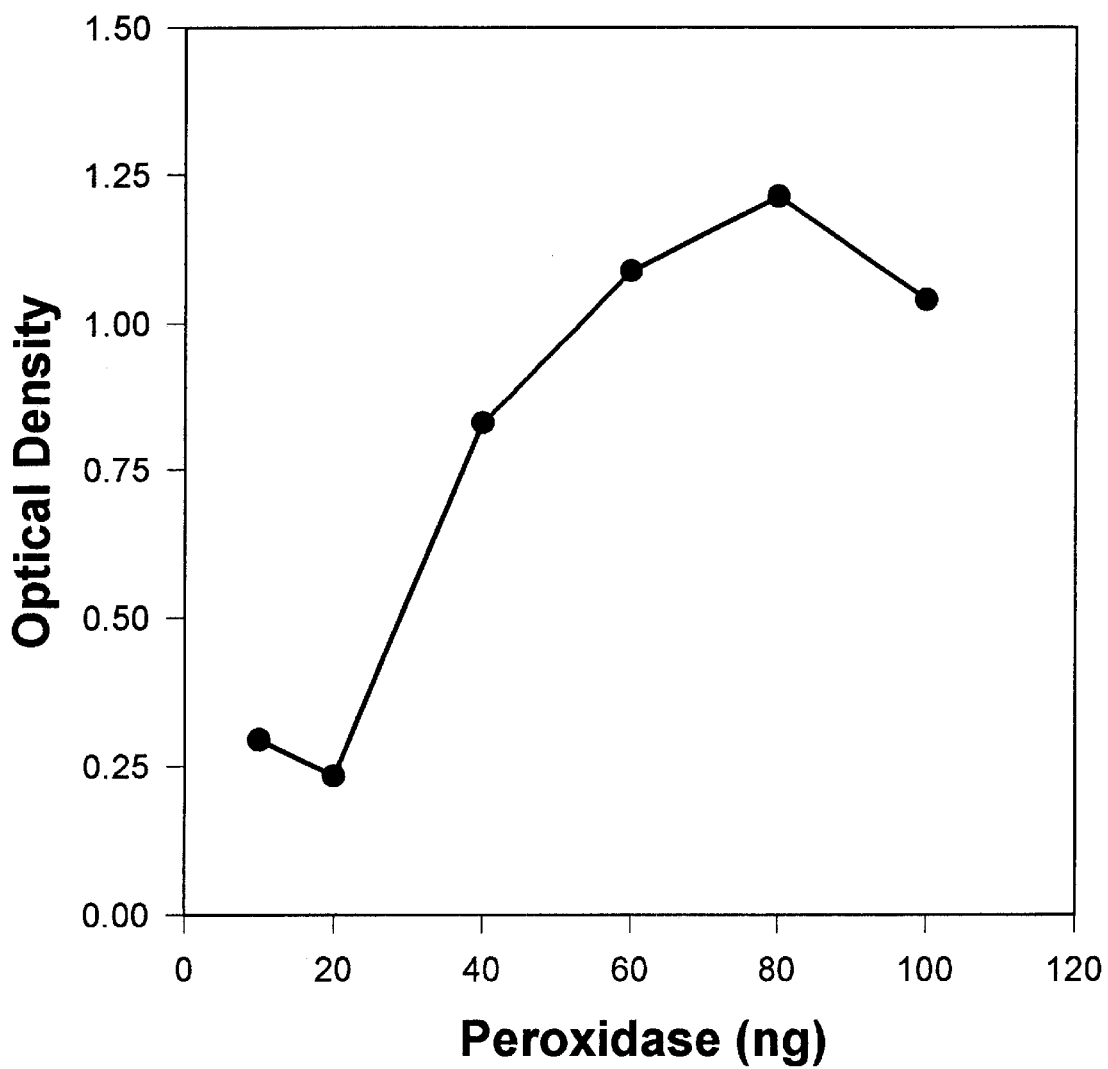
FIG. 3 Average guaiacol absorbance (470 nm) of purified peroxidase.

Purified peroxidase or seed coats were incubated in micro centrifuge tubes containing 1 ml of 0.5% (v/v) guaiacol at room temperature for 10 minutes before the addition of 50 μL of 0.1% (v/v) hydrogen peroxide. After 5 minutes, peroxidase activity was noted, with a brown solution being positive and a clear solution being negative. Peroxidase activity using a guaiacol substrate was also measured at 470 nm as described in Buttery and Buzzell, Crop Science, 8:722–725 (1968). Measurement of known peroxidase solutions, shows this procedure does not give a linear response and is therefore not suitable for plant breeding (FIG. 3).

Example 5

Method Comparison Comparison

In the ELISA procedure, we were unable to detect peroxidase with the 1:1000 and 1:5000 dilutions and the 1:100 dilution gave inconsistent results. Using the 1:10 dilution, we were able reproducibly to detect peroxidase. There was no increase in the optical density (OD) beyond 60 ng of peroxidase (FIG. 1).

In the PCA test, the 1:10000 dilution gave inconsistent results. Since the other dilutions gave similar results, the 1:5000 dilution was chosen because it uses the least amount of MAB (FIG. 2). Analysis of variance showed that a linear model explained the data ($R^2=0.99$).

Figure 4:
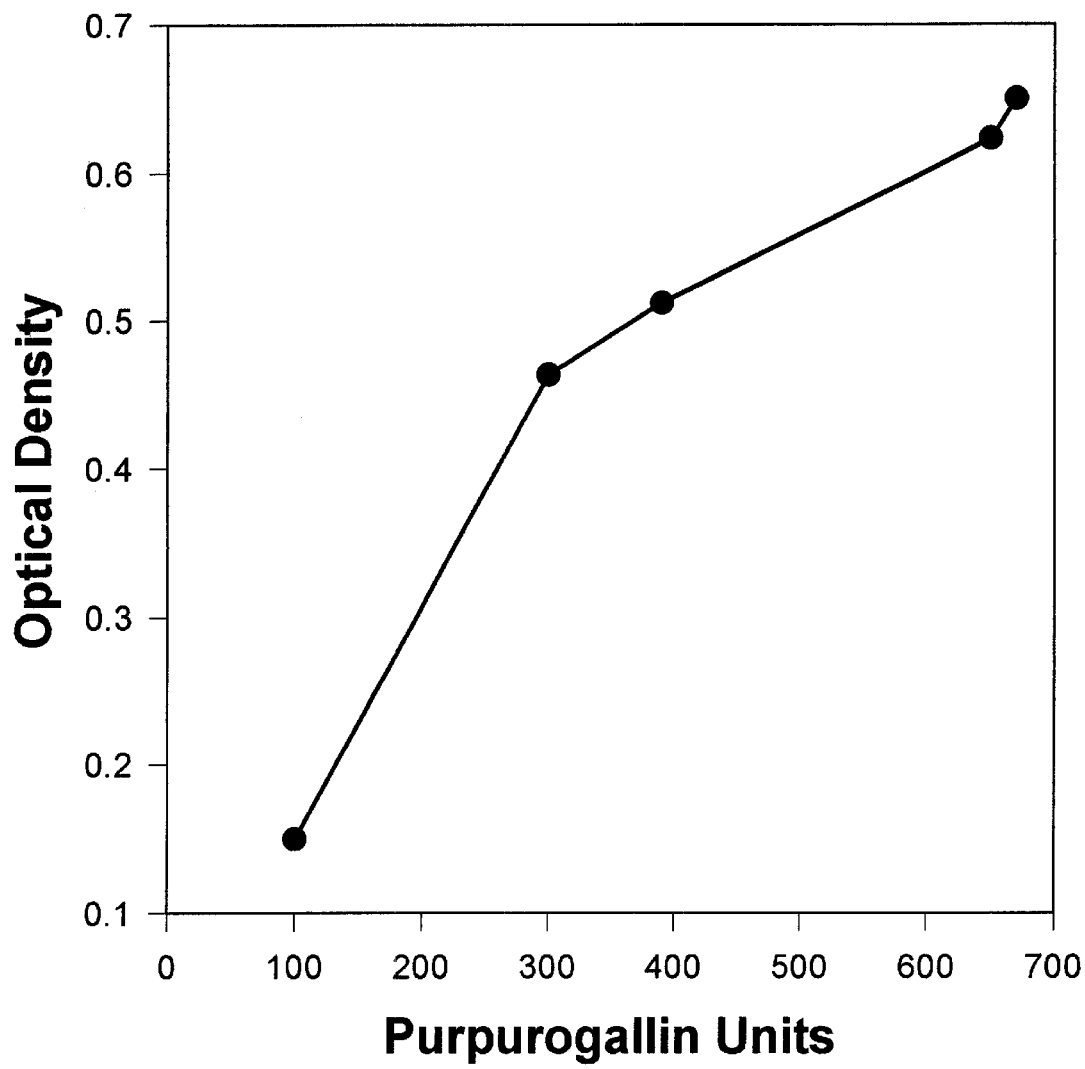
FIG. 4 Average PCA absorbance (450 nm) of peroxidase solutions of known activity against 1:5000 dilution of peroxidase MAB.

Using a guaiacol substrate, peroxidase activity was measured at 470 nm (FIG. 3). Using analysis of variance, a linear model was inadequate to explain the data $R^2=0.77$).
ELISA and PCA Comparison ELISA and PCA Comparison Boiled and nonboiled samples of purified peroxidase, were analyzed using both the ELISA and PCA assays. Presence or absence of peroxidase activities were checked using the guaiacol method (Buttery and Buzzell, 1968).
Analysis of Solutions with Known Peroxidase Activity To determine if PCA could detect differences between samples with different peroxidase activities, samples with 100, 300, 390, 650, 670, 1500, and 2000 PPU/ml were analyzed using PCA (FIG. 4). There was no increase in the OD of the 1500 and 2000 PPU/ml samples over the 670 PPU/ml sample.

There was a major difference between what the PCA and ELISA techniques measured. The ELISA measures peroxidase concentration and not activity; the PCA measures activity not concentration. This was confirmed using the ELISA, PCA, and guaiacol procedures on boiled and nonboiled peroxidase samples. Comparison of the boiled and nonboiled OD of the guaiacol results showed an obvious difference. The guaiacol method showed high peroxidase activity in the nonboiled sample and no peroxidase activity in the boiled sample. The ELISA technique generated OD readings for both the boiled and nonboiled samples. There was a decrease in the ELISA OD between the boiled and nonboiled, which was probably attributable to destruction of the protein during the extended boiling of the sample. By comparison, the PCA OD was 0.0 in the boiled sample and 1.154 in the nonboiled sample. This is consistent with what one would expect looking at the differences between procedures. The ELISA technique used was a two-step indirect method. Conversely, in the PCA technique, peroxidase was captured by the peroxidase monoclonal antibody coating the sample well. There was no secondary enzyme-linked antibody in the reaction. The peroxidase chromogen was added directly to the bound peroxidase, which reacted with the chromogen. Therefore, the PCA technique measures activity and not peroxidase concentration. This is why the boiled sample, which had no activity, had no PCA OD reading. Since the antibody captured peroxidase maintains enzymatic activity, the antibody must bind to an epitope not involved with enzymatic activity.

Solutions with known differences in peroxidase activity were analyzed to confirm the result that PCA gives a quantitative measure of peroxidase activity. Results show that the PCA can detect differences in solutions containing various levels of known peroxidase activity (FIG. 4).

Peroxidase activity also may be measured using guaiacol as a substrate. Comparison of the peroxidase activity curves clearly showed a difference between this method and PCA. There was a linear relationship using PCA, but a linear model was not adequate to describe the relationship using the guaiacol method. A higher order model was needed to explain the guaiacol curve. We believe the PCA technique was superior since the relationship may be explained by a simpler model.

Example 6 cDNA Library Construction and Screening

Total RNA was extracted from soybean (Glycine max cv. Resnik) seedbuds 21 days after flowering as previously described. Poly(A)-enriched RNA was prepared from total RNA using PolyATract and the cDNA library was constructed in the unidirectional vector Uni-ZAP XR.

A plant peroxidase specific primer (PSP) was generated from a conserved amino acid region (distal heme ligand, HFHDCFV, SEQ ID NO 1) in all plant peroxidases (5CA(C/T)TT(T/C)CA(C/T)GA(C/T)TG(C/T)TT(C/T)GT3') (SEQ ID NO 2). The probe was generated using the 3'RACE system with soybean seedbud total RNA and PSP as described by the manufacture except that hot-start PCR was performed. The PCR-RACE products were cloned into pCR™II plasmid. DNA from twenty clones was purified and digested with EcoR I, fractionated by electrophoresis on a 1% agarose gel, and blotted on a nylon membrane that was probed with [γ-$^{32}$p]dATP-end-labeled PSP. A single positive clone was random prime labeled with [α-$^{32}$p]dCTP and used for primary screening of the cDNA library (2.5×10$^5$ PFU). Prehybridization was conducted in 6×SSPE, 5×Denhardt's, 0.5% (w/v) SDS, 100 µg/ml denatured salmon sperm DNA, and 50% formamide at 42° C. for two hours. Hybridizations were performed overnight and the conditions were the same as those in prehybridization except that 1×Denhardt's was used.

PCR using PSP and the T7 vector primer flanking the cloning site was used to purify single phage clones. Phage particles were eluted by incubating primary picks and/or single plagues in 500 µl of SM buffer (SM: 100 mM NaCl, 10 mM MgSO$_4$, 0.01% w/v gelatin in 50 mM Tris pH 7.5) at room temperature for 2 hours. The PCR cycling parameters were 94° C., 1 minute at 57° C., and 1 minute at 72° C., and followed by a final extension at 72° C. for 5 minutes. PCR reaction conditions were 1× reaction buffer (500 mM KCl, 100 mM Tris-HCl, pH 9.0, 1.0% Triton X-100), 1.5 mM MgCl$_2$, 200 µM each dNTPs, one unit of Taq DNA polymerase, 1 µM each primer and 2 µL of phage particle elution in 50 µL total.

DNA sequencing of both strands was performed using Sequenase Kit 2.0 (USB) and SK and KS primers (Stratagene). Synthetic primers corresponding to internal sequences of cDNA and genomic DNA were made to sequence the fragment in both directions. Sequence data were analyzed using GCG software (Madison, Wis.).

Example 7

Northern Blot Analysis and RT-PCR

Twenty-five µg of total RNA from various tissues were fractionated on 1% agarose gel containing formaldehyde, blotted onto nylon membrane, and probed with $^{32}$P labeled probe. Both prehybridization and hybridization conditions were the same as those described in library screening. Sample isolations and hybridizations were replicated twice.

cDNA specific primers designed from 3' untranslated regions of each cDNA and PSP were used in reverse transcript PCR (RT-PCR) to study expression patterns. For GmEPa1 (SEQ ID NO 12), GmEPa2 (SEQ ID NO 12), GmEPb1 (SEQ ID NO:16), and GmEPb2 (SEQ ID NO 16) the primers were 5'AAATTMCTCAGCTGTGGG3' (SEQ ID NO 3), 5'GGMCCCACTTATTCCATCG3' (SEQ ID NO 4), 5'CCCMGACATGCTTGAGAT3' (SEQ ID NO 5), and 5'AAGTTCATACTTCTAAC3' (SEQ ID NO 6), respectively.

Two µg of total RNA from different tissues of soybean were used for synthesizing the first strand of cDNA using SUPERSCRIPT II RNase H REVERSE TRANSCRIPTASE as suggested by the manufacture (BRL). RT-PCR conditions were the same as those in 3'RACE except that the annealing temperature for GmEPb2 was 45° C.

Example 8

Sequence Analysis of Soybean Peroxidase cDNAs

The conserved amino acid sequence of plant peroxidases enabled the generation of molecular probe for plant peroxidase genes using 3'RACE. The 3'RACE experiment with PSP and adaptor primer complimentary to the oligo-d(T) end of the cDNA resulted in amplification of a 900-bp DNA fragment (data not shown). Using the fragment as probe, 25 clones were obtained by primary hybridization screening. Eleven positive clones were recovered after two rounds of PCR using PSP and T7 vector primers, and four clones, designated GmEPa1, GmEPa2, GmEPb1, and GmEPb2, were further analyzed.

The nucleotide sequences of the coding regions of GmEPa1, GmEPa2, GmEPb1, and GmEPb2, and the predicted amino acid sequences of their protein products, i.e., SEQ ID NOS 11, 13, 15, and 17, are shown in FIGS. 5 and 6. The coding regions of GmEPa1 and GmEPa2 exhibit 97% amino acid identity, the coding regions of GmEPb1 and GmEPb2 have 95% amino acid identity, and the coding regions of GmEPa1 and GmEPb1 share 47% amino acid identity. Comparison of 168 bp, 3' untranslated regions of GmEPa1 and GmEPa2 revealed 83% homology. The homology between the 187 bp, 3' untranslated regions of GmEPb1 and GmEPb2 was 75%. There are 6 putative glycosylation sites specified by N-X-T/S at amino acid residues 56, 69, 128, 142, 183 and 214 in GmEPa1 and GmEPa2, and there are 4 putative glycosylation sites at residues 70, 142, 185 and 195 in GmEPb1 and GmEPb2, respectively; and GmEPa1 and GmEPa2 had the [Q L X X X F Y] (SEQ ID NO 7) motif, where X is any amino acid, at the $NH_2$ terminus which is a feature found in most plant peroxidases. No [Q L X X X F Y] (SEQ ID NO 7), motif exists in GmEPb1 and GmEPb2. Based on predicted amino acid sequences, all four proteins contain predominantly hydrophobic amino acid signal sequences. Two copies of the putative polyadenylation signals AATAAG, (SEQ ID NO 8) are present 39 and 106 bases upstream of the poly (A) signal in GmEPa1 and 19 and 75 bases upstream in GmEPa2. There is only one copy of the putative polyadenylation signal AATAAA 36 bases upstream of the poly (A) in GmEPb1 and 14 bases upstream in GmEPb2

Example 9

Comparisons with Other Plant Peroxidase Amino Acid Sequences

Comparison between the predicted amino acid sequences of soybean peroxidases and some other plant peroxidase sequences. The level of identity suggests that the clones encode peroxidases. There are three most highly conserved amino acid regions in almost all plant peroxidases. The first is from amino acid residues 33–55 with a predicted disulfide bridge in the middle and a potential heme binding site which belongs to a subdomain of 100% homology: HFHDCFV, SEQ ID NO 9. The second is from amino acid residues 89–105, again with two cysteines that may form disulfide bridges. The third is from amino acid residues 159–170 with a potential heme binding site in the middle. All of the peroxidases studied, except GmEPb2, have eight cysteine residues that are located in similar positions in the primary sequences, and two invariable histidine residues (at positions 42 and 167 in soybean peroxidases, FIGS. 5 and 6) are inferred in the active-site structure. The number of glycosylation sites vary greatly according to the isozymes (from 1 in peanut PNC2, 3 and 6 in soybean, to 8 in horseradish).
Differential Expressions of Peroxidase mRNAs Total RNA from leaf, stem, root, seedbud, and developing seed were probed with a 300 bp Kpn-Tifl fragment from the 3' untranslated region of GmEPa1. Data revealed that transcripts of approximately 1400 nucleotides from GmEPa1 are present in developing seed and root. Since both the coding regions and the noncoding regions of the four cDNAs are highly homologous, RT-PCR experiments were conducted to study the differential expressions of peroxidase mRNA. Data shows the amplification of cDNA synthesized from total RNA of different tissues with PSP and GmEPa1-specific primer. To confirm the identity of RT-PCR products, RT-PCR products were transferred to nylon membrane and hybridized with GmEPa1 from which GmEPa1-specific primer was designed. Based on the results of RT-PCR with cDNA-specific primers, transcripts from GmEPa2 were also detected in root and developing seed, and transcripts from GmEPb1 and GmEPb2 were detected in root, stem, leaf, and seedpod.

Example 10

Peroxidase Cloning

Our results demonstrate that PCR coupled with one round of conventional plaque lift hybridization was effective and rapid in both characterizing and screening of cDNA libraries provided that sequence information is available. This method would be especially useful when high density plating is used to obtain low abundance clones. Using PSP coupled with a vector primer, one can easily find the primary picks that are true positive clones. By replating the primary picks at low density, individual positive clones can be easily recovered by a second round of PCR with the same pair of primers. Directly using phage particle elution as template in PCR reactions without further precipitation was easily accomplished. The technique amplified a single, distinct product band from as few as $1 \times 10^6$ phage particles that corresponds to ~0.1 ng of DNA, or as many as $1 \times 10^8$ phage particles have been used under the same amplification conditions with no detectable loss of specificity. Another advantage of this method is the size of the insert of positive clones can be predicted. A gene-specific primer coupled with vector primer also can be used to reveal the presence of genes of interest in a library prior to screening due to the high sensitivity of PCR. Failure to amplify any product of interest from the library may indicate that full-length cDNA of interest is not likely to be present in the library. In such case, unproductive screening can be avoided.

The predicted amino acid sequences of the four cDNAs exhibit homology to other plant peroxidases indicating that the clones encode peroxidase. Each enzyme, except GmEPb2, has eight cysteines in nearly identical positions in the primary sequences. Similar cysteines in horseradish and turnip enzymes had been shown to be involved in intramolecular disulfide linkages. By analogy with horseradish and turnip sequences four intrachain disulfide linkages can be predicted in the soybean isoperoxidases GmEPa1 and GmEPa2 (cysteine pairs between residues 11/89, 44/49/, 95/298 and 174/207).

There are three highly conserved amino acid sequences in all plant peroxidases. The first and the third contain the distal and proximal histidine residues concerned with binding the heme group. The first critical histidine ligand in GmEPa1, GmEPa2, GmEPb1, and GmEPb2 occurs at amino acid 42 in the mature proteins, thought to act in acid/base catalysis, and the second at 167 thought to bind the 5th ligand of heme iron. His-42 and His-167 are almost at identical positions in all plant peroxidases.

Plant peroxidases differ greatly in the number and the position of putative glycosylation sites and the heterogeneity of glycosylation indicated that peroxidases exist in differently glycosylated forms or glycoforms. Variability in N-linked oligosaccharide chain location may be adaptively important for fine tuning catalytic properties of the functional enzyme molecule. However, a glycosylation site at residue 183 in GmEPa1 and GmEPa2 (185 in GmEPb1 and GmEPb2) is common to most plant peroxidases.

It is predicted from the cDNA sequences that all four proteins are initially synthesized as preproteins with predominantly hydrophobic amino acid signal sequences, suggesting that the mature proteins could be secreted through cell membranes. The hydrophobic residues in the signal peptides are of great importance and signal peptides are believed to function primarily by interacting favorably with the nonpolar interior of the membrane, entering and spanning it. All cloned plant peroxidases so far have a signal peptide and are therefor targeted to the secondary pathway. This was confirmed by biochemical studies of tobacco peroxidases localizing the peroxidases with pH 7.2–7.5 to the vacuoles and acidic peroxidases to the cell walls. It was reported that a C-terminal propeptide of 15 residues was necessary for proper sorting of barley lectin to vacuoles and that the vacuolar protein had this signal removed. Comparison of horseradish C protein and the cDNA derived sequences showed that 15 residues were removed at the C-terminus. The deduced amino acid sequences of soybean peroxidases showed no C-terminal extension present in peroxidases targeted to the vacuole.

Soybean peroxidases GmEPb1 and GmEPb2 may represent a new family of plant peroxidases and, perhaps, a new, unique biological function, as it is less than 50% amino acid identical to other known peroxidases. Cluster analysis of 2 plant peroxidases showed that GmEPb1 and GmEPb2 form a distinct group. GmEPa1 and GmEPa2 show about 67% amino acid identity to tomato anionic peroxidases tap1 and tap2. Using tap1 or tap2 promoter/GUS fusions, the induction of the peroxidase genes by wounding and pathogen attack has been reported, (Mohan, et al., Plant Molecular Biology 21:341–354, 1993). This suggests a role of these peroxidase genes in wound healing process and in the plant defense response. A root-specific peroxidase gene has been described in Nicotiana sylvestris and its expression was initially linked to the initiation of the cell cycle of in vitro cultured protoplasts. Acidic tobacco peroxidase, TOP A, is a constitutive, cell wall bound peroxidase most abundant in root and stem and thought to participate in secondary cell wall thickening. Over-expression of TOP A in transgenic tobacco gave rise to light-dependent wilting. A powdery mildew induced peroxidase pPOX381 of wheat leaves is about 90% identical to a constitutive wheat root peroxidase. The pPOX381 is 57% identical to TP 7, a highly basic peroxidase of the evolutionarily remote turnip, suggesting that these peroxidases might share common functional roles. These very different characteristics of plant peroxidase families may indicate that peroxidases have evolved to participate in very different biological functions.

Our results showed that RT-PCR with gene-specific primers is an effective and sensitive way to study expression of highly homologous genes. The result of RT-PCR was the same as that of Northern blotting, but RT-PCR in which 2 $\mu$g of total RNA was used is more sensitive than Northern blot in which 25 $\mu$g of total RNA was used in detection of gene expression. The expression patterns of the genes obtained from both northern analysis and RT-PCR indicates differential expressions of various genes. In studies of other plants, there was evidence of differential expression of peroxidase genes. It is not apparent why some organisms have a relatively large number of expressed peroxidase genes. One possibility is that the different encoded proteins have different functions. However, different isoforms can be produced by post-translational modification, suggesting that different genes might not be necessary to provide different functions. A second possibility is that multiple genes could allow for greater regulatory flexibility. Some genes may be expressed in specific organs or at specific stages, and the expression of the genes may be determined by different signals. Regulation studies of the different peroxidase genes and the specific functions of their products are under way.

Example 11

Detection of Soybean Cyst Nematode Feeding

Soybean cyst nematode (SCN) is a major pest of soybean, which decreases yield by feeding on roots. Seedlings from 4 SCN resistant and 2 susceptible cultivars were challenged with 3000 SCN juveniles. Control seedlings were not challenged with SCN. Samples were collected at 0, 1, 2, 3 and 4 weeks and peroxidase activity assayed according to example 3. There was no increase in peroxidase activity at weeks 1 and 2. There was increased peroxidase activity in all cultivars at week 3 (range 3 to 89%). At week 4, the increase in activity ranged from 4 to 41%. By week 5 there was no increased peroxidase activity in the SCN challenged samples. Samples were taken from root tissue.

Example 12

Quantitation of Peroxidase Activity in Stored Seeds

Seeds from high peroxidase soybean cultivars were stored under various conditions to determine factors that affect peroxidase activity. Two replicates of seed lots were stored at 10° C., 20° C., 30° C., 40° C. and warehouse conditions. Seed were equilibrated to moistures of 9 and 13%. Samples were drawn monthly except for 40° C., which was drawn weekly. Peroxidase activity was determined according to Example 3. Results show that the greater the temperature, the greater the decrease in peroxidase activity.

Example 13

Immunopurification of Peroxidase

Peroxidase was purified from plant fluid and solutions by immunoprecipitation. Solutions containing peroxidase were mixed with said antibody. Protein A-sepharose was added to the peroxidase/antibody mixture and incubated for one hour at 4° C. The tertiary protein A—peroxidase antibody complex was collected by centrifugation and washed three times. The resuspended sepharose beads were incubated at 4° C. for 20 minutes. After the last wash, 30 $\mu$l of gel-loading buffer was added to the beads. Samples were heated to 100° C. for 3 minutes and the protein A-sepharose was removed by centrifugation. Purified proteins were separated on a nondenaturing acrylamide gel and visualized by histochemical staining using tetramethylbenzadine as a chromogen. Results show a single peroxidase band on the gel.

Example 14

Crop and Cultivar Screening

Figure 7:
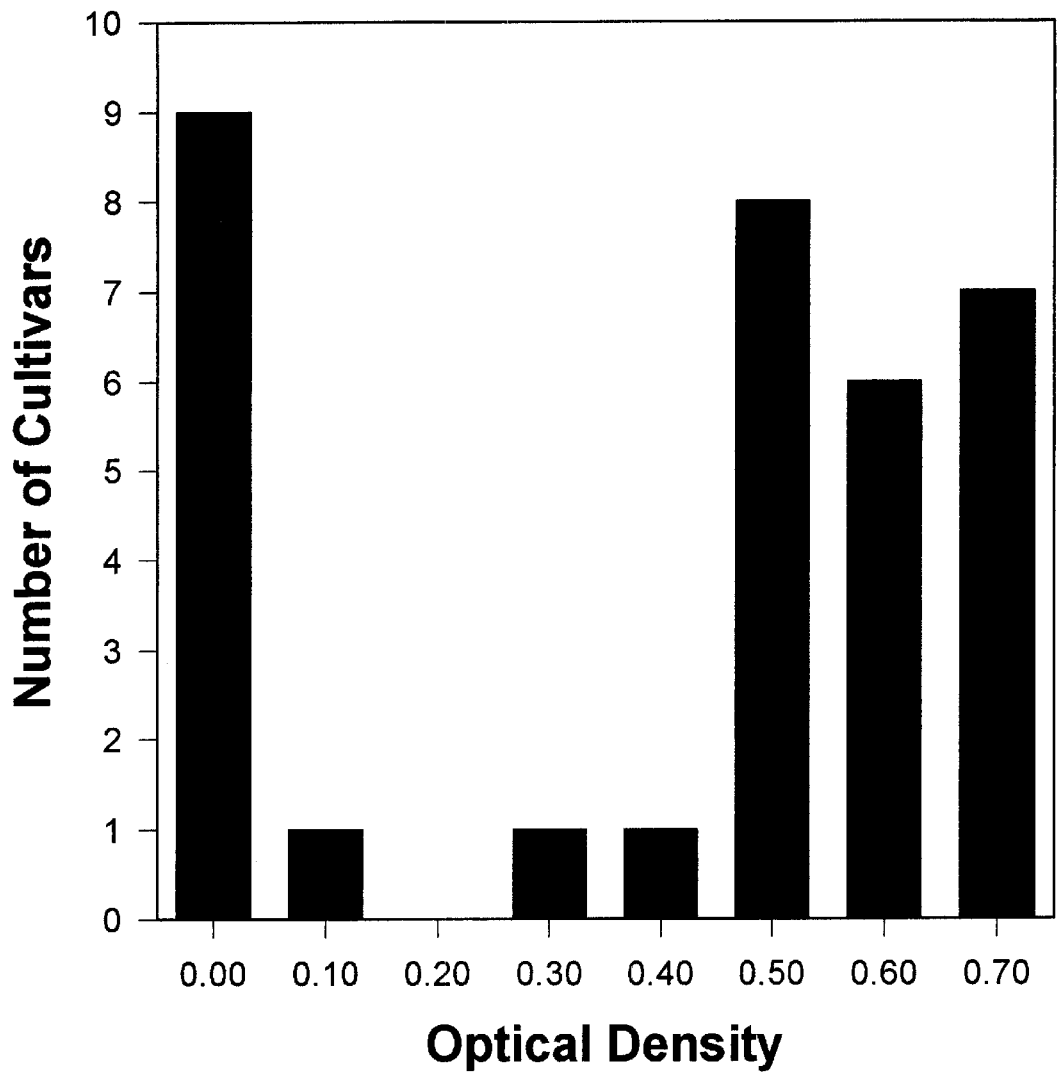
FIG. 7 Histogram of average SPCA absorbance of cultivars.
Figure 8:
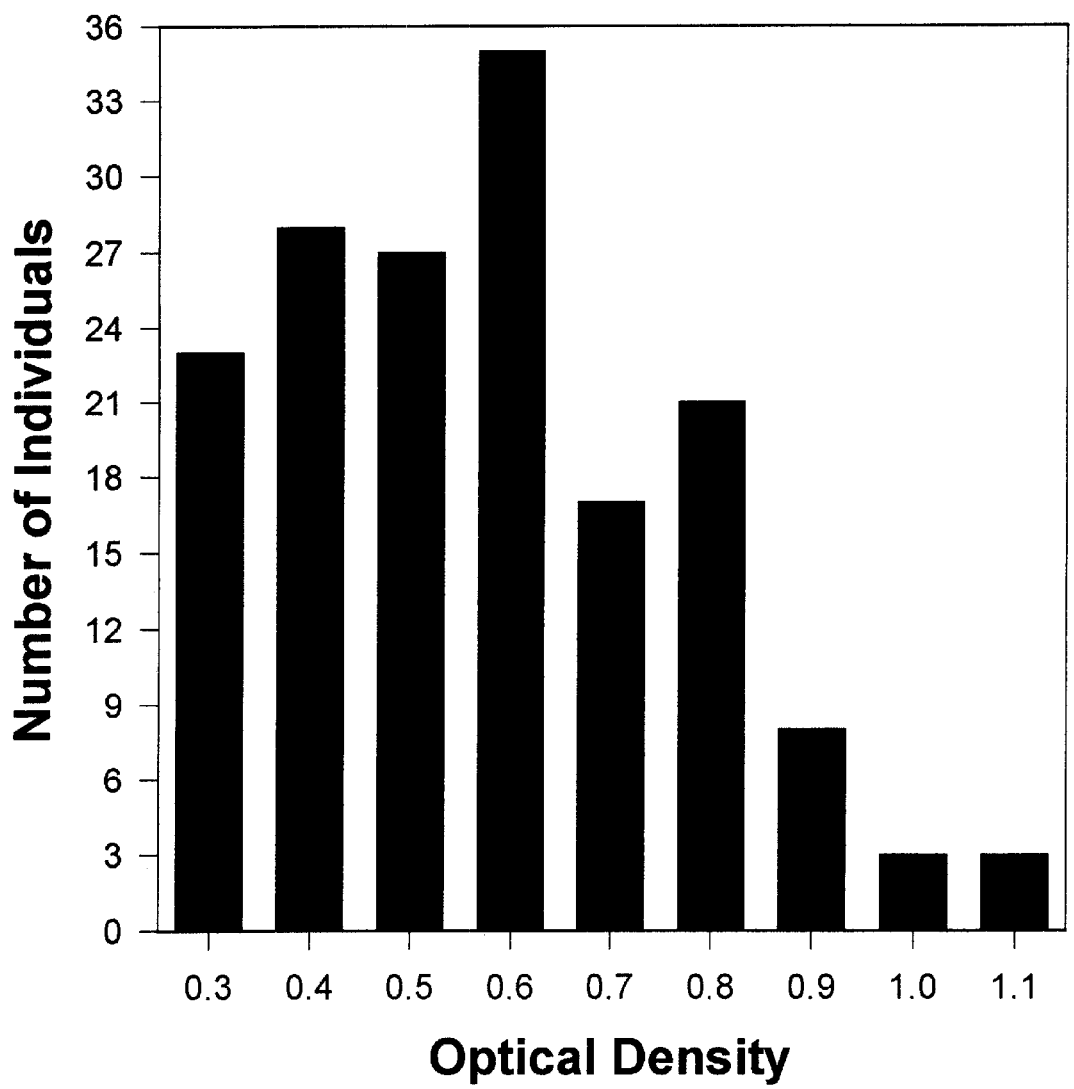
FIG. 8 Histogram of average absorbance of genotypes within an $F_3$ segregating population. Optical density values were 0.777 for Resnik and 0.502 for Winchester.

The use of said antibody is not limited to soybean. In soybeans though, 306 plant introductions from USDA and 33 cultivars were screened for peroxidase activity (FIG. 7). The invention is also useful for screening segregating populations as in a plant breeding program. The means from three replications of the high-peroxidase cultivars used as parents in the cross, Winchester and Resnik, were 0.502" 0.038 and 0.777" 0.082 respectively. PCA detected differences in a segregating population (FIG. 8). One hundred fifteen progeny from a cross of two high peroxidase cultivars were screened for peroxidase activity. Genotypes with peroxidase activity higher than both parents were identified. The invention also detected differences in peroxidase activity between 9 sorghum, 5 wheat, 5 corn and 2 oat cultivars.

Analysis of the segregating population showed that PCA can detect differences in peroxidase activity and genotypes with activity greater than the highest parent were identified. PCA will therefore be useful in the introgression of high peroxidase activity into breeding lines. The PCA technique uses the same equipment as the ELISA technique and large scale screening will therefore be routinely available. Results show that peroxidase can be easily extracted from seed coats without destroying the seed. Besides being a valuable procedure for screening cultivars for high peroxidase activity, this technique also will permit investigations of the effect that environment and seed storage have on peroxidase activity.

Example 15

Increased Peroxidase Activity in Plants

Peroxidase activity can be increased through plant breeding as described in Example 14. Another method is through plant transformation. Duplicate copies of the gene may be incorporated into plants. Another manifestation is the transformation of altered or mutant copies of the gene. DNA sequences may be altered by means of in vitro mutagenesis and alteration of the regulatory regions, promoter, 5'- and 3' untranslated regions, coding regions or termination sequences may increase expression of the peroxidase gene. Transformation and production of peroxidase is not limited to soybeans and may be accomplished in plants that are transformable.

Example 16

Production of Peroxidase in Bacteria

A single recombinant colony was incubated overnight at 37° C. in 3 ml of LB medium containing 100 µg/ml ampicillin. One ml of culture was used to inoculate 50 ml of fresh LB containing ampicillin and allowed to grow to an $OD_{600}=0.5$. IPTG was added to a final concentration of 0.5 mM and incubated for an additional 4 hours. Two hundred µl of the culture was pelleted by centrifugation and resuspended in 100 µl of TE. Bacteria was homogenized for 45 seconds with an acetal pestle. The homogenate was centrifuged and 50 µl of the supernatant was analyzed on both an acrylamide gel and the invention as stated in example 3. Functional peroxidase was isolated from bacterial cultures.

Example 17

Genomic Library Construction and Screening

DNA was extracted from fresh leaves at 65° C. for 1 h in 10 mM Tris-HCl pH 7.5, 0.7M NaCl, 10 mM EDTA, 1% β-mercaptoethanol and 1% hexadecyltrimethyl ammonium bromide (CTAB) buffer. Samples were extracted once with chloroform:isoamyl alcohol (24:1) and 1/10 volume of 10% of CTAB was added to the samples. And the samples were extracted a second time with just chloroform:isoamyl alcohol. DNA was precipitated at room temperature by the addition of isopropanol (final concentration 70%). DNA was spooled out with a flamed glass hook and placed in a tube containing 80% ethanol and 15 mM ammonium acetate, overnight. After the DNA was air dried, it was resuspended in TE and quantitated spectrophotometrically at 260 nm.

Genomic DNA was partially digested with Sau 3A and fragments of 9–23 kb were purified by low melting point agarose method (0.8%). The size-fractionated DNA was ligated to dephosphorylated BamH I arms of the phage vector EMBL3SP6/T7 (Clontech), which was subsequently packaged into phage particles using Gigapack II Gold packaging extract (Stratagene). The packaged material was used for the transfection of the host strain E. coli XL1-Blue MRF (Stratagene).

A genomic DNA library of Glycine max. cv. Resnik in EMBL3SP6/T7 was screened with soybean peroxidase cDNA GmEPa1, GmEPb1 and GmEPc. Nine clones were obtained from a total ~$5 \times 10^5$ recombinants after one round of hybridization. Internal primer pairs from cDNA were used to identify true positive clones. Three clones corresponding to GmEPa1, GmEPb2 and GmEPc were identified and were designated respectively GmEPA1, GmEPB1 and GmEPC. The genomic DNA fragments were digested with Xho I and subcloned into pBluescript (Stratagene). Primers used for cDNA sequencing were used to sequence the genomic DNA in both upstream and downstream directions.

Ten µg of DNA was digested to completion with 5 units/µg of BamH I, EcoR I, Hind III, Sac I or Xba I. Digested DNA was analyzed electrophoretically in 1% agarose/TAE gel. DNA was transferred to nylon membranes by the following procedure: (1) 0.25 N HCl, for 10 min: (2) 1.5 M NaCl, 0.5 M NaOH for 30 min; (3) 1.5 M NaCl, 0.5 M Tris-HCl pH 7.5 for 30 min. Blots were prehybridized and hybridized in 6×SSPE (0.9M NaCl, 60 mM $NaH_2PO_4$, and 6 mM EDTA), 50% formamide, 5×Denhardt's solution (0.1% ficoll 400, 0.1% polyvinylpyrrolidone, and 0.1% bovine serum albumin), 0.5% SDS, 100 µg/ml denatured salmon sperm at 42° C. Full length cDNA of GmEPa1 and GmEPb1 and a fragment of the 5' untranslated region of GmEPc (−200 to +200) were used as probes. Membranes were washed at 65° C.: 2×15 min in 2×SSPE, 0.1% SDS; 2×15 min in 1×SSPE, 0.1% SDS; 2×15 min in 0.1×SSPE, 0.1% SDS. Autoradiography was performed by exposing membranes to X-ray film at −70° C.

FIGS. 16A, 16B and 16C show the nucleotide and deduced amino acid sequences of GmEPA1, GmEPB1 and GmEPC, respectively. Untranslated sequences are shown in lower case letters. The open reading frames are indicated by upper case letters. The deduced amino acid sequences are shown below the open reading frame in the single-letter code. The putative TATA box and CMT box are shaded. The direct repeats in the 5'-untranslated regions are outlined, and the putative polyadenylation signals (AATAAA/AATAAG) are shown in bold face.

Example 18

Solid-Phase Peroxidase

Peroxidase captured by the said antibody still maintains oxidative activity, therefore antibody bound peroxidase can be immobilized on a solid state matrix (e.g. polystyrene, sepharose column). In oxidative reactions where peroxidase is being used, reagents may be passed through or over immobilized peroxidase and product or modified reagents collected.

Example 19

Non-radioactive Detection of Nucleic Acids

Peroxidase can be covalently conjugated to oligonucleotides. This conjugate can be used as a probe in hybridization assays and in polymerase chain reaction procedures as described in U.S. Pat Nos. 5,254,469 and 5,272,077. The said antibody can be used to purify the oligonucleotide peroxidase conjugate (Example 13). Said antibody may be conjugated with enzyme, such as peroxidase, glucose oxidase, alkaline phosphatase and beta-galactosidase and used in the detection of nucleic acid providing an appropriate chromogen, fluorogen, chemiluminescent or substrate is provided.

Example 20

Oligonucleotide Detection Using Soybean Peroxidase

A method using an anti-peroxidase MAB to detect target oligonucleotides is illustrated in this example. Anonymous human DNA was restriction digested with HindIII and separated on a 0.7% agarose gel. DNA was transferred to nylon membranes by standard protocols. Oligonucleotide probes were synthesized by polymerase chain reaction from pV47-2 using M13 primers. Biotinylated dCTPs were incorporated into the probe by random priming. Biotinylated probe was hybridized to target DNA using standard procedures. Hybridized blots were incubated with nutraavidin conjugated polyclonal antibodies (PAB) against mouse immunoglobulins. An anti-peroxidase MAB having been previously contacted with soybean peroxidase was then bound to the antimouse PAB and the blot incubated in a chemilumescing substrate. Luminescing products were detected by exposure to x-ray film. Alternatively, the anti-peroxidase MAB is bound to the antimouse PAB and then soybean peroxidase is bound to the anti-peroxidase MAB. The detection of bound soybean peroxidase is detected as described.

Example 21

Immunoassay Using Three Antibody System and Soybean Peroxidase

This example illustrates the three antibody system with the use of soybean peroxidase and the superior properties of the assay system. The three antibody system is an immunoassay procedure that takes advantage of triple layer sandwich with a MAB directed against soybean peroxidase. The anti-soybean peroxidase is used to bind soybean peroxidase, rather than conjugating the enzyme to an anti-antibody.

The antibodies used in the validation of the present procedure (SBP system) were MM4, a MAB described by Tong et al. (Blood 69:238, 1987) and developed as an antibody against myeloma cells. The MM4 antibody reacts against fetuin, a widely distributed fetal protein. In preliminary experiments, it was found that the specificity of the MM4 MAB for fetuin is quite strong, leading to the conclusion that MM4 MAB is a useful reagent for the characterization of the SBP system. The antibody against soybean lipoxygenase (Yabuuchi et al., Crop Science 22:333, 1982) is a dioxygenase that is present in soybean seeds.

Fetal bovine serum, a complex mixture consisting of many proteins, was used as a crude fetuin preparation. Purified fetuin was obtained commercially (all chemicals were obtained from Sigma, St. Louis, Mo, unless otherwise indicated). Alpha feto-protein was purified from a human hepatoma cell line using the OM 3-1.1 MAB.

The ELISA procedure was carried out using standard methodology (Chaffin, et al., Infect. Immun. 56:302, 1988; Morrow, et al., In: Colloidal Gold: Principles, Methods and Applications, III, M. Hayat (Ed.) Academic Press, NY, pp.31–57, 1991). Briefly, Nunc Maxisorp Immunoplates (Fisher Scientific, Houston, Tex.) were coated with antigens (concentrations as indicated) and incubated for 24 hours at 4° C. They were blocked with 1% BSA in PBS and incubated for 24 hours at 4° C. They were rinsed thoroughly in PBS plus Tween 20 (0.1%) and incubated with the appropriate antibodies, in each case for 24 hours at 4° C.

Between each incubation the plates were rinsed thoroughly five times in PBS plus Tween. The plates were developed using ortho-phenylene diamine and hydrogen peroxide dissolved in citric acid buffer (pH 4.9), and developed in the dark for 15 minuets until the reaction was terminated through addition of 50 ul of 1 N $H_2SO_4$. The plates were read on an automated ELISA plate reader at an OD of 450 nm.

Immunoblotting was performed according to standard protocols (Xiang, et al., J. Immunol. Meth. 168:275,1994: Morrow, et al., supra; Hirasawa, et al., Biochem. Biophys. Acta 977:150,1989; Hirasawa, et al., Biochem. Biophys. Acta 944:229,1989). Briefly, proteins were separated by PAGE according to Laemmli (Nature 227:680, 1970) using precast gradient minigels (BioRad) and transferred by immunoblotting onto Immulon (Millipore; New Bedford, Mass.) paper in a BioRad transblot transfer cell according to the manufacturer's instructions. Antibody reactive proteins were detected with an ECL Western blotting detection kit (Amersham) according to the manufacturers instructions. The three antibodies were each reacted with the paper by diluting them and incubating each with agitation in the cold for 60 minutes. Between each step the blots were rinsed thoroughly in PBS plus Tween. The blot was then incubated with the ECL reagents for one minute, wrapped in plastic wrap, and pressed against Kodak Xomat LS film for several seconds (times determined empirically).

Figure 10:
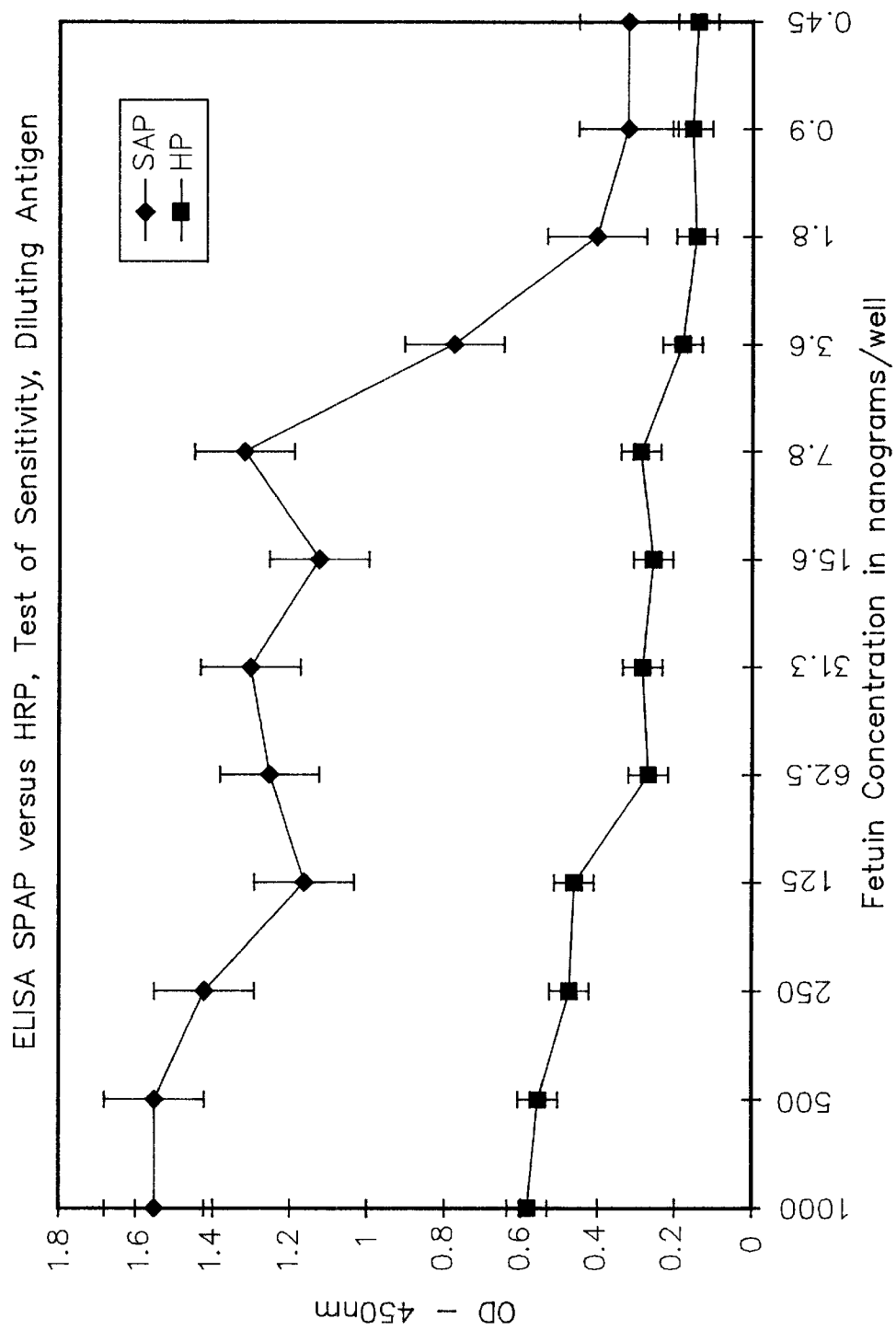
FIG. 10 ELISA results comparing SPAP three antibody system with the horse radish peroxidase (HRP) two antibody system using purified fetuin (antigen) and MM4 MAB. OD readings are averages of four replicates.

The three antibody assay (SPAP) of the present invention was evaluated using ELISA procedures, and comparing the results with a standard two antibody protocol. Dilutions of the antigen, using the fetuin-MM4 system were first tested. As indicated in FIG. 10, as little as 1.8 ng of fetuin antigen with SPAP system was detected, whereas the limit of sensitivity of the standard HRP two antibody method was only around 62.5 ng. Thus, the SPAP system was more than an order of magnitude more sensitive. When the MAB MM4 was omitted or when the second antibody was omitted, there was no interfering activity.

Figure 11A:
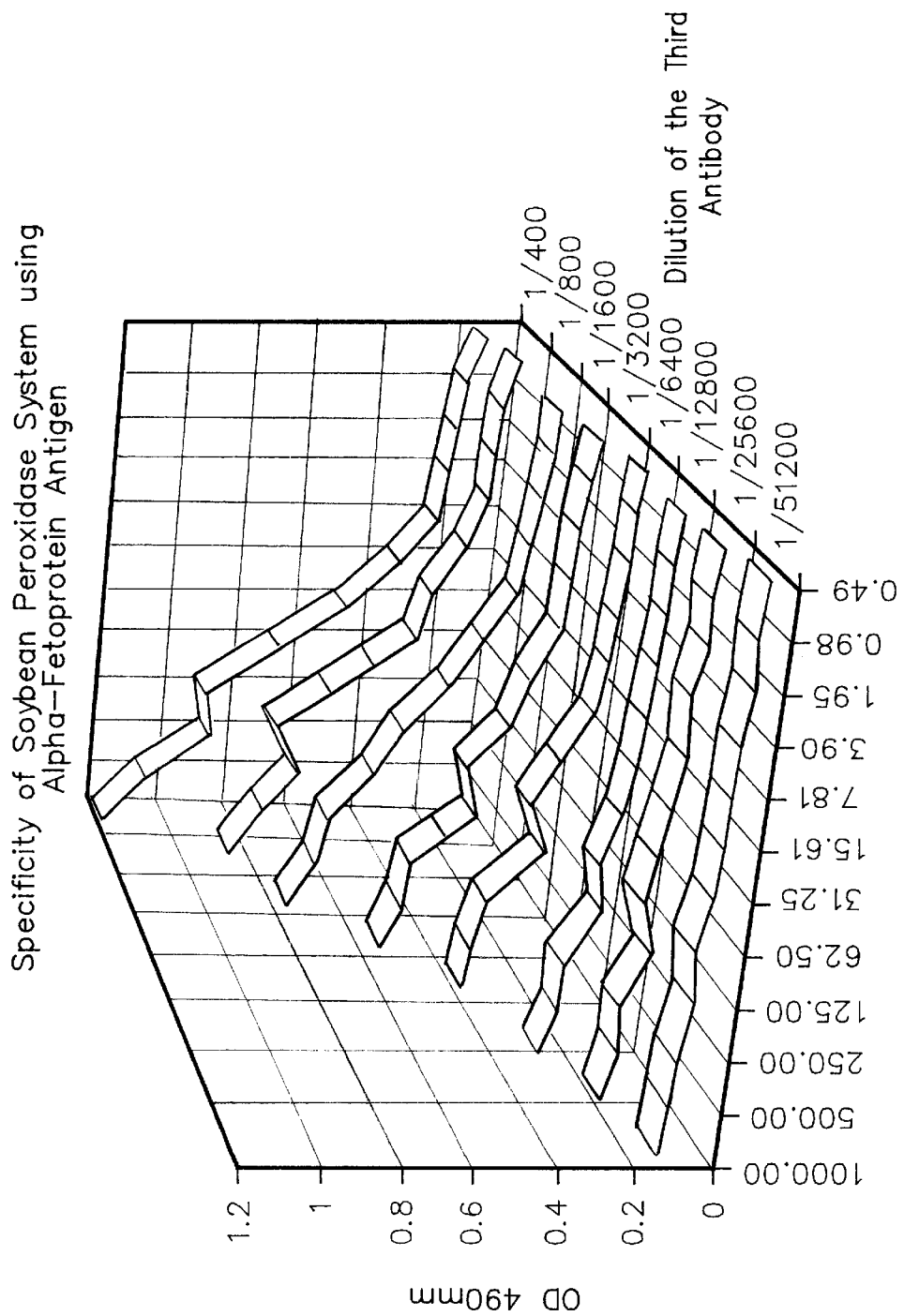
FIG. 11A Three dimensional plot demonstrating effect of varying antigen and third antibody in SPAP system. The range of antigen concentrations was 0.49 to 1000 nanograms/well.
Figure 11B:
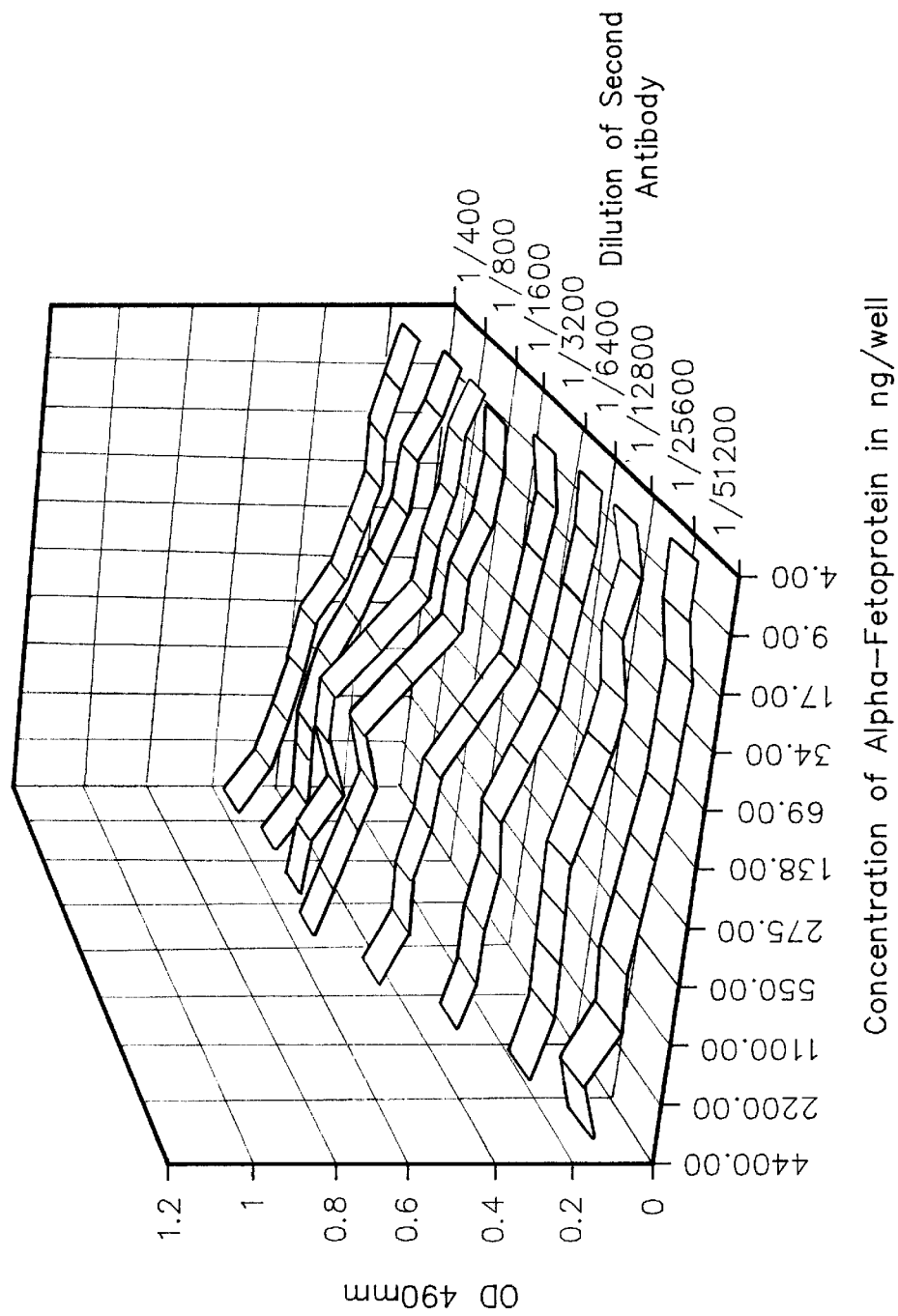
FIG. 11B Three dimensional plot demonstrating effect of varying antigen and second antibody in the conventional two antibody system using conjugated horse radish peroxidase (HRP). The range of antigen concentrations was 4–4400 nanograms/well.

In order to eliminate the possibility that the superior results obtained in the first experiments were a feature of the primary antibody, the two systems were investigated, using alpha-fetoprotein and the OM3 antibody, a totally unrelated system. When the HRP and SPAP systems were compared (FIGS. 11B and 11A, respectively), the SPAP system was superior, giving a stronger signal at every comparable concentrations of antigen than the HRP (FIGS. 11A and 11B).

Figure 12:
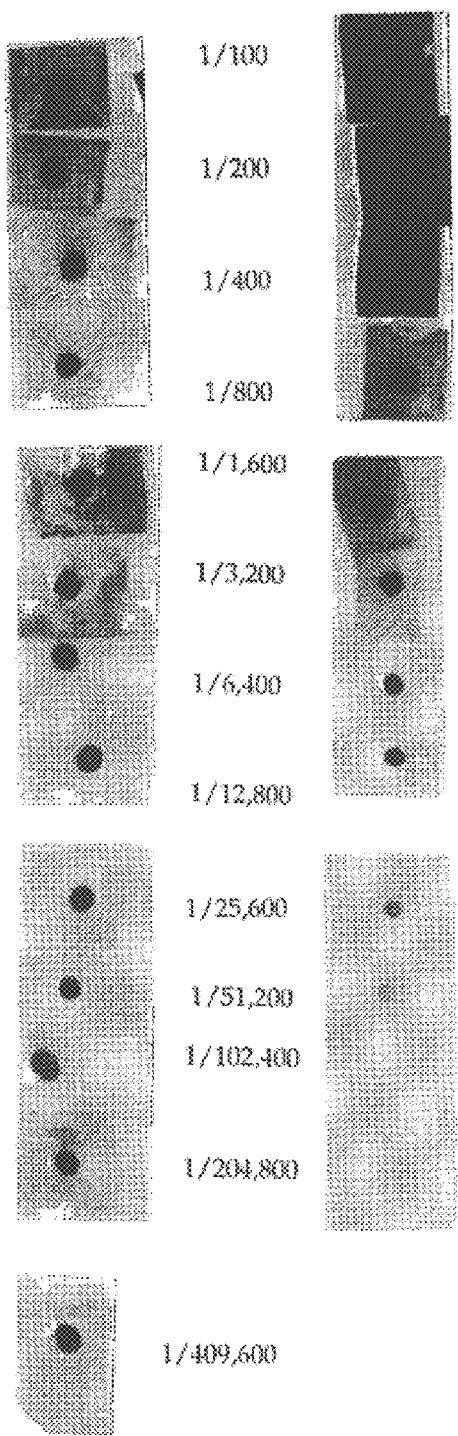
FIG. 12 Immunoblotting procedures using fetuin and MM4 antibody with dot blots used in optimizing antibody concentrations (SPAP on left; HRP on right).

Dot blots were used to determine the best dilution factors and development time. The dot blot data showed the SPAP system have a strong signal with a dilution of 1:409,600 and the HRP system was barely able to detect antigen at a 1:25,600 dilution (FIG. 12). After performing dot blots to optimize the time and dilution factors, an immunoblotting assay was carried out using optimal conditions and the results are shown in FIG. 13. Thus, these results show that the SPAP was at least equal or superior to the HRP reagent. These results suggest that the three antibody system would especially lend itself for kits to be used in field work, and in situations where refreezing is not a practical alternative.

Example 22

Immunoassay Using Non-Conjugated Soybean Peroxidase

A novel technique that uses enzyme anti-enzyme antibody binding instead of antibody enzyme conjugation is described. Crude soybean extracts, containing the lipoxygenase L2 isozyme, were added to microplate wells and incubated overnight at 4 C. and then blocked with a 1% BSA solution. The L2 mouse MAB was used to bind to the mouse L2 enzyme in the sample. A goat antimouse immunoglobulin was used to bind to the mouse L2 antibody. To complete the sandwich, the unconjugated mouse anti-soybean peroxidase MAB was bound to the goat antimouse. Peroxidase solution was added to the well and peroxidase captured by the anti-soybean peroxidase MAB. A chromogenic substrate was added and the oxidized product read at the appropriate wavelength.

Example 23

Identification of Genomic DNA for Soybean Peroxidases

A soybean genomic DNA library was prepared by digesting DNA isolated from soybean with BamHI and XhoI which was chosen on the basis that it did not cut within the cDNA sequence of the peroxidase genes. The digested genomic DNA was inserted into λZapII which had been digested with BamHI and XhoI which was then used to identify the genomic DNA coding for the soybean peroxidases disclosed above. The cDNA specific primers described above were used to search the genomic library. Positive clones were sequenced and the sequences compared with the cDNA sequences set forth in the Sequence Listing to identify genomic DNA which contained the entire coding region of the cDNA. The genomic sequence for GmEPa1 is set forth in FIG. 14 and SEQ ID NO: 18. The ATG start codon at 1392 is underlined. The genomic sequence for GmEPb1 is set forth in FIG. 15 and SEQ ID NO:19. The ATG start codon at 981 is underlined. The genomic sequence for GmEPc is set forth in FIGS. 23A, 23B and 23C and SEQ ID NO:20. The genomic DNA for each of these soybean peroxidases includes the promoter region. Thus, the promoter for GmEPa1 is contained within nucleotides 1 and 1391 of SEQ ID NO:18. The promoter for GmEPb1 is contained within nucleotides 1 and 980 of SEQ ID NO:19. The promoter region for GmEPc is contained within nucleotides 1 and 1532 of SEQ ID NO:20.

Example 24

A Structural Gene Under the Control of Soybean Peroxidase Regulatory Elements The recombinant DNA molecule carrying the desired structural gene under the regulatory control of regulatory elements of the present invention may be introduced into plant tissue by various techniques known to those skilled in the art. The technique used for a given plant species or specific type of plant tissue depends on the known successful techniques. Means for introducing recombinant DNA into plant tissue include, but are not limited to, transformation (Paszkowski et al. (1984) EMBO J. 3:2717–2722), electroporation (Fromm et al. (1985) Proc. Natl. Acad. Sci. USA 82:5824–5828), or microinjection of the DNA (Crossway et al. (1986) Mol. Gen. Genet. 202:179–185) or T-DNA-mediated transfer from Agrobacterium to the plant tissue. Representative T-DNA vector systems are described in the following references: An et al. (1985) EMBO J. 4:277–284; Herrera-Estrella et al. (1983) Nature 303:209–324; Herrera-Estrella et al. (1983) EMBO J. 2:987–995; Herrera-Estrella et al. (1985) in *Plant Genetic Engineering,* Cambridge University Press, New York, pp. 63–93. Once introduced into the plant tissue, the expression of the structural gene may be assayed in a transient expression system, or it may be determined after selection for stable integration within the plant genome. Techniques are known for the in vitro culture of plant tissue, and in a number of cases, for regeneration into whole plants. Procedures for transferring the introduced gene from the originally transformed plant into commercially useful cultivars are known to those skilled in the art.

Production of genetically modified plant tissue expressing a structural gene under the control of regulatory elements and a downstream promoter combines the teachings of the present disclosure with a variety of techniques and expedients known in the art. In most instances, alternate expedients exist for each stage of the overall process. The choice of expedients depends on variables such as the plasmid vector system chosen for the cloning and introduction of the recombinant DNA molecule, the plant species to be modified, the particular structural gene, promoter elements and the regulatory elements used Persons skilled in the art are able to select and use appropriate alternatives to achieve functionality. Culture conditions for expressing desired structural genes in cultured cells are known to the art. Also as is known to the art, a number of both monocotyledonous and dicotyledonous plant species are transformable and regenerable, such that whole plants containing and expressing desired genes under regulatory control of the promoter molecules of this invention may be obtained. As is known to those skilled in the art, expression in transformed plants may be tissue-specific and/or specific to certain developmental stages. Truncated promoter selection and structural gene selection are parameters which may be optimized to achieve desired plant expression, all as known to those skilled in the art and as taught herein.

Example 25

Construction of Gene Expression Vectors for Transient Assay

The expression vector psmRS-GFP (red form of gellyfish protein), containing the CaMV35S-smRS-GFP-NosT fragment, was kindly provided by Dr. Greg Martin. A Hind III/EcoR I fragment from pBI 121 (Clontech), containing the 35S promoter, the β-glucuronidase (GUS) gene and nos (nopaline synthase gene) terminator, was cloned between the Hind III and EcoR I site of psmRS-GFP.

The 1391 bp 5'-upstream region of the GmEPA1 gene (−1391 to −1) and the 1524 bp 5'-upstream region of the GmEPC gene (−1525 to −1) were PCR amplified using Pwo DNA polymerase (Boehringer-Mannheim), which has inherent 3' to 5' exonuclease proof-reading activity and produces blunt-ended products. The fragments were cloned into pT7Blue(R) (Novagen) at EcoR V site. The Sal I/BamH I fragment of the GmEPA1 promoter and the HindIII/BamH I fragment of the GmEPC promoter in pT7Blue (R) were ligated upstream of the GUS gene in psmRS-GFP to generate the GUS expression constructs containing the GmEPA1 and GmEPC promoters.

Example 26

Construction of Promoter Deletion Clones

Expand™ Long Template PCR system (Boehringer-Mannheim) was utilized to create the −1525, −1074, −467 and −207 promoter deletion constructs. The same downstream primer was located 190 bp downstream after the translation stop codon. The PCR products were cloned into pCR(®)-XL-TOPO (Invitrogen).

Example 27

Particle Bombardment

Gold particles (1 μM diameter, BIO-RAD) were coated with plasmid DNA by co-precipitation in the presence of ethanol, $CaCl_2$ and spermidine (5 μg DNA/mg gold particle). A helium-gas-driven device (PDS 1000/He, BIO-RAD) was used. For tissue-specific expression assay of GmEPC promoter, ten μg of plasmid DNA containing GmEPC promoter and GUS and ten μg of plasmid DNA containing 35S and psmRF-GFP were co-bombarded into leaves, roots and immature soybean seed coats (Resnik, EpEp). For promoter deletion analysis, twenty μg of DNA of each construct were bombarded into immature seed coats (Pella 86, epep). For specific-expression assay of GmEPA1 promoter, ten μg of plasmid DNA containing GmEPA1 promoter and GUS were bombarded into seed coats and roots. The samples were bombarded at an accelerating pressure of 1100 psi. After bombardment, samples were covered by two layers of wet paper. Control samples were likewise bombarded with empty plasmid-coated particles. Two to four experiments were conducted for each plasmid construct.

Example 28

GUS, RF-GFP and Peroxidase Activity Assay

After a 24 h room temperature incubation in the dark, bombarded roots, seed coats and leaves (500–800 mg) were homogenized in liquid nitrogen and 500 μl of extraction buffer (1×PBS, 1 mM DDT, 100 μg/ml PMSF) was added, and centrifuged at 12,000 rpm for 15 min at 40° C. Total protein was quantified using the Bio-Rad DC Protein Assay Kit (Lowry method). Flourescence of 4-methylumbellierone (4-MU) produced by cleavage of 4-methylumbelliferyl-β-D-glucuronic acid (MUG) was measured to quantitate GUS activity. The extracts (50 μg protein) were assayed by 1 mM MUG in extraction buffer. The reaction was incubated at 37° C. for 30 min and terminated with the addition of 0.2 M $Na_2CO_3$. Fluorescence was emitted with excitation at 365 nm and its strength at 455 nm was calibrated using spectrofluorophotometer. RF-GFP was emitted with excitation at 495 nm and its strength at 530 nm was calibrated. For peroxidase activity assay, bombarded seed coats were immersed in 500 μl of water overnight at 40° C. The protein concentration was determined as above. Peroxidase activity was monitored using tetramethyl-benzadine as a substrate (Vierling and Wilcox, 1996). The reaction was stopped by the adding of 1M $H_2SO_4$, and the plate was read at $OD_{405}$ nm. Seed coat and root were also assayed for GUS activity in situ after 24 h by incubation overnight at 37° C. in 100 mM sodium phosphate buffer, pH 7.0, containing 0.5 mM potassium ferricyanide, 0.5 mM potassium ferrocynide and 1 mM X-Gluc, then washing in 70% (v/v) ethanol.

Example 29

Extraction of Nuclear Proteins

Twenty grams of immature seed coats, leaves and roots were homogenated in liquid nitrogen and 100 ml of ice-cold Honder buffer was added (Honder buffer: 50 mM Tris-acetate pH 8.5, 5 mM magnesium-acetate, 0.25 M sucrose, 5% dextran 40, 2.55 Ficoll 400, 2.8 mM 2-mercaptoenthanol). The homogenate was filtered through two layers of cheese-cloth and centrifuged at 3000 g for 10 min. The nuclear pellet was suspended with 20 ml of ice-cold nuclear wash buffer (50 mM Tris-acetate, pH 8.5, 5 mM magnesium-acetate, 0.3 M sucrose, 0.5 mM EDTA, 0.1 mM PMSF, 2.8 mM 2-mercaptoethanol) and centrifuged as before. The pellet was gently resuspended in 10 ml Honder buffer and layered onto two-step Percoll gradients (10 ml 50% Percoll in Honder buffer: 5 ml 20% Percoll in Honder buffer). Gradients were centrifuged for 30 min at 8500 g. The interface between 20% and 50% was collected, diluted to 12 ml with Honder buffer, and centrifuged at 4000 g for 10 min. The nuclei were resuspended in nuclear extraction buffer (20 mM Tris-acetate, pH 8.5, 5 mM magnesium-acetate, 25% glycerol, 1 mM EDTA, 0.1 mM PMSF, 10 mM 2-mercaptoethanol) followed by the addition of 2.5 M KCl to a final concentration of 0.46 M and incubated on ice for 30 min. The nuclear extract was collected after centrifugation for 30 min at 12000 g. The extract was then dialyzed against 500 ml dialysis buffer (20 mM Tris-HCl, pH 8.0, 100 mM KCl, 0.2 mM EDTA, 0.5 mM DTT, 0.2 mM PMSF, 25% glycerol) at 4° C. overnight. The extract was then centrifuged for 30 min at 12000 g and the supernatant was collected. Nuclear protein concentration was determined using Bio-Rad DC Protein Assay Kit. The nuclear extract was divided into small aliquots, frozen in liquid nitrogen and stored at –80° C.

Example 30

DNA Probes and Gel Retardation Assay

Gel retardation assay has been used in gene expression regulation studies (Dorn et al., 1987; Dunn et al., 1998). In our preliminary gel retardation assay, two fragments (A2 and A5) in GmEPA1 promoter and two fragments (C4 and C6) in GmEPC promoter were identified that interact with seed coat nuclear proteins. A2 and A5 do not compete with C4 and C6 for the same nuclear factors and therefore different nuclear factors may be involved in the controls of GmEPA1 and GmEPC expression. The overall gel retardation assay results indicated that at least two regulatory elements located at two spatially separated regions of these two gene promoters are involved in their expression controls. Methods known in the art, such as DNA footprinting may be used to pinpoint the core elements that bind nuclear proteins.

Gel retardation assays were conducted with radio-labeled DNA fragments spanning the intact GmEPA1 and GmEPC promoters. PCR (Pwo polymerase), coupled with Dde I and Nla III digestions, was used to obtain smaller promoter fragments. The promoter fragments were dephosphorylated with calf intestinal dephosphorylase and end labeled with $[\gamma-^{32}P]dATP$ by T4 polynucleotide kinase. The labeled DNA was then purified through a G50 column (Pharmacia).

The binding reaction was carried out in a final volume of 20 μl containing 20 mM Tris-HCl, pH 8.0, 1 mM EDTA, 7.5 mM $MgCl_2$, 1 mM DTT, 5% glycerol, 3 μg of poly dI-dC to eliminate non-specific DNA-protein interactions. About 5 μg of nuclear protein was added to the mixture and the mixture was preincubated at room temperature for 5 min. The end-labeled probes were then added and the mixture was further incubated at room temperature for 15 min. The binding products were loaded onto 5% polyacrylamide gels containing 0.5× TBE buffer. The gels were run at a constant 12.5V/cm for 3 h with circulation of the electrophoresis buffer. After electrophoresis, gels were dried onto 3M paper and autoradiographed at –80° C.

Example 31

Structures of Genes for Soybean Peroxidases

The deduced amino acid sequences from GmEPA1, GmEPB1 and GmEPC (FIGS. 16A–C) were virtually identical to those deduced from cDNA GmEPa1, GmEPb2 and GmEPc, except that there was a single amino acid residue difference between GmEPb2 and GmEPB1. All three genes consist of three introns and four exons. The intron-exon organizations of these three genes are summarized in Table 1. Exons II and III in GmEPA1 and GmEPB1 are the same size and 3-bp shorter than those in GmEPC. Exons I, IV, and the three introns in all the three genes were of different sizes.

All introns are AT-rich and have splicing consensus GT and AG at 5' and 3' ends, respectively (FIGS. 16A, 16B and 16C). GmEPA1, GmEPa1, GmEPB1, GmEPb1, GmEPC and GmEPc encode for the same peroxidase isoform.

TABLE 1

Intron-exon organizations of GmEPA1, GmEPB1 and GmEPC

|  | Introns (bp) | | | Exons(bp) | | | |
| --- | --- | --- | --- | --- | --- | --- | --- |
|  | I | II | III | I | II | III | IV |
| GmEPA1 | 94 | 137 | 514 | 204 | 189 | 163 | 418 |
| GmEPB1 | 109 | 143 | 104 | 207 | 189 | 163 | 383 |
| GmEPC | 631 | 1030 | 263 | 219 | 192 | 166 | 479 |

Example 32

The Promoter Sequences of GmEPA1, GmEPB1 and GmEPC

The characteristics of the three promoters are summarized in FIGS. 16A, 16B and 16C.

Putative TATA and CAAT boxes were found at –36, –106 and –248. There are four directed repeats at –65/–344 (ACTATTTG), –623/–966 (ATGATATAT), –667/–930 (TCAAGGATT) and –1116/–1144 (TTCAATGGCTATACCT). The 980-bp promoter region in GmEPB1 has 67% A and T bases, and putative TATA and CMT boxes were located at –9, –79 and –96, respectively. Three directed repeats were at –156/–377 (ACTACTCTTGA), –280/–659 (ATAAAAAAAAAA) and –737/–798 (ACTTTTTTAT). The 1524-bp 5' upstream region in GmEPC contains 73% A and T bases. Putative TATA and CMT boxes were at –31, –47, –176 and –248. The four directed repeats in this region were at –14/–309 (CATATTAAC), –321/–459 (GTGCTCCMCCA), –677/–880 (AATGAATGTTT), and –1404/–1454 (ATTATCGACATAATT). The activation sequence 1 (as1) (TGACG) of the cauliflower mosaic virus 35S promoter (CaMV 35S) was present at –463. A G-box-like sequence (GACGTG) also was present at –462 in GmEPC promoter.

Example 33

Estimation of the Copy Numbers of the Three Genes

Figure 24:
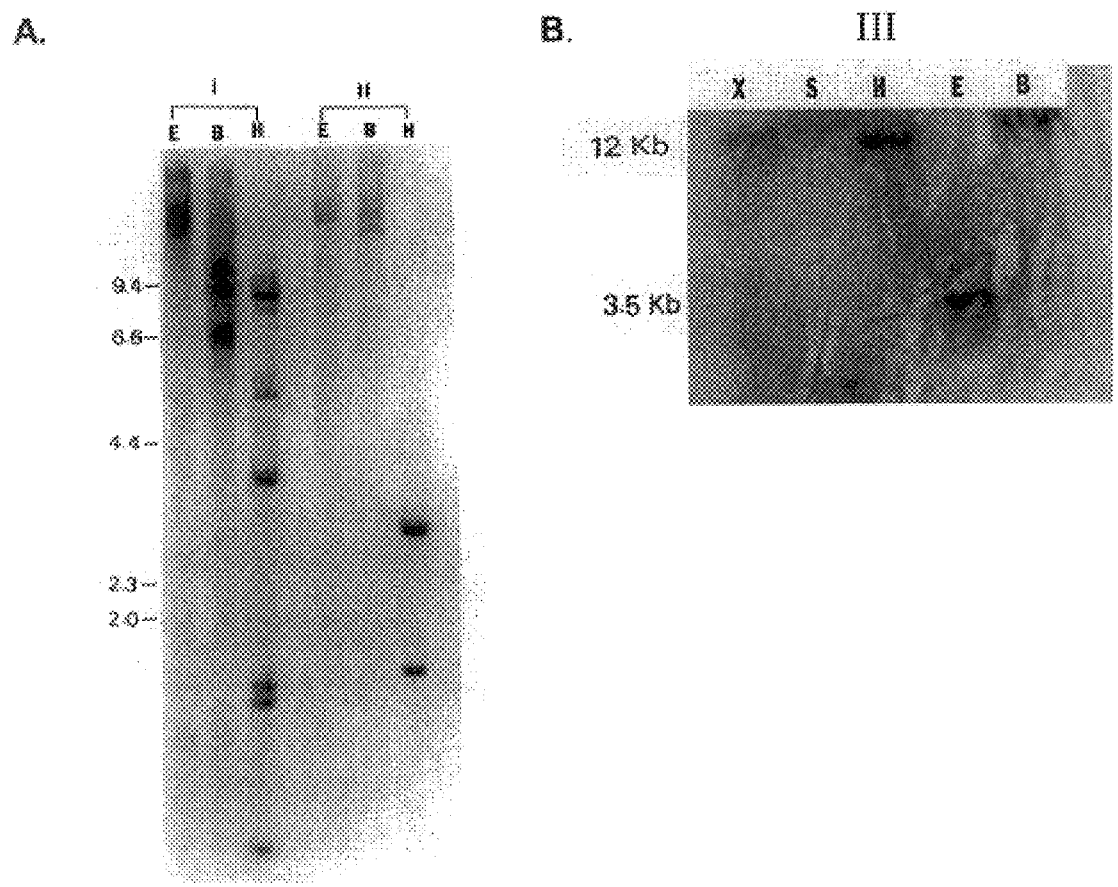
FIGS. 24A–B Shows Southern blot analysis of soybean genomic DNA probed with GmEPa1 (I), GmEPb1 (II) and a 1180 bp fragment (–207/973) from the 5' flanking region of GmEPC (III). DNA digestion was performed with BamH1 (B) EcoR1 (E) HindIII (H), Xba1 (X), or Sac1 (S).

Genomic Southern blot analysis was performed to estimate the number of GmEPA1, GmEPB1 and GmEPC genes in the diploid soybean genome (FIGS. 24A and 24B). When the full length cDNA of GmEPa1 and GmEPb1 were used as probes, a few bands were obtained with BamH I, EcoR I, or Hind III digested genomic DNA in each case. No cross-hybridization was detectable between the two probes under the hybridization and washing conditions. An 1180 bp fragment at the 5' region (–207 to 973) of GmEPC was used to probe the genomic DNA digested with Xba I, Sac I, Hind III, EcoR I and BamH I. It was apparent that only a very small number of these three genes, possibly only one of GmEPB1 and GmEPC, are present in the soybean genome.

Example 34

Comparison with Other Plant Peroxidase Genes

FIG. 17 shows the comparison of gene structures between soybean peroxidase and other plant peroxidases. The soybean peroxidase genes are similar in structure to the *A. thaliana,* horseradish and rice genes, with three introns located at the responding positions. They are different though from the wheat and tomato peroxidase genes, which have two introns. Thus, the number of introns in peroxidase genes is not conserved. The three introns in GmEPA1, GmEPB1 and GmEPC have GT and AG consensus bases at their 5' and 3' splicing sites (Roberts and Kolattukudy, 1989; Intapruk et al., 1991; Baga et al., 1995). They were located in regions that encode for the most conserved domains of peroxidase (FIG. 17) and therefore do not indicate any correlation between exons and units of protein structures. However, the position of the introns in relation to the reading frames was totally conserved within the peroxidase genes mentioned above. The nucleotide sequences of the introns have greatly diverged and show no similarity.

Example 35

Analysis of Promoter Function of GmEPA1 and GmEPC

The gene constructs shown in Table 2 were made and cloned into pUC 118 to test the promoter function of GmEPA1 and GmEPC.

TABLE 2

Promoter construct for transient expression assays.

| | |
| --- | --- |
| Construct A: | Promoter A1 (1391 bp) + GUS + nos |
| Construct B: | Promoter C (1524 bp) + GUS + nos |
| Construct C: | Promoter 35S + RF-GFP + nos |
| Construct CK: | pUC 118 |

Figure 18:
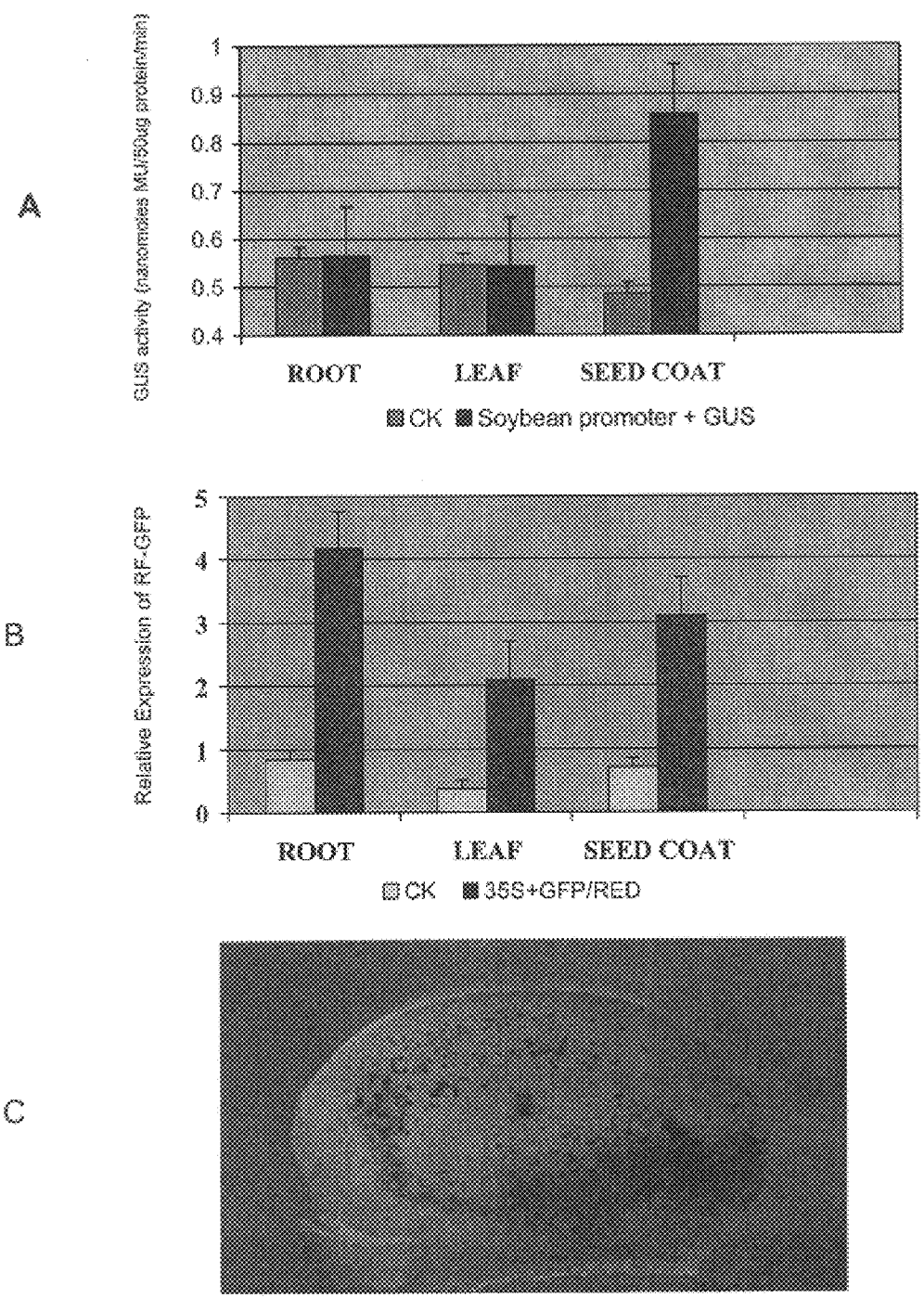
FIGS. 18A–C Analysis of promoter function of GmEPC. Shows GUS activity and RF-GFP activity after co-bombardment with constructs B and C (Table 2), 18A and 18B, respectively. 18C shows transient expression of GUS in developing soybean seed coat.

Constructs B and C were co-bombarded into roots, leaves and immature seed coats. After overnight incubation of the bombarded tissues in dark, total proteins were extracted. GUS (FIG. 18A) and RF-GFP (FIG. 18B) activities were measured simultaneously. Plasmid pUC118 was used to as a control (CK) to mimic the bombardment, and GUS and RF-GFP activities were also measured. The bombardment of construct B alone showed the transient expression of GUS in soybean developing seed coat (FIG. 18C). FIG. 18A indicates that the 1524-bp promoter (Construct B) of GmEPC was capable of driving the expression of GUS and GUS activity was only observed in seed coats. Deletion analysis of this promoter (FIG. 19) showed that there was a sharp decrease in the peroxidase activity in seed coats when the portion from –467 to –207 was deleted. The deletion from –1524 to –467 did not have much affect on peroxidase activity.

Construct A was bombarded into seed coats and roots and GUS activity was assayed histochemically after 24 h. FIGS. 20A and 20B show that the 1391-bp promoter of GmEPA1 (Construct A) was able to drive the expression of GUS in roots and seed coats by transient expression assay.

Example 36

Promoter Deletion Analysis of GmEPC

The long-range PCR and the entire seed coat peroxidase gene were used to make the D1, D2, D3, and D4 deletions. The primer at the 3'-untranslated region (143-bp downstream the translation stop codon), and primers at positions –1525, –1074, –467, and –207 were synthesized (FIG. 19A). PCR products were cloned into pCR-XL-TOPO (Invitrogen), and used for bombardment. Soybean cultivar Pella 86 (epep) was used for peroxidase transient expression assay. After overnight incubation of the bombarded seed coats, peroxidase was extracted, quantified and peroxidase activity was measured using tetramethyl-benzadine as a substrate. The reaction was stopped by the addition of 1M $H_2SO_4$, and the plate was read at $OD_{405}$ (FIG. 19B).

Example 37

Identification of Promoter Fragments that Interact with Nuclear Protein Factors

Figure 21D:
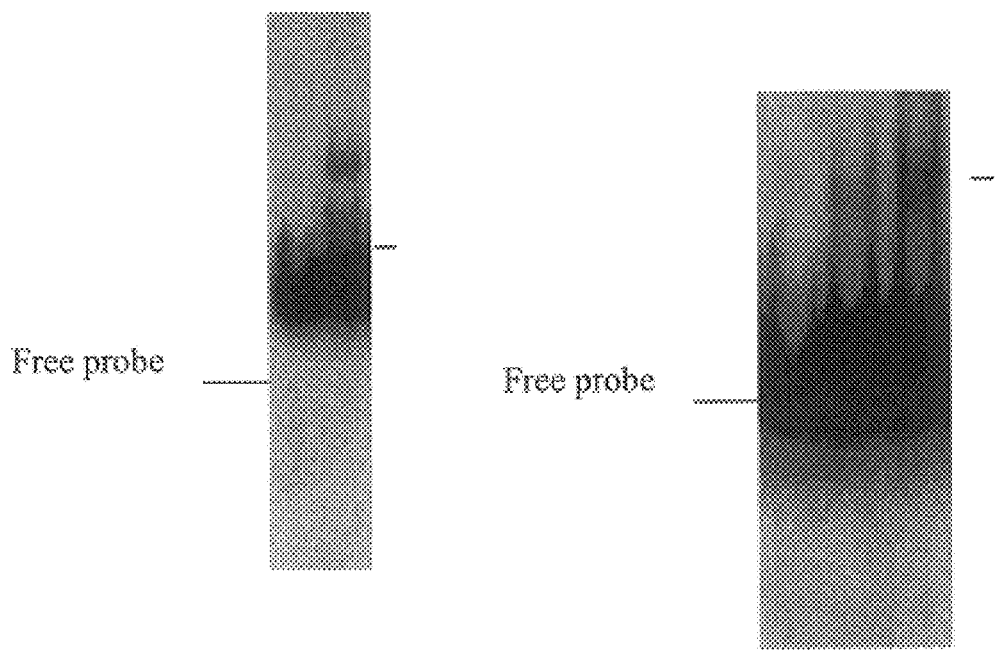

As a first step in understanding the mode of regulation of the seed coat-expressed peroxidase genes, we used a gel retardation assay to investigate possible interactions between nuclear extracts from different tissues and GmEPA1 and GmEPC promoter fragments. Six GmEPA1 promoter fragments were generated by PCR. Six GmEPC promoter fragments were generated by PCR and Dde I digestion. About 2 ng of each $^{32}$P-labeled probe (~20,000 cpm) was incubated with approximately 5 µg of nuclear proteins from developing seed coats (absence of nuclear extract is indicated as "–" in FIGS. 21C and D). Each reaction also included 3 µg of poly(dl-dC) as non-specific DNA competitors. An initial survey to assay the capacity of these promoter fragments to bind nuclear proteins from seed coats revealed that fragments A2 (–1071 to –857) and A5 (–372 to –203) of GmEPA1 (FIG. 21A), fragments C4 (–467 to –310) and C6 (–207 to –1) of GmEPC (FIG. 21B), were capable of forming stable DNA-protein complexes in the presence of excess poly(dl-dC) (FIGS. 21C and 21D). Fragment A5 displayed two DNA-protein complexes. Multiple soybean nuclear fragments interacted with the GmEPA1 and GmEPC promoters.

Figure 22:
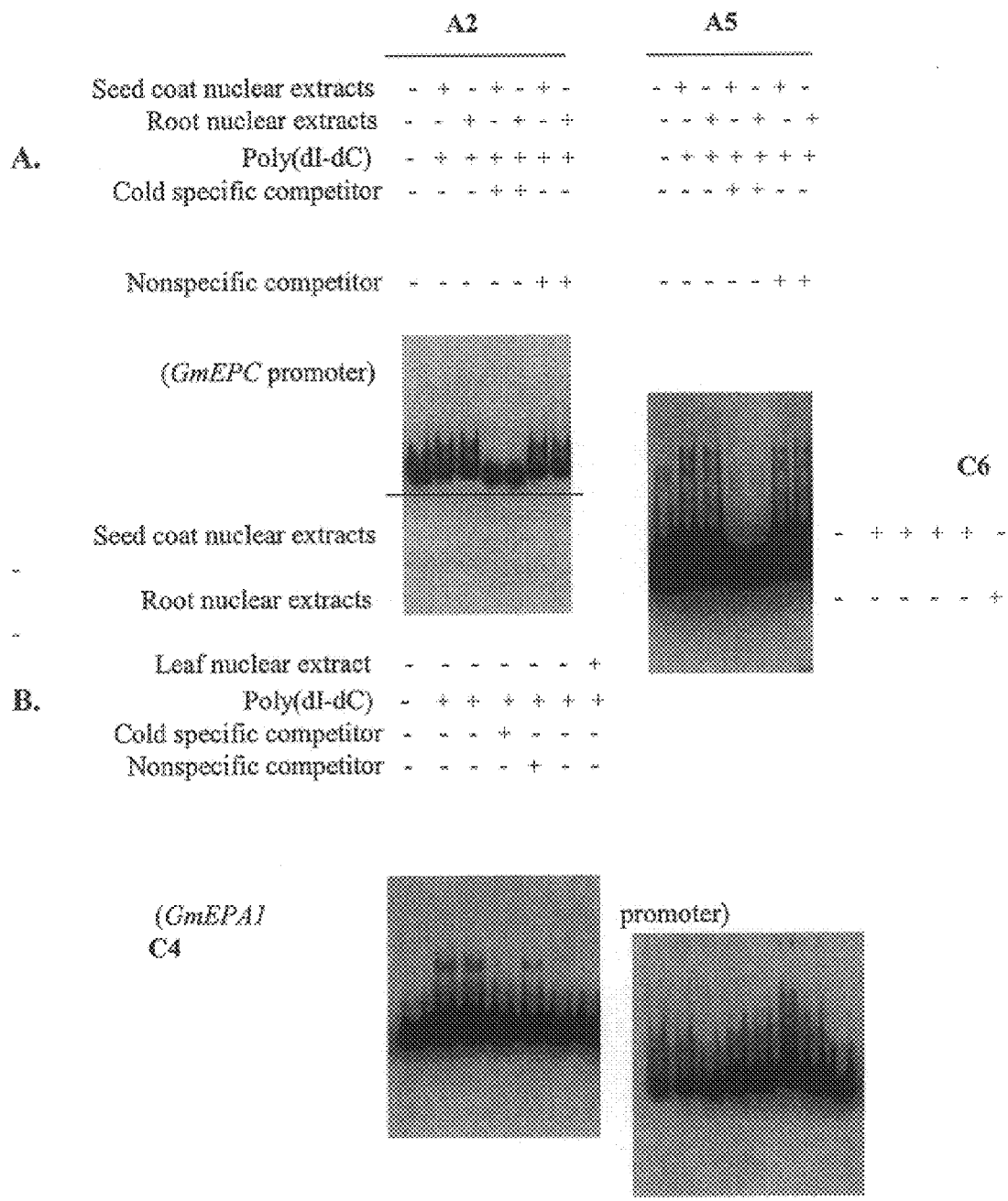
FIGS. 22A–B Shows sequence specificity of DNA-protein complexes between seed coat or root nuclear extracts and promoter fragments of GmEPA1 (FIG. 22A) and GmEPC (FIG. 22B). Other conditions were as described for FIG. 21.

To assess the sequence-specificity of these binding activities, competitive gel retardation experiments were performed. FIG. 22A shows that DNA-protein complexes were formed when fragments A2 and A5 were incubated with root nuclear proteins. The formation of these complexes were prevented when approximately 100-fold of unlabeled A2 and A5 (specific competitors) were included in the binding reactions. Promoter fragments of GmEPC do not compete with A2 and A5 for the same nuclear protein factor(s). FIG. 22D shows that unlabeled fragment C6 competed with labeled C6 for the same nuclear protein factors and no DNA-protein complex was observed when fragment C6 was incubated with root and leaf nuclear extracts. Complex between fragment C4 and seed coat nuclear proteins observed in the initial survey (FIG. 21D) was not reproducibly observed in the competitive gel retardation assay (FIG. 22B).

Example 38

Construction of Vectors and Transformation of Soybean

Promoter sequences necessary for the highest expression may be fused to the coding region of value-added proteins, for example, monoclonal antibodies or autoantibody epitopes. These expression cassettes may be inserted into the appropriate vectors for Agrobacterium mediated transformation of soybean (U.S. Pat. No. 5,376,543). Transgene expression may be analyzed by methods known in the art.

Example 39

Construction of Plasmids Used in Transformation of Plants

A promoter sequence may be designed with homology to the promoters of the present invention. The sequence may be based on homologies found in the database at the time of design by comparing bases of promoters of the present invention to known plant DNA sequences. Regions of homologies may be aligned using the promoters of the present invention as the template and bases changed to maintain the desired level of homology. This homology sequence may be synthesized and used to replace the promoter in an appropriate plasmid by methods known in the art.

Agrobacterium-mediated DNA delivery may then be used to produce stable transformants carrying the promoter construct driving a gene of choice.

While the invention has been disclosed in this patent application by reference to the details of the preferred embodiments of the invention, it is to be understood that this disclosure is intended in an illustrative rather than a limiting sense, as it is contemplated that modifications will readily occur to those skilled in the art, within the spirit of the invention and the scope of the appended claims.

REFERENCES

Abraham W T and Bristow M R (1997). *Circulation* 96:2755–2757.
Altschul S F, et al. (1997). *Nucl. Acids Res.* 25:3389–3402.
Anand R (1992). *Techniques for the Analysis of Complex Genomes*, (Academic Press).
Anderson W F, et al. (1980). *Proc. Natl. Acad. Sci. USA* 77:5399–5403.
Ausubel F M, et al. (1992). *Current Protocols in Molecular Biology*, (J. Wiley and Sons, N.Y.)
Baga, M., Chibbar, R. N. and Kartha, K. K., (1995). *Molecular cloning and expression analysis of peroxidase genes from wheat*. Plant Molecular Biology, 29:647–662.
Bandyopadhyay P K and Temin H M (1984). *Mol. Cell. Biol.* 4:749–754.
Bartel P L, et al. (1993). "Using the 2-hybrid system to detect protein-protein interactions." In *Cellular Interactions in Development: A Practical Approach*, Oxford University Press, pp. 153–179.
Beaucage S L and Caruthers M H (1981). *Tetra. Letts.* 22:1859–1862.
Berglund P, et al. (1993). *Biotechnology* 11:916–920.
Berkner K L (1992). *Curr. Top. Microbiol. Immunol.* 158:39–66.
Berkner K L, et al. (1988). *BioTechniques* 6:616–629.
Borman S (1996). *Chemical & Engineering News*, December 9 issue, pp. 42–43.
Bowles K R, Gajarski R, Porter P, Goytia V, Bachinski L, Roberts R, Pignatelli R and Towbin J A (1996). *J. Clin. Invest.* 98:1355–1360.
Breakefield X O and Geller A I (1987). *Mol. Neurobiol.* 1:339–371.
Brinster R L, et al. (1981). *Cell* 27:223–231.
Buchschacher G L and Panganiban A T (1992). *J. Virol.* 66:2731–2739.
Bustos, M. M., Guiltinan, M. J., Jordano, J., Begum, D., Kalkan, F. A., and Hall, T. C., (1989). *Regulation of β-glucuronidase expression in transgenic tobacco plants by an A/T-rich, cis-acting sequence found upstream of a french bean β-phaseolin gene*. Plant Cell, 1:839–853.
Capecchi M R (1989). *Science* 244:1288.
Cariello NF (1988). *Am. J. Human Genetics* 42:726–734.
Chee M, et al. (1996). *Science* 274:610–614.
Chee, P. P. and J. L. Slighton, 1996. *Transformation of soybean (Glycine max) via Agrobacterium tumefaciens and Analysis of Transformed Plants*, Methods in Molecular Biology, eds. Gartland K M A and M R Davey, pp. 101–119, Humana Press, Totowa, N.J.

Chee, P. P., K. A. Fober and J. L. Slighton, 1989. *Transformation of Soybean (Glycine max.) by Agrobacterium Tumefaciens*. Plant Physiol. 91:1212–1218.

Chen, H. and R. A. Vierling, 1998. *Molecular Cloning and Characterization of Soybean Peroxidase Gene Families*. Plant Science in press.

Chen, H. and R. A. Vierling, 1998. *Structure and Promoter Analysis of the Soybean Seed Coat Peroxidase Gene*. Plant Molecular Biology in review.

Chevray P M and Nathans D N (1992). *Proc. Natl. Acad. Sci. USA* 89:5789–5793.

Compton J (1991). *Nature* 350:91–92.

Conner B J, et al. (1983). *Proc. Natl. Acad. Sci. USA* 80:278–282.

Costantini F and Lacy E (1981). *Nature* 294:92–94.

Cotten M, Langle-Rouault F, Kirlappos H, Wagner E, Mechtler K, Zenke M, Beug H and Birnstiel M L (1990). *Proc. Natl. Acad. Sci. USA* 87:4033–4037.

Cotton R G, Rodrigues N R and Campbell R D (1988). *Proc. Natl. Acad. Sci. USA* 85:4397–4401.

Culver K (1996). *Gene Therapy: A Primer for Physicians*, 2nd Ed., Mary Ann Liebert.

Curiel D T, et al. (1991). *Proc. Natl. Acad. Sci. USA* 88:8850–8854.

Curiel D T, et al. (1992). *Hum. Gene Ther.* 3:147–154.

De Neve, M., M. DeLoose, A. Jacobs, H. Van Houdt, B. Kaluza, U. Weidle and M. Wan Montagu, 1993. *Assembly of Antibody and its Derived Antibody Fragment in Nicotiana and Arabidopsis*. Transgenic Res. 2:227–237.

Dec G W and Fuster V (1994). *N. Engl. J. Med.* 331:1564–1575.

DeRisi J, Penland L, Brown P O, Bittner M L, Meltzer P S, Ray M, Chen Y, Su Y A and Trent J M (1996). *Nat. Genet.* 14:457–460.

Deutscher M (1990). *Meth. Enzymology* 182 (Academic Press, San Diego, Calif.).

Donehower L A, et al. (1992). *Nature* 356:215.

Dorn, A., Bollekens, J., Stabu, A., Benoist, C. and Mathis, D., (1987). *A multiplicity of CCAAT box-binding proteins*. Cell 50(11):863–872.

Du Bois D and Du Bois E F (1916). *Arch. Intern. Med.* 17:863.

Dunn, M. A., White, A. J., Vural, S. and Hughes, M. A., 1998). *Identification of promoter elements in low-temperature-responsive gene (blt4.9) from barley (hordeum vulgare L.)*. Plant Molecular Biology, 38:551–564.

During, K., S. Hippe, F. Kreuzaler and J. Schell, 1990. *Synthesis and Self-Assembly of a Functional Antibody in Transgenic Nicotiana Tabacum*. Plant Mol. Biol. 15:281–293.

Editorial (1996). *Nature Genetics* 14:367–370.

Elghanian R, et al. (1997). *Science* 277:1078–1081.

*Enhancers and Eukaryotic Gene Expression*, Cold Spring Harbor Press, Cold Spring Harbor, N.Y. (1983).

Erickson J, et al. (1990). *Science* 249:527–533.

Fahy E, Kwoh D Y and Gingeras T R (1991). *PCR Methods Appl.* 1:25–33.

Feigner P L, et al. (1987). *Proc. Natl. Acad. Sci. USA* 84:7413–7417.

Fields S and Song O-K (1989). *Nature* 340:245–246.

Fiers W, et al. (1978). *Nature* 273:113–120.

Fink D J et al. (1996). *Ann. Rev. Neurosci.* 19:265–287.

Fink D J, et al. (1992). *Hum. Gene Ther.* 3:11–19.

Finkelstein J, et al. (1990). *Genomics* 7:167–172.

Fobert, P. and Labbe, H., (1994). *T-DNA Tagging of a seed coat specific cryptic promoter in tobacco*. The Plant J., 6(4):567–577.

Fodor S P A (1997). *Science* 277:393–395.

Freese A, et al. (1990). *Biochem. Pharmacol.* 40:2189–2199.

Friedman T (1991). *In Therapy for Genetic Diseases*, T. Friedman, ed., Oxford University Press, pp. 105–121.

Fujiyama, K., Takemura, H., Shibayama, S., Kobayashi, K., Choi, J. K., Shinmyo, A., Takano, M., Yamada, Y. and Okada, H., (1988). *Structure of the Horseradish Peroxidase Isozyme C Genes*. Eur. J. Biochem. 173:681–687, Fujiyama, K., Takemura, H., Shinmyo,A., Okada, H. and Takano, M., (1990) *Genomic DNA Structure of Two New Horseradish Peroxidase Encoding Genes*. Gene 89:163–169.

Gijzen, M., (1997) *A Deletion Mutation at the ep locus Causes Low Seed Coat Peroxidase Activity in Soybean*. The Plant J., 12(5):991–998.

Gimona M, Vandekerckhove J, Goethals M, Herzog M, Lando Z and Small J V (1994). *Cell Motil. Cytoskeleton* 27:108–116.

Glover D (1985). *DNA Cloning, I and II* (Oxford Press).

Goding (1986). *Monoclonal Antibodies: Principles and Practice*, 2d ed. (Academic Press, N.Y.).

Godowski P J, et al. (1988). *Science* 241:812–816.

Goldberg, R. B., (1986). *Regulation of Plan Gene Expression*. Phil. Trans. R. Soc. Lond. B., 314:343–353.

Gordon J W, et al. (1980). *Proc. Natl. Acad. Sci. USA* 77:7380–7384.

Gorziglia M and Kapikian A Z (1992). *J. Virol.* 66:4407–4412.

Graham F L and van der Eb A J (1973). *Virology* 52:456–467.

Gregorio C C (1997). *Cell Struct. Funct.* 22:191–195.

Grompe M (1993). *Nature Genetics* 5:111–117.

Grompe M, et al. (1989). *Proc. Natl. Acad. Sci. USA* 86:5855–5892.

Guillen, P., Debon, R. M., Grasser, K. D., Harrsch, P., Grimm, R., Ponte, I and Palau, J., *Isolation and characterization of a 28-kDa HMG-like protein that binds to A/T-rich distal promoter regions of zein genes*. Plant Sci., 1998, 135:31–38

Guthrie G and Fink G R (1991). *Guide to Yeast Genetics and Molecular Biology* (Academic Press).

Hacia J G, et al. (1996). *Nature Genetics* 14:441–447.

Hamada H, Petrino M G and Kakunaga T (1982). *Proc. Natl. Acad. Sci. USA* 79:5901–5905.

Harlow E and Lane D (1988). *Antibodies: A Laboratory Manual* (Cold Spring Harbor Laboratory, Cold Spring Harbor, N.Y.).

Hasty P K, et al. (1991). *Nature* 350:243.

Hatton, D., Sablowski, R. and Yung, M. H., (1995). *Two classes of cis-sequences contribute to tissue-specific expression of a PAL2 promoter in transgenic tobacco*. The Plant J., 7(6): 859–876.

Helseth E, et al. (1990). *J. Virol.* 64:2416–2420.

Hennessey E S, Drummond D R and Sparrow J C (1993). *Biochem. J.* 291:657–671.

Henry W L, Gardin J M and Ware J H (1980). *Circulation* 62:1054–1061.

Herman I M (1993). *Curr. Opin. Cell. Biol.* 5:48–55.

Hiatt, A., (1990). *Antibodies Produced in Plants*. Nature 344:469–470.

Hiatt, A., R. Cafferkey and K. Bowdish, (1989). *Production of Antibodies in Transgenic Plants*. Nature 342:76–78.

Hodgson J (1991). *Bio/Technology* 9:19–21.

Holmes K C, Popp D, Gebhard W and Kabsch W (1990). *Nature* 347:44–49.

Huse W D, et al. (1989). *Science* 246:1275–1281.

Innis M A, et al. (1990). *PCR Protocols: A Guide to Methods and Applications* (Academic Press, San Diego, Calif.).

Intapruk, C., Higashimura, N., Yamamoto, K., Okada, N., Shinmyo, A and Takano, M., (1991). *Nucleotide sequences of two genomic DNAs encoding peroxidase of Arabidopsis thaliana.* Gene, 98:237–241

Jablonski E, et al. (1986). *Nucl. Acids Res.* 14:6115–6128.

Jacobsen, K., Lausen, N. B., Jensen, E. O., Marcker, A., Poulsen, C and Macker, K. A., (1990). *HMG-1 like proteins from leaf and nodule nuclei interact with different AT motifs in soybean nodulin promoter.* Plant Cell, 2:85–94

Jakoby W B and Pastan I H (eds.) (1979). A Cell Culture. Methods in Enzymology, volume 58 (Academic Press, Inc., Harcourt Brace Jovanovich (New York)).

Jensen, E. O., Marcker, K. A., Schell, J and Bruijin, F. J., (1988). *Interaction of a nodule specific trans-acting factor with distinct DNA elements in the soybean leghaemoglobin Ibc3 5' upstream region.* EMBO, 7:1265–1271

Jofuku, K. D., Okamura, J. K and Goldberg, R. B., (1987). *Interaction of an embryo DNA binding protein with a soybean lectin upstream region.* Nature, 328:734–737

Johnson P A, et al. (1992). *J. Virol.* 66:2952–2965.

Johnson, et al. (1993). *Peptide Turn Mimetics,* Biotechnology and Pharmacy, Pezzuto et al., eds., Chapman and Hall, New York.

Jordano, J., Almoguerra, C and Thomas, T. L., (1989) *A sunflower helianthinin gene upstream sequence ensemble contains an enhancer and sites of nuclear protein interaction.* Plant Cell, 1 :855–866

Kaneda Y, et al. (1989). *J. Biol. Chem.* 264:12126–12129.

Kanehisa M (1984). *Nucl. Acids Res.* 12:203–213.

Kasper E K, Agema W R, Hutchins G M, Deckers J W, Hare J M and Baughman K L (1994). *J. Am. Coll. Cardiol.* 23:586–590.

Katagiri, I., Lam, E and Chua, N. H., (1989) *Two tobacco DNA-binding proteins with homology to the nuclear factor CREB.* Nature, 340:727–729

Kawaoka, A., Kawamoto, T., Sekine, M., Yoshida, K., Takano, M. and Shinmyo, A., (1 994). *A cis-acting element and a trans-acting factor involved in the wound-induced expression of a horseradish peroxidase gene.* The Plant J., (6(1):87–97.

Kinszler K W, et al. (1991). *Science* 251:1366–1370.

Kohler G and Milstein C (1975). *Nature* 256:495–497.

Kraemer F B, et al. (1993). *J. Lipid Res.* 34:663–672.

Kubo T, et al. (1988). *FEBS Letts.* 241:119.

Kuhiman P A, Hemmings L and Critchley D R (1992). *FEBS Lett.* 304:201–206.

Kumar A, Crawford K, Close L, Madison M, Lorenz J, Doetschman T, Pawlowski S, Duffy J, Neumann J, Robbins J, Boivin G P, O=Toole B A and Lessard J L (1997). *Proc. Natl. Acad. Sci. USA* 94:4406–4411.

Kyte J and Doolittle R F (1982). *J. Mol. Bio.* 157:105–132.

Lagrimini, L. M., (1996). *The role of the tobacco anionic peroxidase in growth and development.* In Plant Peroxidases: Biochemistry and Physiology, C. Obinger, U. Bumer, R. Ebermann, C. Penel, H. Greppin, eds, University of Geneva, pp 235–242.

Lagrimini, L. M., Bradford, S. and Rothstein, S., (1991). *Peroxidase-induced wilting in transgenic tobacco.* The Plant Cell, 2:7–18.

Lam, D M-K, J-J Shi, 1996. *Edible Vaccines.* Agro Good Ind Hi-Tech 7:7–12.

Landegren U, et al. (1988). *Science* 242:229–237.

Langridge, P., Pintor-Toro, J. A and Feix, G., (1982) *Transciptional effects on the opaque-2 mutation of Zea Mays L. Planta,* 156:166–170

Lankford E B, Epstein N D, Fananapazir L and Sweeney H L (1995). *J. Clin. Invest.* 95:1409–1414.

Lee J E, et al. (1995). *Science* 268:836–844.

Leffel, S. M., Mabon, S. A. and Steward, C. N., (1997). *Application of Green Fluorescent protein in plants.* BioTechniques, 23(5):912–916.

Levine B A, Moir A J, Patchell V B and Perry S V (1992). *FEBS Lett.* 298:44–48.

Lim C S, et al. (1991). *Circulation* 83:2007–2011.

Lipshutz R J, et al. (1995). *Biotechniques* 19:442–447.

Liu, Q., Kasuga, M., Sakuma, Y., Abe, H., Miura, S., Yamaguchi-Shinozaki, K and Shinozaki, K., (1998). *Two transcriptional factors DREB1 and DREB2 with an EREBP/AP2 DNA binding domain separate two cellular signal transduction pathways in drought and low temperature response gene expression respectively in arobidopsis.* Plant Cell, 10:1391–1406

Liu, W., Qi, Y and Hulett, F. M., (1998). *Site internal to the coding regions of phoA and phoS bind PhoP and are required for full promoter activity.* Molecular Microbiology, 28(1):119–130

Lockhart D J, et al. (1996). *Nature Biotechnology* 14:1675–1680.

Lu M H, DiLullo C, Schultheiss T, Holtzer S, Murray J M, Choi J, Fischman D A and Holtzer H (1992). *J. Cell Biol.* 117:1007–1022.

Ma, J K-C and M. B. Hein, 1995. *Plant Antibodies for Immunotherapy.* Plant Physiol. 109:341–346.

Ma, J K-C, T. Lehner, P. Stabila, C I Fux and A. Hiatt, 1994. *Assembly of Monoclonal Antibodies with IgG1 and IgA Heavy Chain Domains in Transgenic Tobacco Plants.* Eur. J. Immunol. 24:131.

Madzak C, et al. (1992). *J. Gen. Virol.* 73:1533–1536.

Maier, U. G., Brown, J. W. S., Schmitz, S. M., Dietrich, G and Feix, G., (1988) *Mapping of tissue-dependent and independent protein binding sites to the 5' upstream region of a zein gene.* Mol. Gen. gEnet., 212:241–245

Maniatis T, et al. (1982). *Molecular Cloning: A Laboratory Manual* (Cold Spring Harbor Laboratory, Cold Spring Harbor, N.Y.).

Mann R and Baltimore D (1985). *J. Virol.* 54:401–407.

Manolio T A, Baughman K L, Rodeheffer R, Pearson T A, Bristow J D, Michels V V, Abelmann W H and Harlan W R (1992). *Am J. Cardiol.* 69:1458–1466.

Margolskee R F (1992). *Curr. Top. Microbiol. Immunol.* 158:67–95.

Martin R, et al. (1990). *BioTechniques* 9:762–768.

Matteucci M D and Caruthers M H (1981). *J. Am. Chem. Soc.* 103:3185.

Matthews J A and Kricka L J (1988). *Anal. Biochem.* 169:1–25.

Mendelian Inheritance in Man, #s 102540, 115200, 302045, 600884, 601154, 601493, 601494.

Merrifield B (1963). *J. Am. Chem. Soc.* 85:2149–2156.

Mestroni L, Krajinovic M, Severini G M, Pinamonti B, Di Lenarda A, Giacca M, Falaschi A and Camerini F (1994). *Br. Heart J.* 72:S35–S41.

Metzger D, et al. (1988). *Nature* 334:31–36.

Michels V V, Driscoll D J and Miller F A (1985). *Am. J. Cardiol.* 55:1232–1233.

Michels V V, Moll P P, Miller F A, Tajik A J, Chu J S, Driscoll D J, Burnett J C, Rodeheffer R J, Chesebro J H and Tazelaar H D (1992). *N. Engl. J. Med.* 326:77–82.

Miller A D (1992). *Curr. Top. Microbiol. Immunol.* 158:1–24.

Miller A D, et al. (1985). *Mol. Cell. Biol.* 5:431–437.

Miller A D, et al. (1988). *J. Virol.* 62:4337–4345.

Mizukami, Y. and Ma, H., (1997). *Determination of Arabidopsis florial meristem identity by AGAMOUS.* Plant Cell, 9:393–408.

Modrich P (1991). Ann. Rev. Genet. 25:229–253.

Mohan, R., Bajr, A. M and Kolattukudy, P. E., (1993). Induction of a tomato anionic peroxidase gene (tap10 by wounding in transgenic tobacco and activation of tap1/GUS and tap2/GUS chimeric gene fusions in transgenic tobacco by wounding and pathogen attack. Plant Molecular Biology., 21:341–354

Mohan, R., Vijayan, P and Kolattudy, P. E., (1993) Developmental and tissue-specific expression of a tomato anionic peroxidase (tap 1) gene by a minimal promoter, with wound and pathogen induction by an additional 5'-flanking region. Plant Molecular Biology, 22:475–490

Mombaerts P, et al. (1992). *Cell* 68:869.

Moss B (1992). *Curr. Top. Microbiol. Immunol.* 158:25–38.

Moss B (1996). *Proc. Natl. Acad. Sci. USA* 93:11341–11348.

Muller, M and Kundsen, S., The nitrogen response of a barley C-hordein promoter is controlled by positive and negative regulation of the GCN4 and endosperm box. Plant J., 1993, 4:343–355

Muzyczka N (1992). *Curr. Top. Microbiol. Immunol.* 158:97–129.

Nabel (1992). *Hum. Gene Ther.* 3:399–410.

Nabel E G, et al. (1990). *Science* 249:1285–1288.

Naldini L et al. (1996). *Science* 272:263–267.

Newton C R, Graham A, Heptinstall L E, Powell S J, Summers C, Kalsheker N, Smith J C, and Markham A F (1989). *Nucl. Acids Res.* 17:2503–2516.

Nguyen Q, et al. (1992). *BioTechniques* 13:116–123.

Novack D F, et al. (1986). *Proc. Natl. Acad. Sci. USA* 83:586–590.

Ohi S, et al. (1990). *Gene* 89:279–282.

Okita, T. W., Hwang, Y. S., Hnilo, J., Kim, W. T., Aryan, A. P., Larsen, R and Krishnan, H. B., (1989). *Structure and expression of the rice glutin multigene family.* J. Biol. Chem., 264:12573–12581

Oksman-Caldentey, K-M, O. Kivela and R. Hiltunen, 1991. *Spontaneous Shoot Organogenesis and Plant Regeneration from Hairy Root Cultures of Hyoscyamus Muticus.* Plant Sci. 78:129–136.

Olson T M and Keating M T (1996). *J. Clin. Invest.* 97:528–532.

Olson T M and Keating M T (1997). *Trends Cardiovasc. Med.* 7:60.

Orita M, Iwahana H, Kanazawa H, Hayashi K and Sekiya T (1989). *Proc. Natl. Acad. Sci. USA* 86:2766–2770.

Ortiz-Lopez R, Li H, Su J, Goytia V and Towbin J A (1997). *Circulation* 95:2434–2440.

Osakabe, K., Koyama, H., Kawai, S., Katayama, Y and Morohoshi, N., (1995) *Molecular cloning of two tandemly arranged peroxidase genes from Populus kitakamiensis and their differential regulation in the stem.* Plant Molecular Biology., 28:677–689

Page K A, et al. (1990). *J. Virol.* 64:5270–5276.

Pellicer A, et al. (1980). *Science* 209:1414–1422.

Petropoulos C J, et al. (1992). *J. Virol.* 66:3391–3397.

Philpott K L, et al. (1992). *Science* 256:1448.

Ponte, I., Guillen, P., Debon, R. M., Reina, M., Aragay, A., Espel, E., Fonzo, N. D and Palau, J. (1994). *Narrow A/T-rich zones present at the distal 5'-flanking sequences of the zein genes Zc1 and Zc2 bind a unique 30 kDa HMG-like protein.* Plant Molecular Biology, 26:1893–1906

Quantin B, et al. (1992). *Proc. Natl. Acad. Sci. USA* 89:2581–2584.

Raghothama, K. G., Liu, D., Nelson, D. E., Hasegawa, P. M and Bressan, R. A., (1993). *Analysis of an osmotically regulated pathogenesis-related osmotin gene promoter.* Plant Molecular Biology., 23:1117–1128

Reisler E (1993). *Curr. Opin. Cell Biol.* 5:41–47.

*Remington's Pharmaceutical Sciences,* 18th Ed. (1990, Mack Publishing Co., Easton, Pa.).

Rigby P W J, et al. (1977). *J. Mol. Biol.* 113:237–251.

Riggs, C. D., Voelker, T. A and Chrispeels, M. J., (1989). *Cotyledon nuclear proteins bind to DNA fragments harboring regulatory elements of phytohemagglutinin genes.* Plant Cell, 1:609–621

Roberts, E and Kolattukudy, P. E., *Molecular cloning, nucleotide sequence and abscisic acid induction of a suberization-associated highly anionic peroxidase.* Mol. Gen. Genet.

Rosenfeld M A, et al. (1992). *Cell* 68:143–155.

Ruano G and Kidd K K (1989). *Nucl. Acids Res.* 17:8392.

Russell D and Hirata R (1998). *Nature Genetics* 18:323–328.

Sambrook J, et al. (1989). *Molecular Cloning: A Laboratory Manual, 2nd Ed.* (Cold Spring Harbor Laboratory, Cold Spring Harbor, N.Y.).

Scharf S J, et al. (1986). *Science* 233:1076–1078.

Schneider G, et al. (1998). *Nature Genetics* 18:180–183.

Scopes R (1982). *Protein Purification: Principles and Practice,* (Springer-Verlag, N.Y.).

Sheffield V C, et al. (1989). *Proc. Natl. Acad. Sci. USA* 86:232–236.

Sheffield V C, et al., (1991). *Am. J. Hum. Genet.* 49:699–706.

Shenk T E, Rhodes C, Rigby P W and Berg P (1975). *Proc. Natl. Acad. Sci. USA* 72:989–993.

Shimada T, et al. (1991). *J. Clin. Invest.* 88:1043–1047.

Shinkai Y, et al. (1992). *Cell* 68:855.

Shoemaker D D, et al. (1996). *Nature Genetics* 14:450–456.

Sieburth, L. E. and Meyerowitz, E. M., (1997) *Molecular dissection of the AGAMOUS control region shows that cis elemens for spatial regulation are located intragenically.* Plant Cell, 9: 355–365.

Snouwaert J N, et al. (1992). *Science* 257:1083.

Sorge J, et al. (1984). *Mol. Cell. Biol.* 4:1730–1737.

Spargo C A, Fraiser M S, van Cleve M, Wright D J, Nycz C M, Spears P A and Walker G T (1996). *Mol. Cell. Probes* 10:247–256.

Spirito P, Seidman C E, McKenna W J and Maron B J (1997). *N. Engl. J. Med.* 336:775–785.

Stewart M J, et al. (1992). *Hum. Gene Ther.* 3:267–275.

Stratford-Perricaudet L D, et al. (1990). *Hum. Gene Ther.* 1:241–256.

Taylor, C. B., (1997). *Promoter fusion analysis: An insufficient measure of gene expression.* The Plant Cell, 9:273–275.

Valancius V and Smithies O (1991). *Mol. Cell Biol.* 11:1402.

Van Engelen, F. A., A. Schouten, J. W. Molthoff, J. Roosien, J. Salinas, W. G. Dirkse, A. Schots, J. Bakker, F. J. Gommers and M. A. Jongsma, 1994. *Coordinate Expression of Antibody Subunit Genes Yields High Levels of Functional Antibodies in Roots of Transgenic Tobacco.* Plant Mol. Biol. 26:1701–1710.

Vandekerckhove J, Bugaisky G and Buckingham M (1986). *J. Biol. Chem.* 261:1838–1843.

Vellanoweth, R. L. and Okita, T. W., (1993). *Analysis of nuclear proteins interacting with a wheat α/β gliadin seed storage protein gene.* Plant Mol. Biol., 22:25–41.

Vierling, R. A and Wilcox, J. R., (1996). *Microplate assay-for soybean seed coat peroxidase activity.* Seed Sci. & Technol., 24:485–494

Wagner E, et al. (1990). *Proc. Natl. Acad. Sci. USA* 87:3410–3414.

Wagner E, et al. (1991). *Proc. Natl. Acad. Sci. USA* 88:4255–4259.
Walker G T, Fraiser M S, Schram J L, Little M C, Nadeau J G and Malinowski D P (1992). *Nucl. Acids Res.* 20:1691–1696.
Wang C Y and Huang L (1989). *Biochemistry* 28:9508–9514.
Wartell R M, et al. (1990). *Nucl. Acids Res.* 18:2699–2705.
Watkins H, Seidman C E, Seidman J G, Feng H S and Sweeney H L (1996). *J. Clin. Invest.* 98:2456–2461.
Wells J A (1991). *Methods in Enzymol.* 202:390411.
Wetmur J G and Davidson N (1968). *J. Mol. Biol.* 31:349–370.
White M B, et al. (1992). *Genomics* 12:301–306.
White R and Lalouel J M (1988). *Ann. Rev. Genet.* 22:259–279.
Wilkinson G W and Akrigg A (1992). *Nucleic Acids Res.* 20:2233–2239.
Wolff J A, et al. (1990). *Science* 247:1465–1468.
Wolff J A, et al. (1991). *BioTechniques* 11:474–485.
Wu C H, et al. (1989b). *J. Biol. Chem.* 264:16985–16987.
Wu D Y and Wallace R B (1989a). *Genomics* 4:560–569.
Wu G Y, et al. (1991). *J. Biol. Chem.* 266:14338–14342.
Zenke M, et al. (1990). *Proc. Natl. Acad. Sci. USA* 87:3655–3659.
Zhao, Y and Okita, T. W., (1995). *Interactions between the Glutelin Gt3 5' flanking regulatory regions with rice nuclear proteins.* Plant Cell Physiol., 36(8):1657–1667
Patents and Patent Applications
EP 0332435
EP 225,807A
EP 425,731A
Hitzeman et al., EP 73,675A.
WO 84/03564
WO 90/07936
WO 92/19195
WO 93/07282
WO 94/25503
WO 95/01203
WO 95/05452
WO 96/02286
WO 96/02646
WO 96/11698
WO 96/40871
WO 96/40959
WO 97/02048
WO 97/12635
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,554,101
U.S. Pat. No. 4,683,195
U.S. Pat. No. 4,683,202
U.S. Pat. No. 4,816,567
U.S. Pat. No. 4,868,105
U.S. Pat. No. 5,252,479
U.S. Pat. No. 5,270,184
U.S. Pat. No. 5,376,543
U.S. Pat. No. 5,409,818
U.S. Pat. No. 5,436,146
U.S. Pat. No. 5,455,166
U.S. Pat. No. 5,550,050
U.S. Pat. No. 5,691,198
U.S. Pat. No. 5,747,469
U.S. Pat. No. 5,753,500

What is claimed is:

1. A recombinant DNA molecule comprising:
   a) a GmEPC regulatory sequence consisting of a nucleotide sequence consisting of nucleotides:
      1326 to 1532 in SEQ ID NO:20 in combination with a heterologous plant expressible promoter; and
   b) a heterologous structural gene, wherein said heterologous structural gene is under the regulatory control of said regulatory sequence and said plant expressible promoter.

2. The recombinant DNA molecule of claim 1, further comprising a hydrophobic leader sequence.

3. A vector comprising said recombinant DNA molecule of claim 1.

4. A recombinant promoter molecule, said promoter molecule comprising:
   a) a GmEPC regulatory sequence consisting of nucleotide sequence:
      1326 to 1532 in SEQ ID NO:20;
   b) a heterologous plant expressible promoter, providing a TATA box region and a transcription start site positioned 3' to said regulatory sequence, whereby a heterologous plant expressible structural gene, placed 3' to said recombinant promoter molecule is expressed under the regulatory control of said recombinant promoter molecule.

5. The recombinant promoter molecule of claim 4, further comprising a hydrophobic leader sequence.

6. A vector comprising said recombinant promoter molecule of claim 4.

7. A recombinant promoter molecule, said promoter molecule comprising a truncated, plant expressible promoter, providing a TATA box region and a transcription start site, whereby a heterologous plant expressible structural gene, placed 3' to said recombinant promoter molecule is expressed under the regulatory control of said recombinant promoter molecule, and wherein said truncated plant expressible promoter is selected from the group consisting of:
   a) a nucleotide sequence consisting of 9 to 1532 in SEQ ID NO:20;
   b) a nucleotide sequence consisting of 459 to 1532 in SEQ ID NO:20;
   c) a nucleotide sequence consisting of 1066 to 1532 in SEQ ID NO:20; and
   d) a nucleotide sequence consisting of 1326 to 1532 in SEQ ID NO:20.

8. The recombinant promoter molecule of claim 7, further comprising a hydrophobic leader sequence.

9. A vector comprising said recombinant promoter molecule of claim 7.

10. A recombinant DNA molecule comprising:
    a) a GmEPC regulatory sequence consisting of the nucleotide sequence from nucleotides 1326 to 1532 of SEQ ID NO: 20; and
    b) a heterologous structural gene, wherein said heterologous structural gene is under the regulatory control of said regulatory sequence.

11. The recombinant DNA molecule of claim 10, further comprising a hydrophobic leader sequence.

12. A vector comprising said recombinant DNA molecule of claim 10.

13. A recombinant DNA molecule comprising:
    a) a GmEPC regulatory sequence selected from the group consisting of:

i) a nucleotide sequence consisting of nucleotides 1066 to 1532 in SEQ ID NO:20; and
   ii) a nucleotide sequence consisting of nucleotides 1326 to 1532 in SEQ ID NO:20 in combination with a heterologous plant expressible promoter; and
   b) a heterologous structural gene,
wherein said heterologous structural gene is under the regulatory control of said regulatory sequence and said plant expressible promoter.

14. The recombinant DNA molecule of claim 13, further comprising a hydrophobic leader sequence.

15. A vector comprising said recombinant DNA molecule of claim 13.

16. A recombinant promoter molecule, said promoter molecule comprising:
   a) a GmEPC regulatory sequence selected from the group consisting of:
      i) a nucleotide sequence consisting of nucleotides 1066 to 1532 in SEQ ID NO:20; and
      ii) a nucleotide sequence consisting of nucleotides 1326 to 1532 in SEQ ID NO:20;
   b) a heterologous plant expressible promoter, providing a TATA box region and a transcription start site positioned 3' to said regulatory sequence,
whereby a heterologous plant expressible structural gene, placed 3' to said recombinant promoter molecule is expressed under the regulatory control of said recombinant promoter molecule.

17. The recombinant promoter molecule of claim 16, further comprising a hydrophobic leader sequence.

18. A recombinant DNA molecule consisting of:
   a) a GmEPC regulatory sequence selected from the group consisting of:
      i) a nucleotide sequence consisting of nucleotides 1066 to 1532 in SEQ ID NO:20; and
      ii) a nucleotide sequence consisting of nucleotides 1326 to 1532 in SEQ ID NO:20; and
   b) a heterologous structural gene,
wherein said heterologous structural gene is under the regulatory control of said regulatory sequence.

19. A vector comprising said recombinant DNA molecule of claim 18.

20. The recombinant DNA molecule of claim 18, wherein said regulatory sequence affects tissue specificity or level of expression of said structural gene.

21. A recombinant promoter molecule, said promoter molecule consisting of:
   a) a GmEPC regulatory sequence consisting of the nucleotide sequence from nucleotides 1326 to 1532 of SEQ ID NO: 20; and
   b) a transcription start site positioned 3' to said regulatory sequence,
whereby a heterologous plant expressible structural gene, placed 3' to said recombinant promoter molecule is expressed under the regulatory control of said recombinant promoter molecule.

22. A vector comprising the recombinant promoter molecule of claim 21.

23. The recombinant promoter molecule of claim 21, wherein said regulatory sequence affects tissue specificity or level of expression of the structural gene.

24. A recombinant promoter molecule, said promoter molecule consisting of:
   a) a GmEPC regulatory sequence selected from the group consisting:
      i) a nucleotide sequence consisting of nucleotides 1066 to 1532 in SEQ ID NO:20; and
      ii) a nucleotide sequence consisting of nucleotides 1326 to 1532 in SEQ ID NO:20; and
   b) a transcription start site positioned 3' to said regulatory sequence,
whereby a heterologous plant expressible structural gene, placed 3' to said recombinant promoter molecule is expressed under the regulatory control of said recombinant promoter molecule.

25. A vector comprising the recombinant promoter molecule of claim 24.

26. The recombinant promoter molecule of claim 24, wherein said regulatory sequence affects tissue specificity or level of expression of the structural gene.

27. A vector comprising said recombinant promoter molecule of claim 16.

* * * * *

SEQUENCE LISTING

<160> NUMBER OF SEQ ID NOS: 24

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:plant peroxidase conserved sequence

<400> SEQUENCE: 1

His Phe His Asp Cys Phe Val
 1               5

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:generic primer for plant peroxidase

<400> SEQUENCE: 2
cayttycayg aytgyttygt                                               20

<210> SEQ ID NO 3

```
<211> LENGTH: 19
<212> TYPE: DNA
<213> ORGANISM: Glycine max

<400> SEQUENCE: 3
aaattaactc agctgtggg                                                  19

<210> SEQ ID NO 4
<211> LENGTH: 20
<212> TYPE: DNA
<213> ORGANISM: Glycine max

<400> SEQUENCE: 4
ggaacccact tattccatcg                                                 20

<210> SEQ ID NO 5
<211> LENGTH: 19
<212> TYPE: DNA
<213> ORGANISM: Glycine max

<400> SEQUENCE: 5
cccaagacat gcttgagat                                                  19

<210> SEQ ID NO 6
<211> LENGTH: 17
<212> TYPE: DNA
<213> ORGANISM: Glycine max

<400> SEQUENCE: 6
aagttcatac ttctaac                                                    17

<210> SEQ ID NO 7
<211> LENGTH: 7
<212> TYPE: PRT
<213> ORGANISM: Glycine max
<220> FEATURE:
<221> NAME/KEY: PEPTIDE
<222> LOCATION: (3)..(5)
<223> OTHER INFORMATION: Xaa may be any amino acid.

<400> SEQUENCE: 7

Gln Leu Xaa Xaa Xaa Phe Tyr
 1               5

<210> SEQ ID NO 8
<211> LENGTH: 6
<212> TYPE: PRT
<213> ORGANISM: Glycine max

<400> SEQUENCE: 8

Ala Ala Thr Ala Ala Ala
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:conserved
      subdomain in plant peroxidases

<400> SEQUENCE: 9

His Phe His Asp Cys Phe Val
 1               5
```

-continued

```
<210> SEQ ID NO 10
<211> LENGTH: 1314
<212> TYPE: DNA
<213> ORGANISM: Glycine max
<220> FEATURE:
<221> NAME/KEY: 5'UTR
<222> LOCATION: (1)..(82)
<220> FEATURE:
<221> NAME/KEY: CDS
<222> LOCATION: (83)..(1054)
<220> FEATURE:
<221> NAME/KEY: 3'UTR
<222> LOCATION: (1055)..(1314)
<220> FEATURE:
<221> NAME/KEY: sig_peptide
<222> LOCATION: (83)..(145)
<220> FEATURE:
<221> NAME/KEY: mat_peptide
<222> LOCATION: (146)..(1054)

<400> SEQUENCE: 10
gaagcatctg agtgtttact attttgtact atatttatat atagtcactc aagcttctag      60
gatttctgcc tgctgcatca aa atg gga agc aac ttg agg ttt ttg agt ctt     112
                         Met Gly Ser Asn Leu Arg Phe Leu Ser Leu
                          -20                 -15 tgc ctc ttg gca ttg att gca tcg act cat gct caa ctt cag ctt ggt      160
Cys Leu Leu Ala Leu Ile Ala Ser Thr His Ala Gln Leu Gln Leu Gly
    -10                  -5                  -1   1               5 ttt tat gct aac agt tgc cca aaa gca gag caa att gtt ttg aaa ttt      208
Phe Tyr Ala Asn Ser Cys Pro Lys Ala Glu Gln Ile Val Leu Lys Phe
                10                  15                  20 gtt cat gac cat atc cac aat gct cca tca cta gca gct gca tta ata      256
Val His Asp His Ile His Asn Ala Pro Ser Leu Ala Ala Ala Leu Ile
            25                  30                  35 aga atg cac ttt cat gac tgt ttt gta agg gga tgt gat gca tca gtc      304
Arg Met His Phe His Asp Cys Phe Val Arg Gly Cys Asp Ala Ser Val
        40                  45                  50 ctt ctg aac tca aca acc aat cag gct gag aag aat gct cct cca aat      352
Leu Leu Asn Ser Thr Thr Asn Gln Ala Glu Lys Asn Ala Pro Pro Asn
    55                  60                  65 ctc aca gta aga ggc ttt gac ttc att gac aga ata aag agc ctt gtt      400
Leu Thr Val Arg Gly Phe Asp Phe Ile Asp Arg Ile Lys Ser Leu Val
70                  75                  80                  85 gaa gct gaa tgc cct ggt gtg gtc tct tgt gct gat atc ctc act ttg      448
Glu Ala Glu Cys Pro Gly Val Val Ser Cys Ala Asp Ile Leu Thr Leu
                90                  95                 100 gct gcc aga gac act att gta gcc aca ggt gga cct ttt tgg aaa gtt      496
Ala Ala Arg Asp Thr Ile Val Ala Thr Gly Gly Pro Phe Trp Lys Val
            105                 110                 115 cca act ggt cga agg gat ggg gtc gtc tct aac ttg acg gaa gcc aga      544
Pro Thr Gly Arg Arg Asp Gly Val Val Ser Asn Leu Thr Glu Ala Arg
        120                 125                 130 aat aac att cct gct cca tct tcc aac ttt acc acc cta caa aca ctc      592
Asn Asn Ile Pro Ala Pro Ser Ser Asn Phe Thr Thr Leu Gln Thr Leu
    135                 140                 145 ttt gct aac caa gga ctt gat ttg aag gac ttg gtc ctg ctc tct ggt      640
Phe Ala Asn Gln Gly Leu Asp Leu Lys Asp Leu Val Leu Leu Ser Gly
150                 155                 160                 165 gct cac aca att ggt atc gct cat tgc tca tca tta tca aac cgg ttg      688
Ala His Thr Ile Gly Ile Ala His Cys Ser Ser Leu Ser Asn Arg Leu
                170                 175                 180 ttc aat ttc act ggc aag ggt gat caa gac ccg tca cta gat agt gaa      736
Phe Asn Phe Thr Gly Lys Gly Asp Gln Asp Pro Ser Leu Asp Ser Glu
            185                 190                 195
```

```
tat gct gca aat ttg aaa gca ttc aag tgc aca gac ctc aac aag ttg      784
Tyr Ala Ala Asn Leu Lys Ala Phe Lys Cys Thr Asp Leu Asn Lys Leu
        200                 205                 210 aac acc aca aaa att gag atg gac cct gga agt cgc aag aca ttt gat      832
Asn Thr Thr Lys Ile Glu Met Asp Pro Gly Ser Arg Lys Thr Phe Asp
    215                 220                 225 ctt agc tac tat agt cac gtt att aag aga agg ggt cta ttt gag tca      880
Leu Ser Tyr Tyr Ser His Val Ile Lys Arg Arg Gly Leu Phe Glu Ser
230                 235                 240                 245 gat gct gca tta ttg act aac tca gtt aca aag gca caa atc atc caa      928
Asp Ala Ala Leu Leu Thr Asn Ser Val Thr Lys Ala Gln Ile Ile Gln
            250                 255                 260 ttg ctt gaa ggg tca gtt gaa aat ttc ttt gct gag ttt gca acc tcc      976
Leu Leu Glu Gly Ser Val Glu Asn Phe Phe Ala Glu Phe Ala Thr Ser
                265                 270                 275 atc gag aaa atg gga aga att aat gtg aag aca ggc aca gaa gga gag     1024
Ile Glu Lys Met Gly Arg Ile Asn Val Lys Thr Gly Thr Glu Gly Glu
        280                 285                 290 atc agg aag cat tgt gca ttt ata aat agc taagaatctt gtcttggggt       1074
Ile Arg Lys His Cys Ala Phe Ile Asn Ser
    295                 300 ttgattattt atgctatgcc atgttttttg attagttatg ctatgccatg tggtctctgt   1134
ctacatacgt gtgatccttt atggtatggt tgttgtatgt gtgttggaat aagtgggctc   1194
ttaagttatt catatttcca actttccaac tttgctggta gatcatgctc ttgtaataag   1254
aaccagaatt ttttgtgcta cccacagctg agttaattta aaaaaaaaaa aaaaaaaaa    1314

<210> SEQ ID NO 11
<211> LENGTH: 324
<212> TYPE: PRT
<213> ORGANISM: Glycine max

<400> SEQUENCE: 11

Met Gly Ser Asn Leu Arg Phe Leu Ser Leu Cys Leu Leu Ala Leu Ile
    -20                 -15                 -10

Ala Ser Thr His Ala Gln Leu Gln Leu Gly Phe Tyr Ala Asn Ser Cys
-5              -1   1               5                   10

Pro Lys Ala Glu Gln Ile Val Leu Lys Phe Val His Asp His Ile His
            15                  20                  25

Asn Ala Pro Ser Leu Ala Ala Ala Leu Ile Arg Met His Phe His Asp
        30                  35                  40

Cys Phe Val Arg Gly Cys Asp Ala Ser Val Leu Leu Asn Ser Thr Thr
    45                  50                  55

Asn Gln Ala Glu Lys Asn Ala Pro Pro Asn Leu Thr Val Arg Gly Phe
60                  65                  70                  75

Asp Phe Ile Asp Arg Ile Lys Ser Leu Val Glu Ala Glu Cys Pro Gly
                80                  85                  90

Val Val Ser Cys Ala Asp Ile Leu Thr Leu Ala Ala Arg Asp Thr Ile
            95                  100                 105

Val Ala Thr Gly Gly Pro Phe Trp Lys Val Pro Thr Gly Arg Arg Asp
        110                 115                 120

Gly Val Val Ser Asn Leu Thr Glu Ala Arg Asn Asn Ile Pro Ala Pro
    125                 130                 135

Ser Ser Asn Phe Thr Thr Leu Gln Thr Leu Phe Ala Asn Gln Gly Leu
140                 145                 150                 155

Asp Leu Lys Asp Leu Val Leu Leu Ser Gly Ala His Thr Ile Gly Ile
```

```
                     160                 165                 170
Ala His Cys Ser Ser Leu Ser Asn Arg Leu Phe Asn Phe Thr Gly Lys
            175                 180                 185

Gly Asp Gln Asp Pro Ser Leu Asp Ser Glu Tyr Ala Ala Asn Leu Lys
        190                 195                 200

Ala Phe Lys Cys Thr Asp Leu Asn Lys Leu Asn Thr Thr Lys Ile Glu
    205                 210                 215

Met Asp Pro Gly Ser Arg Lys Thr Phe Asp Leu Ser Tyr Tyr Ser His
220                 225                 230                 235

Val Ile Lys Arg Arg Gly Leu Phe Glu Ser Asp Ala Ala Leu Leu Thr
                240                 245                 250

Asn Ser Val Thr Lys Ala Gln Ile Ile Gln Leu Leu Glu Gly Ser Val
            255                 260                 265

Glu Asn Phe Phe Ala Glu Phe Ala Thr Ser Ile Glu Lys Met Gly Arg
        270                 275                 280

Ile Asn Val Lys Thr Gly Thr Glu Gly Glu Ile Arg Lys His Cys Ala
    285                 290                 295

Phe Ile Asn Ser
300

<210> SEQ ID NO 12
<211> LENGTH: 1326
<212> TYPE: DNA
<213> ORGANISM: Glycine max
<220> FEATURE:
<221> NAME/KEY: 5'UTR
<222> LOCATION: (1)..(86)
<220> FEATURE:
<221> NAME/KEY: CDS
<222> LOCATION: (87)..(1058)
<220> FEATURE:
<221> NAME/KEY: 3'UTR
<222> LOCATION: (1059)..(1326)
<220> FEATURE:
<221> NAME/KEY: sig_peptide
<222> LOCATION: (87)..(149)
<220> FEATURE:
<221> NAME/KEY: mat_peptide
<222> LOCATION: (150)..(1058)

<400> SEQUENCE: 12
gcctctttca agaagcatct gagtgcttat tatttgtaat atatatagtc actcaagctt      60
ctaggatttg tgccagctac atgaaa atg gga agc aac ttc agg ttt ttg agt     113
                            Met Gly Ser Asn Phe Arg Phe Leu Ser
                                -20                 -15 ctt tgc ctc ttg gca ttg att gca tca acc cat gct caa ctt cag ctt     161
Leu Cys Leu Leu Ala Leu Ile Ala Ser Thr His Ala Gln Leu Gln Leu
        -10                 -5                  -1   1 ggt ttt tat gcc aag agt tgc cca aac gct gag caa atc gtt ttg aaa     209
Gly Phe Tyr Ala Lys Ser Cys Pro Asn Ala Glu Gln Ile Val Leu Lys
 5                  10                  15                  20 ttt gtc cat gac cat atc cac aat gct cca tca cta gca gct gca ttg     257
Phe Val His Asp His Ile His Asn Ala Pro Ser Leu Ala Ala Ala Leu
                25                  30                  35 ata aga atg cac ttc cat gac tgt ttt gta agg gga tgt gat gca tca     305
Ile Arg Met His Phe His Asp Cys Phe Val Arg Gly Cys Asp Ala Ser
            40                  45                  50 gtc ctt ctg aac tca aca acc aat caa gct gaa aag aat gct cct cca     353
Val Leu Leu Asn Ser Thr Thr Asn Gln Ala Glu Lys Asn Ala Pro Pro
        55                  60                  65 aat ctc aca gta aga ggc ttt gac ttc att gac aga ata aag agc ctt     401
```

|  |  |  |  |  |  |  |  |  |  |  |  |  |  |  |  |
|---|---|---|---|---|---|---|---|---|---|---|---|---|---|---|---|
| Asn | Leu | Thr | Val | Arg | Gly | Phe | Asp | Phe | Ile | Asp | Arg | Ile | Lys | Ser | Leu |
|  | 70 |  |  |  | 75 |  |  |  | 80 |  |  |  |  |  |  |

```
gtt gag gca gaa tgc cct ggt gtg gtc tct tgt gct gat atc ctc act    449
Val Glu Ala Glu Cys Pro Gly Val Val Ser Cys Ala Asp Ile Leu Thr
 85              90              95             100 ttg tct gcc aga gac act att gta gcc aca ggt gga cca ttt tgg aaa    497
Leu Ser Ala Arg Asp Thr Ile Val Ala Thr Gly Gly Pro Phe Trp Lys
            105             110             115 gtt cca aca ggt cga aga gat ggg gtc atc tct aac ttg acg gaa gcc    545
Val Pro Thr Gly Arg Arg Asp Gly Val Ile Ser Asn Leu Thr Glu Ala
            120             125             130 aga gat aac att cct gct cca tct tct aac ttt acc acc cta caa aca    593
Arg Asp Asn Ile Pro Ala Pro Ser Ser Asn Phe Thr Thr Leu Gln Thr
        135             140             145 ctc ttt gcc aac caa gga ctt gat ttg aag gac ttg gtc ctg ctc tct    641
Leu Phe Ala Asn Gln Gly Leu Asp Leu Lys Asp Leu Val Leu Leu Ser
    150             155             160 ggt gct cac aca att ggt atc gct cat tgc tca tca ttg tca aac cgc    689
Gly Ala His Thr Ile Gly Ile Ala His Cys Ser Ser Leu Ser Asn Arg
165             170             175             180 ttg ttc aat ttc act ggc aag ggt gat caa gac ccg tca tta gac agt    737
Leu Phe Asn Phe Thr Gly Lys Gly Asp Gln Asp Pro Ser Leu Asp Ser
            185             190             195 gaa tat gct gca aat ctg aaa gcc ttc aag tgc acg gac ctc aat aag    785
Glu Tyr Ala Ala Asn Leu Lys Ala Phe Lys Cys Thr Asp Leu Asn Lys
        200             205             210 ttg aac acc aca aaa att gag atg gac cct gga agt cgc aag aca ttt    833
Leu Asn Thr Thr Lys Ile Glu Met Asp Pro Gly Ser Arg Lys Thr Phe
    215             220             225 gat ctt agc tac tat agt cat gtg att aag aga agg ggt cta ttt gag    881
Asp Leu Ser Tyr Tyr Ser His Val Ile Lys Arg Arg Gly Leu Phe Glu
230             235             240 tca gat gct gca ttg ttg aca aac tca gtt aca aag gct caa atc att    929
Ser Asp Ala Ala Leu Leu Thr Asn Ser Val Thr Lys Ala Gln Ile Ile
245             250             255             260 gaa ttg ctt gaa ggg tca gtt gaa aat ttc ttt gct gag ttt gca acc    977
Glu Leu Leu Glu Gly Ser Val Glu Asn Phe Phe Ala Glu Phe Ala Thr
            265             270             275 tcc atg gag aaa atg gga aga att aat gta aag aca ggg aca gaa gga   1025
Ser Met Glu Lys Met Gly Arg Ile Asn Val Lys Thr Gly Thr Glu Gly
        280             285             290 gag atc agg aag cat tgt gca ttt cta aat agc taagaatctt gtcttgttca  1078
Glu Ile Arg Lys His Cys Ala Phe Leu Asn Ser
    295             300 tggatgaatc ttgtatcatt tattttttgg gtttggttat ttatgctatg ccatgttttt  1138
ttattagtta tgctatgcca tgtggtgtct gtctacatat gagtgatccc gtatggtatg  1198
gttgttgtat gtgcgatgga ataagtgggt tccattgtta ttcttataat ttccaactt   1258 gctggtagat cttgtaataa gaagcagaat ttcttgtgct aaaaaaaaaa aaaaaaaaa   1318 aaaaaaaa                                                            1326

<210> SEQ ID NO 13
<211> LENGTH: 324
<212> TYPE: PRT
<213> ORGANISM: Glycine max

<400> SEQUENCE: 13

Met Gly Ser Asn Phe Arg Phe Leu Ser Leu Cys Leu Leu Ala Leu Ile
    -20             -15             -10
```

```
Ala Ser Thr His Ala Gln Leu Gln Leu Gly Phe Tyr Ala Lys Ser Cys
 -5              -1   1               5                      10

Pro Asn Ala Glu Gln Ile Val Leu Lys Phe Val His Asp His Ile His
             15                  20              25

Asn Ala Pro Ser Leu Ala Ala Leu Ile Arg Met His Phe His Asp
         30              35                  40

Cys Phe Val Arg Gly Cys Asp Ala Ser Val Leu Leu Asn Ser Thr Thr
         45              50              55

Asn Gln Ala Glu Lys Asn Ala Pro Pro Asn Leu Thr Val Arg Gly Phe
 60              65              70                      75

Asp Phe Ile Asp Arg Ile Lys Ser Leu Val Glu Ala Glu Cys Pro Gly
             80                  85                  90

Val Val Ser Cys Ala Asp Ile Leu Thr Leu Ser Ala Arg Asp Thr Ile
             95              100             105

Val Ala Thr Gly Gly Pro Phe Trp Lys Val Pro Thr Gly Arg Arg Asp
            110             115             120

Gly Val Ile Ser Asn Leu Thr Glu Ala Arg Asp Asn Ile Pro Ala Pro
        125             130             135

Ser Ser Asn Phe Thr Thr Leu Gln Thr Leu Phe Ala Asn Gln Gly Leu
140             145             150                     155

Asp Leu Lys Asp Leu Val Leu Leu Ser Gly Ala His Thr Ile Gly Ile
            160             165             170

Ala His Cys Ser Ser Leu Ser Asn Arg Leu Phe Asn Phe Thr Gly Lys
            175             180             185

Gly Asp Gln Asp Pro Ser Leu Asp Ser Glu Tyr Ala Ala Asn Leu Lys
        190             195             200

Ala Phe Lys Cys Thr Asp Leu Asn Lys Leu Asn Thr Thr Lys Ile Glu
        205             210             215

Met Asp Pro Gly Ser Arg Lys Thr Phe Asp Leu Ser Tyr Tyr Ser His
220             225             230                     235

Val Ile Lys Arg Arg Gly Leu Phe Glu Ser Asp Ala Ala Leu Leu Thr
            240             245             250

Asn Ser Val Thr Lys Ala Gln Ile Ile Glu Leu Leu Glu Gly Ser Val
            255             260             265

Glu Asn Phe Phe Ala Glu Phe Ala Thr Ser Met Glu Lys Met Gly Arg
        270             275             280

Ile Asn Val Lys Thr Gly Thr Glu Gly Glu Ile Arg Lys His Cys Ala
        285             290             295

Phe Leu Asn Ser
300

<210> SEQ ID NO 14
<211> LENGTH: 1191
<212> TYPE: DNA
<213> ORGANISM: Glycine max
<220> FEATURE:
<221> NAME/KEY: 5'UTR
<222> LOCATION: (1)..(59)
<220> FEATURE:
<221> NAME/KEY: CDS
<222> LOCATION: (60)..(998)
<220> FEATURE:
<221> NAME/KEY: 3'UTR
<222> LOCATION: (999)..(1191)
<220> FEATURE:
<221> NAME/KEY: sig_peptide
<222> LOCATION: (60)..(122)
<220> FEATURE:
```

<221> NAME/KEY: mat_peptide
<222> LOCATION: (123)..(998)

<400> SEQUENCE: 14

```
ggcacgagga gagagagaga gagagaacta gtctcgagca tcaaagtact caaattagc        59 atg gct gtc atg gtt gca ttc ttg aat ttg atc atc ttt tca gta gtc       107
Met Ala Val Met Val Ala Phe Leu Asn Leu Ile Ile Phe Ser Val Val
    -20             -15                 -10 tct aca aca ggc aag tca ctg agc tta aac tac tat gca aaa aca tgc       155
Ser Thr Thr Gly Lys Ser Leu Ser Leu Asn Tyr Tyr Ala Lys Thr Cys
 -5              -1   1               5                  10 cct aat gtg gag ttc att gtt gcc aag gca gta aag gat gcc act gct       203
Pro Asn Val Glu Phe Ile Val Ala Lys Ala Val Lys Asp Ala Thr Ala
             15                  20                  25 agg gac aaa act gtt cca gca gca att ctg cga atg cac ttc cat gat       251
Arg Asp Lys Thr Val Pro Ala Ala Ile Leu Arg Met His Phe His Asp
         30                  35                  40 tgt ttc gtt cgg ggg tgt gat gcc tct gtg ctg cta aat tca aaa gga       299
Cys Phe Val Arg Gly Cys Asp Ala Ser Val Leu Leu Asn Ser Lys Gly
     45                  50                  55 aac aac aaa gca gaa aaa gac ggg cca cca aat gtt tct ttg cat gca       347
Asn Asn Lys Ala Glu Lys Asp Gly Pro Pro Asn Val Ser Leu His Ala
 60              65                  70                  75 ttc tat gtc att gta gca gca aag aaa gca cta gaa gct tca tgc cct       395
Phe Tyr Val Ile Val Ala Ala Lys Lys Ala Leu Glu Ala Ser Cys Pro
             80                  85                  90 ggt gtg gtc tct tgt gct gac atc ctt gct ctg gca gca agg gtc gca       443
Gly Val Val Ser Cys Ala Asp Ile Leu Ala Leu Ala Ala Arg Val Ala
         95                  100                 105 gtt ttt ctg tca gga gga cct aca tgg gat gtt cct aaa gga aga aag       491
Val Phe Leu Ser Gly Gly Pro Thr Trp Asp Val Pro Lys Gly Arg Lys
     110                 115                 120 gat ggt aga aca tct aaa gcc agt gaa acc aga caa ttg cca gca cca       539
Asp Gly Arg Thr Ser Lys Ala Ser Glu Thr Arg Gln Leu Pro Ala Pro
 125             130                 135 acc ttc aac tta tca caa ctg cgg caa agt ttc tct caa aga gga ctg       587
Thr Phe Asn Leu Ser Gln Leu Arg Gln Ser Phe Ser Gln Arg Gly Leu
140                 145                 150                 155 tca ggg gaa gac ctg gta gct ctg tca ggg ggg cac act ttg ggt ttc       635
Ser Gly Glu Asp Leu Val Ala Leu Ser Gly Gly His Thr Leu Gly Phe
             160                 165                 170 tct cac tgc tca tct ttc aag aac aga atc cac aac ttc aat gca aca       683
Ser His Cys Ser Ser Phe Lys Asn Arg Ile His Asn Phe Asn Ala Thr
         175                 180                 185 cat gat gtt gac cct tca tta aat cca tca ttt gca gca aaa ctg atc       731
His Asp Val Asp Pro Ser Leu Asn Pro Ser Phe Ala Ala Lys Leu Ile
     190                 195                 200 tca att tgt cca cta aaa aat cag gca aaa aat gca ggc acc tct atg       779
Ser Ile Cys Pro Leu Lys Asn Gln Ala Lys Asn Ala Gly Thr Ser Met
 205                 210                 215 gac cct tca aca aca act ttt gat aat aca tat tac agg ttg atc ctc       827
Asp Pro Ser Thr Thr Thr Phe Asp Asn Thr Tyr Tyr Arg Leu Ile Leu
220                 225                 230                 235 caa cag aaa ggc ttg ttt tct tct gat caa gtt ttg ctt gac aac cca       875
Gln Gln Lys Gly Leu Phe Ser Ser Asp Gln Val Leu Leu Asp Asn Pro
             240                 245                 250 gac act aaa aat ctg gtt aca aag ttt gcc acc tca aaa aag gct ttt       923
Asp Thr Lys Asn Leu Val Thr Lys Phe Ala Thr Ser Lys Lys Ala Phe
         255                 260                 265
```

```
tat gag gct ttt gcg aag tcc atg atc aga atg agt agc tac aat ggt      971
Tyr Glu Ala Phe Ala Lys Ser Met Ile Arg Met Ser Ser Tyr Asn Gly
        270                 275                 280 gga cag gag gtt aga agg act gca gaa tgatcaatta ataagtctta            1018
Gly Gln Glu Val Arg Arg Thr Ala Glu
        285                 290 aatcaattca agttaaattg atgttccaaa caagttggat caaatttcct agatgccaag    1078
atattatgtc tttttcctct attaaagaaa tatgtatatt tatctgaagt taataaaatc    1138
tcaagcatgt cttgggaaat taatttagag ctcaaaaaaa aaaaaaaaaa aaa           1191

<210> SEQ ID NO 15
<211> LENGTH: 313
<212> TYPE: PRT
<213> ORGANISM: Glycine max

<400> SEQUENCE: 15

Met Ala Val Met Val Ala Phe Leu Asn Leu Ile Ile Phe Ser Val Val
        -20                 -15                 -10

Ser Thr Thr Gly Lys Ser Leu Ser Leu Asn Tyr Tyr Ala Lys Thr Cys
 -5              -1   1              5                   10

Pro Asn Val Glu Phe Ile Val Ala Lys Ala Val Lys Asp Ala Thr Ala
                 15                  20                  25

Arg Asp Lys Thr Val Pro Ala Ala Ile Leu Arg Met His Phe His Asp
         30                  35                  40

Cys Phe Val Arg Gly Cys Asp Ala Ser Val Leu Leu Asn Ser Lys Gly
         45                  50                  55

Asn Asn Lys Ala Glu Lys Asp Gly Pro Pro Asn Val Ser Leu His Ala
 60              65                  70                  75

Phe Tyr Val Ile Val Ala Ala Lys Lys Ala Leu Glu Ala Ser Cys Pro
                 80                  85                  90

Gly Val Val Ser Cys Ala Asp Ile Leu Ala Leu Ala Ala Arg Val Ala
                 95                 100                 105

Val Phe Leu Ser Gly Gly Pro Thr Trp Asp Val Pro Lys Gly Arg Lys
        110                 115                 120

Asp Gly Arg Thr Ser Lys Ala Ser Glu Thr Arg Gln Leu Pro Ala Pro
        125                 130                 135

Thr Phe Asn Leu Ser Gln Leu Arg Gln Ser Phe Ser Gln Arg Gly Leu
140                 145                 150                 155

Ser Gly Glu Asp Leu Val Ala Leu Ser Gly His Thr Leu Gly Phe
                160                 165                 170

Ser His Cys Ser Ser Phe Lys Asn Arg Ile His Asn Phe Asn Ala Thr
        175                 180                 185

His Asp Val Asp Pro Ser Leu Asn Pro Ser Phe Ala Ala Lys Leu Ile
        190                 195                 200

Ser Ile Cys Pro Leu Lys Asn Gln Ala Lys Asn Ala Gly Thr Ser Met
205                 210                 215

Asp Pro Ser Thr Thr Phe Asp Asn Thr Tyr Tyr Arg Leu Ile Leu
220                 225                 230                 235

Gln Gln Lys Gly Leu Phe Ser Ser Asp Gln Val Leu Leu Asp Asn Pro
        240                 245                 250

Asp Thr Lys Asn Leu Val Thr Lys Phe Ala Thr Ser Lys Lys Ala Phe
        255                 260                 265

Tyr Glu Ala Phe Ala Lys Ser Met Ile Arg Met Ser Ser Tyr Asn Gly
        270                 275                 280
```

```
Gly Gln Glu Val Arg Arg Thr Ala Glu
    285                 290
```

```
<210> SEQ ID NO 16
<211> LENGTH: 1167
<212> TYPE: DNA
<213> ORGANISM: Glycine max
<220> FEATURE:
<221> NAME/KEY: 5'UTR
<222> LOCATION: (1)..(38)
<220> FEATURE:
<221> NAME/KEY: CDS
<222> LOCATION: (39)..(977)
<220> FEATURE:
<221> NAME/KEY: 3'UTR
<222> LOCATION: (987)..(1167)
<220> FEATURE:
<221> NAME/KEY: sig_peptide
<222> LOCATION: (39)..(101)
<220> FEATURE:
<221> NAME/KEY: mat_peptide
<222> LOCATION: (102)..(977)

<400> SEQUENCE: 16
```

| | | |
|---|---|---|
| ggcacgaggc taaaaatcat cgaagtactc aaattagc atg gct gtc atg gtt gca<br>                                        Met Ala Val Met Val Ala<br>                                            -20 | | 56 |
| ttc ttg aat ttg atc atc atg ttt tca gta gtc tct aca agc aag tca<br>Phe Leu Asn Leu Ile Ile Met Phe Ser Val Val Ser Thr Ser Lys Ser<br>-15             -10               -5                -1  1 | | 104 |
| ctg agc tta aac tac tat tca aaa aca tgc cct gat gtg gaa tgc att<br>Leu Ser Leu Asn Tyr Tyr Ser Lys Thr Cys Pro Asp Val Glu Cys Ile<br>             5                  10                 15 | | 152 |
| gtt gcc aag gca gtg aag gat gcc act gct agg gac aaa act gtt cca<br>Val Ala Lys Ala Val Lys Asp Ala Thr Ala Arg Asp Lys Thr Val Pro<br>     20                  25                 30 | | 200 |
| gct gca ctt ctg cga atg cac ttc cat gac tgt ttc gtt cgg ggg tgt<br>Ala Ala Leu Leu Arg Met His Phe His Asp Cys Phe Val Arg Gly Cys<br> 35                  40                 45 | | 248 |
| ggt gcc tct gtg ctg cta aat tca aaa gga agc aac aaa gca gaa aaa<br>Gly Ala Ser Val Leu Leu Asn Ser Lys Gly Ser Asn Lys Ala Glu Lys<br> 50                  55                 60                 65 | | 296 |
| gat ggg cca cca aat gtt tct ttg cat gca ttc tat gtc att gat gca<br>Asp Gly Pro Pro Asn Val Ser Leu His Ala Phe Tyr Val Ile Asp Ala<br>                 70                  75                 80 | | 344 |
| gcg aag aaa gca cta gaa gct tca tgc cca ggt gtg gtc tct tgt gct<br>Ala Lys Lys Ala Leu Glu Ala Ser Cys Pro Gly Val Val Ser Cys Ala<br>             85                  90                 95 | | 392 |
| gac atc ctt gct cta gca gca agg gat gca gtt ttt ctg tca gga gga<br>Asp Ile Leu Ala Leu Ala Ala Arg Asp Ala Val Phe Leu Ser Gly Gly<br>        100                 105                110 | | 440 |
| cct aca tgg gat gaa cct aaa gga aga aag gat ggc aga aca tct aaa<br>Pro Thr Trp Asp Glu Pro Lys Gly Arg Lys Asp Gly Arg Thr Ser Lys<br>    115                 120                 125 | | 488 |
| gcc agc gaa acc aga caa tta cca gca cca acc ttc aac tta tca caa<br>Ala Ser Glu Thr Arg Gln Leu Pro Ala Pro Thr Phe Asn Leu Ser Gln<br>130                 135                 140                145 | | 536 |
| ctg cgg caa agc ttt tct caa aga gga ctg tca ggg gaa gac ctg gta<br>Leu Arg Gln Ser Phe Ser Gln Arg Gly Leu Ser Gly Glu Asp Leu Val<br>                150                 155                160 | | 584 |
| gct ctg tca ggg ggg cac act ttg ggt ttc tct cac tgc tca tct ttc<br>Ala Leu Ser Gly Gly His Thr Leu Gly Phe Ser His Cys Ser Ser Phe<br>            165                 170                175 | | 632 |
| aag aac aga atc cac aac ttc aat gct aca cat gat gaa gac cct tca | | 680 |

-continued

```
                Lys Asn Arg Ile His Asn Phe Asn Ala Thr His Asp Glu Asp Pro Ser
                    180                 185                 190 tta aat cca tca ttt gca aca aaa ctg ata tca att tgt cca cta aaa        728
Leu Asn Pro Ser Phe Ala Thr Lys Leu Ile Ser Ile Cys Pro Leu Lys
    195                 200                 205 aat cag gca aaa aat gca ggc acc tct atg gac cct tca aca aca act        776
Asn Gln Ala Lys Asn Ala Gly Thr Ser Met Asp Pro Ser Thr Thr Thr
210                 215                 220                 225 ttt gat aat aca tat tac agg ttg atc ctc caa cag aaa ggc ttg ttt        824
Phe Asp Asn Thr Tyr Tyr Arg Leu Ile Leu Gln Gln Lys Gly Leu Phe
                230                 235                 240 tct tct gat caa gtt ttg ctt gac aac cca gac act aaa aat ctg gtt        872
Ser Ser Asp Gln Val Leu Leu Asp Asn Pro Asp Thr Lys Asn Leu Val
            245                 250                 255 gcg aag ttt gcc acc tca aaa aag gct ttt tat gac gct ttt gca aag        920
Ala Lys Phe Ala Thr Ser Lys Lys Ala Phe Tyr Asp Ala Phe Ala Lys
        260                 265                 270 tcc atg atc aaa atg agt agc atc aat ggt gga cag gag gtt aga agg        968
Ser Met Ile Lys Met Ser Ser Ile Asn Gly Gly Gln Glu Val Arg Arg
    275                 280                 285 act gca gag tgatcaatta aaaagtctta aattaattca agttaaattg               1017
Thr Ala Glu
290 atgtttcaaa caagttagaa gtatgaactt gttggatcaa atttcctaga tgcaagata      1077 ttatgtcttt ttcctctatt aaagaaatat gtatatttat ctgaagttaa taaatatatc    1137 attttgataa aaaaaaaaaa aaaaaaaaa                                       1167
```

<210> SEQ ID NO 17
<211> LENGTH: 313
<212> TYPE: PRT
<213> ORGANISM: Glycine max

<400> SEQUENCE: 17

```
Met Ala Val Met Val Ala Phe Leu Asn Leu Ile Ile Met Phe Ser Val
    -20                 -15                 -10

Val Ser Thr Ser Lys Ser Leu Ser Leu Asn Tyr Tyr Ser Lys Thr Cys
 -5              -1   1               5                  10

Pro Asp Val Glu Cys Ile Val Ala Lys Ala Val Lys Asp Ala Thr Ala
                15                  20                  25

Arg Asp Lys Thr Val Pro Ala Ala Leu Leu Arg Met His Phe His Asp
            30                  35                  40

Cys Phe Val Arg Gly Cys Gly Ala Ser Val Leu Leu Asn Ser Lys Gly
        45                  50                  55

Ser Asn Lys Ala Glu Lys Asp Gly Pro Pro Asn Val Ser Leu His Ala
60                  65                  70                  75

Phe Tyr Val Ile Asp Ala Ala Lys Lys Ala Leu Glu Ala Ser Cys Pro
                80                  85                  90

Gly Val Val Ser Cys Ala Asp Ile Leu Ala Leu Ala Ala Arg Asp Ala
                95                  100                 105

Val Phe Leu Ser Gly Gly Pro Thr Trp Asp Glu Pro Lys Gly Arg Lys
        110                 115                 120

Asp Gly Arg Thr Ser Lys Ala Ser Glu Thr Arg Gln Leu Pro Ala Pro
    125                 130                 135

Thr Phe Asn Leu Ser Gln Leu Arg Gln Ser Phe Ser Gln Arg Gly Leu
140                 145                 150                 155

Ser Gly Glu Asp Leu Val Ala Leu Ser Gly Gly His Thr Leu Gly Phe
```

-continued

```
        160                 165                 170
Ser His Cys Ser Ser Phe Lys Asn Arg Ile His Asn Phe Asn Ala Thr
            175                 180                 185

His Asp Glu Asp Pro Ser Leu Asn Pro Ser Phe Ala Thr Lys Leu Ile
    190                 195                 200

Ser Ile Cys Pro Leu Lys Asn Gln Ala Lys Asn Ala Gly Thr Ser Met
    205                 210                 215

Asp Pro Ser Thr Thr Thr Phe Asp Asn Thr Tyr Tyr Arg Leu Ile Leu
220                 225                 230                 235

Gln Gln Lys Gly Leu Phe Ser Ser Asp Gln Val Leu Leu Asp Asn Pro
            240                 245                 250

Asp Thr Lys Asn Leu Val Ala Lys Phe Ala Thr Ser Lys Lys Ala Phe
            255                 260                 265

Tyr Asp Ala Phe Ala Lys Ser Met Ile Lys Met Ser Ser Ile Asn Gly
            270                 275                 280

Gly Gln Glu Val Arg Arg Thr Ala Glu
            285                 290
```

<210> SEQ ID NO 18
<211> LENGTH: 3341
<212> TYPE: DNA
<213> ORGANISM: Glycine max

<400> SEQUENCE: 18

| | | | | | |
|---|---|---|---|---|---|
| tcaatgtcag | aatgatactg | acagatctaa | tttcggttaa | tttgattact | aattagtagg | 60 |
| tgccagtggc | ataaattgaa | taagaaataa | aaataattca | ttatcaattc | aaatgaagga | 120 |
| aaaatatatt | gtgtcaaaag | gatattaatt | atcaagattc | aaaggaaaaa | atagtatact | 180 |
| cttttttata | aatacactac | tgagtaattt | aaccaaattt | aaattataat | tttaatgctc | 240 |
| agtttacttc | aatggctata | ccttttttt | atatattcaa | tggctatacc | tataaattgt | 300 |
| aatattcaag | cattgtttta | atggaagcaa | acaaggcatc | acatatggct | aggaagaatt | 360 |
| gaacaaaaac | aaattagcta | catacattaa | gctcttaata | ttataaaaac | atgccgatga | 420 |
| tatatgtcca | tagatttcaa | gggagctaat | accggaaagt | gtcaaggatt | tatactttac | 480 |
| agctaaagtt | tcagtctcaa | agaaaatgat | gacactgtat | cattgagcag | acacaatgag | 540 |
| ttacatcaca | aaaccagcct | gtagggatac | atgactcata | ttccttgtca | aatatcgctg | 600 |
| cctcaatgtg | catagcgatt | atagtaatgg | attcacagta | aaggagcagg | taagccaatt | 660 |
| ttttattctt | aaattccctg | ttgagactac | attatatttt | tgaattgcga | gatattcaag | 720 |
| gattacttgt | tatatatgtt | aagccgccgc | atactgttta | agtattaat | gatatatcat | 780 |
| tgttactata | aaatattttt | acacaatgca | aggtaaatat | ttctattaca | tgttgacata | 840 |
| aaaatatctt | acgtaaacta | aactaaactc | ttgtttaaaa | tggtactagt | atctatacaa | 900 |
| cgagattaaa | gctacaaaaa | tatgatacaa | agagggagat | tttgtatagt | atcctatgct | 960 |
| tgaagaacgt | atcaacatcc | agtatctcga | aaattcagta | ctaaaatgta | aaatctattg | 1020 |
| atgtgtactg | aaggattcag | aaattcaact | attttgaact | cgctgtatat | taatttgtcc | 1080 |
| atataaggtc | acagcagcca | actaatcatt | tttttattag | agactagata | caattattac | 1140 |
| atgcaaatgg | ataataaagt | agcatgtagc | atcaccttat | cgcacatgtt | agttagctgc | 1200 |
| atggaccatc | tgtatgattt | gtgatgtgtc | ttgtagctta | acttaagcac | tatatatcac | 1260 |
| tgatcagtgt | tgtggaaaca | gcgaagagaa | atgaaattgc | ctctttcaag | aagcatctga | 1320 |
| gtgtttacta | ttttgtacta | tatttatata | tagtcactca | agcttctagg | atttctgcct | 1380 |

```
gctgcatcaa aatgggaagc aacttgaggt ttttgagtct ttgcctcttg gcattgattg    1440
catcaactca tgctcaactt cagcttggtt tttatgctaa cagttgccca aaagcagagc    1500
aaattgtttt gaaatttgtt catgaccata tccacaatgc tccatcacta gcagctgcat    1560
taataagaat gcacttccat gactgttttg taagggtatg tggttcaagc ctataatttt    1620
ctttcatttt ttacttaaca agtaccatat atgttagatt aaagaactaa ctaagatgaa    1680
gtatttcagg gatgtgatgc atcagtcctt ctgaactcaa caaccaatca ggctgagaag    1740
aatgctcctc caaatctcac agtaagaggc tttgacttca ttgacagaat aaagagcctt    1800
gttgaagctg aatgccctgg tgtggtctct tgtgctgata tcctcacttt ggctgccaga    1860
gacactattg tagccacagt aagtactcaa ttgctatcag gaaaatctta agagtataag    1920
cacaacttct gcttcacctt tatatcttta cacttctttt tgagaacaag atgacccatt    1980
tgctggttta tgccattact gacattggtg ttcagggtgg accttttttgg aaagttccaa    2040 ctggtcgaag ggatggggtc gtctctaact tgacggaagc cagaaataac attcctgctc    2100
cattttccaa cttcaccacc ctacagacac tctttgctaa ccaaggactt gatttgaagg    2160
acttggtcct gctctctggt atcatttatg aaacaaatcc taagcattat tgttgaaaga    2220
ctaacacgtt tttgagtccc tcatggtaac gccaggtttc cagtcacgac gttgtaaaac    2280
gacggccagt gagcgcgcag taatacgact cactataggc gaattggagc tccagcggtg    2340
gcggccgctc tagaactagt ggatccccccg ggctgcaggt tttcgatatc aagcttatcg    2400
ataccgtcga cacctcgagt tggaaatatg tctaaatatc tgcaatttca acatgaataa    2460 tttattttt aggaatttat taactacatt ttaaatttc aggatattga tttgataatt    2520
cttattattt agactttagg acactatcag tttgtttaat ttcaaggtta agatgtgtta    2580 tatttgaat tttgcattac attatttcat tttaaaaaat aaaaccaaca aattggcatg    2640
aattatacat tgttcttggg cttgtaatga gcaagagttc aaattgtttc aggtgctcac    2700
acaattggta tcgctcattg ctcatcatta tcaaaccggt tgttcaattt cactggcaag    2760
ggtgatcaag acccgtcact agatagtgaa tatgctgcaa atttgaaagc attcaagtgc    2820
acagacctca acaagttgaa caccacaaaa attgagatgg accctggaag tcgcaagaca    2880
tttgatctta gctactatag tcacgttatt aagagaaggg gtctatttga gtcagatgct    2940
gcattattga ctaactcagt tacaaaggca caaatcatcc aattgcttga agggtcagtt    3000
gaaaatttct ttgctgagtt tgcaacctcc atcgagaaaa tgggaagaat taatgtgaag    3060
acagggacag aaggagagat caggaagcat tgtgcattta taaatagcta agaatcttgt    3120
cttgttcatg gatgaatctt gtatcattta tttttggg tttgattatt tatgctatgc    3180 catgttttt gattagttat gctatgccat gtggtctctg tctacatacg tgtgatcctt    3240
tatggtatgg ttgttgtatg tgtgttggaa taagtgggct cttaagttat tcatatttcc    3300
aactttgctg gtagatcatg ctcttgtaat aagaaccaga a                       3341
```

<210> SEQ ID NO 19
<211> LENGTH: 2404
<212> TYPE: DNA
<213> ORGANISM: Glycine max

<400> SEQUENCE: 19

```
caataattat agtttgatag cctgctacca tcaaggattg caatgcaagc tttggcacca      60
aaaacaaaat tacgatggct caacctcaac cttaactacc gcatacattg gtataactca     120
```

-continued

```
ggcgcagttt ggtttgctag tgaaaccact agtgatttgg ttagtgctga tcagactttg      180
agtgactttt ttatgtcgtg ccatttcaa ttaaatgtct aaaaatttta agataattaa      240
acaacttttt tattttaaa aagctaaaac acaaaaagaa atgagtactt ttcttgtaaa      300
ttgacaataa tggttttttt tataaaaaaa aaataagtg tcttacaaaa gaaaattatc      360
caaacataac actaatatgg catggacaat tggccacgag gctgttggcc tcaatttccg      420
ttgaaaagcc taaactgaaa tatggcaaga gtttgatcac agaaaaaaat ggtcggggta      480
aaatcaaact ttcacttatt acattaggac aataggagaa agaccaagga taatgtcata      540
atcaacgaat cataattatg tatcatgggg tggaggatga catcgtgatt tgtgatatta      600
ccaactactc ttgaagagtt tagaccatga aactatagct taagactgga tttagcatga      660
atatgtaatt aaattattct ggatcgagag taacatacca ataaaaaaaa aagaagagga      720
acatcacaag ccacagaaag ctaccggagg cttaaaaagt ttaaggttca ttaggacgga      780
gcataaagtg gattgtcttt tagtaatgag aatgcttcaa cattactact cttgattgac      840
agtacttctt aacgaattga tttctagggc cacattatct caaacaataa ttgatctctt      900
ttatatctat aaaaattcat tttccccatc tttgatttcc acggctaaaa gctaaatatc      960
atcaaagtac tcaaattagc atggctgtca tggttgcatt cttgaatttg atcatcatgt     1020
tttcagtagt ctctacaaca ggcaagtcac tgagcttaaa ctactatgca aaaacatgcc     1080
ctaatgtgga gttcattgtt gccaaggcag taaaggatgc cactgctagg aaaaaactgt     1140
tccagcagca attctgcgaa tgcacttcca tgattgtttc gttcgggtaa tgctattttg     1200 accctcctc cctcctttcc tcttgaccgt tccgcctcat tgatgcatc atgaaatcaa     1260 atcatattgt tttcttttt cctatactct tgaaggggtg tgatgcctct gtgctgctaa     1320
attcaaaagg aaacaacaaa gcagaaaaag acgggccacc aaatgtttct ttgcatgcat     1380
tctatgtcat tgatgcagca aagaaagcac tagaagcttc atgccctggt gtggtctctt     1440
gtgctgacat ctctgctctg gcagcaaggg tcgcagtttt tctggtaaga aaactttgaa     1500
aagtaccaaa tttctcatca ttcagatcct aaactaaaca atcattatgt cttcgagaat     1560
tgacaaatgc agctaaggtg gcttgtattt ggaagtcttg actaattgta taaatatat     1620 tctgcagtca ggaggaccta catgggatgt tcctaaagga agaaaggatg gtagaacatc     1680
taaagccagt gaaaccagac aattgccagc accaaccttc aacttatcac aactgcggca     1740
aagtttctct caaagaggac tgtcagggga agacctggta gctctgtcag gtaagctatt     1800
cctaaagtca aaactgccaa aacttgacca ttttcattt attccaattt atatctgaat     1860
agagtttaga gtttctcctt tgactcatat gtaggggggc cactttggg tttctctcac     1920 tgctcatctt tcaagaacag aatccacaac ttcaatgcaa cacatgatgt tgacccttca     1980
ttaaatccat catttgcagc aaaactgatc tcaatttgtc cactaaaaaa tcaggcaaaa     2040
aatgcaggca cctctatgga cccttcaaca acaacttttg ataatacata ttacaggttg     2100
atcctccaac agaaaggctt gttttcttct gatcaagttt tgcttgacaa cccagacact     2160
aaaaatctgg ttacaaagtt tgccacctca aaaaaggctt tttatgaggc ttttgcgaag     2220
tccatgatca gaatgagtag ctacaatggt ggacaggagg ttagaaggac tgctgaatga     2280
tcaattaata agtcttaaat caattcaagt taaattgatg ttccaaacaa gttggatcaa     2340
atttcctaga tgccaagaat attatgtctt tttcctctat taaagaaata tgtatattta     2400
tctg                                                                  2404
```

<210> SEQ ID NO 20
<211> LENGTH: 4655
<212> TYPE: DNA
<213> ORGANISM: Glycine max

<400> SEQUENCE: 20

| | | | | | |
|---|---|---|---|---|---|
| tagataaaaa | aatgggatat | aattttttctc | agatgttgtt | tatactgttt | ttttaatcag | 60 |
| aattaaaatt | aatctttaat | tatcgacata | attttttttg | gtgaatatta | tcgacataat | 120 |
| tatttaatac | aaattttttat | tgtacataga | agtgatactt | caattttaat | attggagaac | 180 |
| agtacgaaaa | cataaaaaaa | ctgttattag | aagaaaaaaa | tatatggaaa | aggttagcta | 240 |
| catatattag | ctaaattagt | tgttctaatt | ggctatataa | accctattgt | actctttgta | 300 |
| atctcaccctt | tttcatttaa | atacatttct | acttttttaag | ttctatattt | tctctcaatt | 360 |
| ttcttcgata | aaccatgaaa | tttaacatgg | tatatcagcg | ataccaccca | ctttgaaagc | 420 |
| catgtatggc | tagtatgggc | agccaaaatt | tgccctggtt | caagcaaagc | aagtgtttat | 480 |
| atagatgtga | cttttgttga | ggaactcatg | ccaatggtac | tgattgtgaa | actgagaaaa | 540 |
| ctaatttgga | gaatttgaat | tatgatcatt | aaatactcct | ctcctgacta | ccttcgtccc | 600 |
| tcaaatttgt | accatcatta | tttcccaaaa | atttgattac | aatgcactaa | ttaatgaatg | 660 |
| tttcttacat | tatcatatta | tcatatctga | cattttgttt | ttactttttta | taataattat | 720 |
| tttaaaaagt | catacatgca | aataattttt | taatagttta | cagttaaatt | tttacagtaa | 780 |
| aaatgcatga | aaattaaact | ttatttttcc | aagtcatcat | ttagtcaaat | cccaaaacaa | 840 |
| tgattatttt | ttgcaaatga | atgtttattg | aacatttaaa | tgtagcctaa | ttaattctgg | 900 |
| ttatggtgtc | aatgttccaa | aacctaatgc | aagatcttag | caagtacata | catagatcta | 960 |
| attttaaact | tatctttacg | caagagatat | aaagattata | catctagttt | taaacattaa | 1020 |
| cttttgtttt | tgtgttaaaa | aacagtaaca | ttttcttaat | tttgtagagt | gacgtgctcc | 1080 |
| aaccatatta | acgaagattt | taattggtat | tcaagttcat | gaacttagta | aataagtttt | 1140 |
| ggtcttcagt | tttcaatttt | cattacaaca | tttatgtaaa | atatcaacgt | tttctgaaat | 1200 |
| ttgttgcttg | tgtgctccaa | ccacatttaa | gagattatag | aaattaattt | tcaagaagat | 1260 |
| aagattccta | ctcttgcctg | gccctaccat | agtacaataa | atccactcat | aaatcaacaa | 1320 |
| gtcgtcgtca | taggcaattg | ggcatcatat | cataaacaat | acgtacgtga | tattatctag | 1380 |
| tgtctctcag | tttactttat | gagaaattat | ttttctttaa | aaaagttaa | ttaataaaaa | 1440 |
| catttgcgat | accgtgagtt | acaagaaatc | cgccgaattc | atctctataa | ataaaaggat | 1500 |
| ctatatgaga | ggtaaaatca | tattaactca | aaatgggttc | catgcgtcta | ttagtagtgg | 1560 |
| cattgttgtg | tgcatttgct | atgcatgcag | gttttttcagt | ctcttatgct | cagcttactc | 1620 |
| ctacgttcta | cagagaaaca | tgtccaaatc | tgttccctat | tgtgtttgga | gtaatcttcg | 1680 |
| atgcttcttt | caccgatccc | cgaatcgggg | ccagtctcat | gaggcttcat | tttcatgatt | 1740 |
| gctttgttca | agtacgtact | tttttttttc | cttccaaaat | gccctgcata | tttaacaaga | 1800 |
| ttgctttgtt | cacctagaaa | aatgtgtttt | tttcaacgat | cttacgtacg | tttgtttggt | 1860 |
| ttgaaaaata | aatcagaaag | agatcaagaa | aatagctaga | agaaagcaa | cgttttttta | 1920 |
| aaaggtattt | agtgtgagaa | aaatattaaa | actgaagaga | agaaattaa | ataagctttt | 1980 |
| cttgaatgat | atttacatgt | cttattaact | taaagtcacc | ttttttcttt | aagttgtgct | 2040 |
| tgaagaaaaa | agatgtctttt | cagtttagtt | ttgattaatg | ctaattatat | ttttaattaa | 2100 |
| ttaattaata | ctatatatct | atttaccata | ttaattatta | ctatatttca | tgatgacaac | 2160 |

```
agacaagtat tctaaagagg tatcggtaga tgattaattt ttttataaaa aaatcttttg   2220
cgtgtataga tattctttta taattggtgc agaaacttgt aatgctaatt gcaattaatc   2280
ttacattgat taactaatag ctataatcaa tatttaggtt aggtatagga gacaaatcaa   2340
gtgatctgaa caaattaagt tgttatattt gcattgtgac agggttgtga tggatcagtt   2400
ttgctgaaca acactgatac aatagaaagc gagcaagatg cacttccaaa tatcaactca   2460
ataagaggat tggacgttgt caatgacatc aagacagcgg tggaaaatag ttgtccagac   2520
acagtttctt gtgctgatat tcttgctatt gcagctgaaa tagcttctgt tctggtaatt   2580
aataactcct aattaattcc caaccattaa aaagttgcat gattggattc aaaattctat   2640
ggtattgggg ttctgatata aatttgtaat taaattgcac taaaaaaaat tatcatatac   2700
ttttaataaa aaaaatttat ctaatttaat ttattattaa aactatttt aaaattcaat   2760 cctaactctt ttttaatcgg agcatgtaag ctggcaccca ccgtatatcg ttggaagatg   2820
ctataaaacc atttaattaa tggatggaat cagtcaaaac atttaattca aaatactctt   2880
aattgtgatt agtaatcatg ttcgggcaag ttacgttgtg tataattaat ttgacttaat   2940
cagataaaaa aacaaatgga cgcaagccgg ttggtataga tatcactggc ctgtagaata   3000
tgtggttttt cacgtttaaa taaaagctag ctactatatt atatttagtc ttttttttc   3060 ttaaacccat ttaacgtgat ttattgactg tgaaacatgt ttccacacac aggcttagaa   3120
actcctcgca actaacatct ccaaaatttg actatttatt tatgaagata attcatctat   3180
gatgttcaac tctattatat atatgtatca tcgcagtatt aagaattata atagtcaaat   3240
atagaagtat atcgggtaaa tgtagttgca tgtgcgacct gtttcgtgta aaatgcttat   3300
tctatatagc tttttttatt ggaaaataac gatgaactaa aaacgaaagg gtatcatata   3360
gtttgacttt tatgttagag agagacatct taatttggtc atatgttaaa taattaatta   3420
caatgcatac acaaatattt atgccatatc taaaaaatga taaaatatca taggtatact   3480
caactatatg atatccccat aacagaaatt gtacttttct tcaggcaatg aacttaacat   3540
ttctgtttgc taaaaacaaa catccactta aagtggttca acatatttat gtaataattt   3600
acagggagga ggtccaggat ggccagttcc attaggaaga agggacagct taacagcaaa   3660
ccgaacccct gcaaatcaaa accttccagc acctttcttc aacctcactc aacttaaagc   3720 ttccttttgct gttcaaggtc tcaacaccct tgatttagtt acactctcag gtatacataa   3780 tcaattttttt atttgctatt agctagcaat aaaaagtctc tgatacagac atatttagat   3840
aaattaattt ctccataaac atttataata aaattatcaa tttatgtact taaaaattat   3900
ggattgaagc tcttttcatc caacttttac taaagttaag gtgcatataa tataaaataa   3960
actatctctt gtttcttata aaagattga agataagtta aagtctactt ataaatcatt   4020
aatatatgta taggtggtca tacgtttgga agagctcggt gcagtacatt cataaaccga   4080
ttatacaact tcagcaacac tggaaaccct gatccaactc tgaacacaac atacttagaa   4140
gtattgcgtg caagatgccc ccagaatgca actgggggata acctcaccaa tttggacctg   4200
agcacacctg atcaatttga caacagatac tactccaatc ttctgcagct caatggctta   4260
cttcagagtg accaagaact tttctccact cctggtgctg ataccattcc cattgtcaat   4320
agcttcagca gtaaccagaa tactttcttt tccaacttta gagtttcaat gataaaaatg   4380
ggtaatattg gagtgctgac tgggggatgaa ggagaaattc gcttgcaatg taattttgtg   4440
aatggagact cgtttggatt agctagtgtg gcgtccaaag atgctaaaca aaagcttgtt   4500
gctcaatcta aataaaccaa taattaatgg ggatgtgcat gctagctagc atgtaaaggc   4560
```

-continued

```
aaattaggtt gtaaacctct ttgctagcta tattgaaata aaccaaagga gtagtgtgca    4620
tgtcaattcg attttgccat gtacctcttg gaata                               4655

<210> SEQ ID NO 21
<211> LENGTH: 1056
<212> TYPE: DNA
<213> ORGANISM: Glycine max
<220> FEATURE:
<221> NAME/KEY: CDS
<222> LOCATION: (1)..(1056)

<400> SEQUENCE: 21 atg ggt tcc atg cgt cta tta gta gtg gca ttg ttg tgt gca ttt gct       48
Met Gly Ser Met Arg Leu Leu Val Val Ala Leu Leu Cys Ala Phe Ala
 1               5                  10                  15 atg cat gca ggt ttt tca gtc tct tat gct cag ctt act cct acg ttc       96
Met His Ala Gly Phe Ser Val Ser Tyr Ala Gln Leu Thr Pro Thr Phe
             20                  25                  30 tac aga gaa aca tgt cca aat ctg ttc cct att gtg ttt gga gta atc      144
Tyr Arg Glu Thr Cys Pro Asn Leu Phe Pro Ile Val Phe Gly Val Ile
         35                  40                  45 ttc gat gct tct ttc acc gat ccc cga atc ggg gcc agt ctc atg agg      192
Phe Asp Ala Ser Phe Thr Asp Pro Arg Ile Gly Ala Ser Leu Met Arg
     50                  55                  60 ctt cat ttt cat gat tgc ttt gtt caa ggt tgt gat gga tca gtt ttg      240
Leu His Phe His Asp Cys Phe Val Gln Gly Cys Asp Gly Ser Val Leu
 65                  70                  75                  80 ctg aac aac act gat aca ata gaa agc gag caa gat gca ctt cca aat      288
Leu Asn Asn Thr Asp Thr Ile Glu Ser Glu Gln Asp Ala Leu Pro Asn
                 85                  90                  95 atc aac tca ata aga gga ttg gac gtt gtc aat gac atc aag aca gcg      336
Ile Asn Ser Ile Arg Gly Leu Asp Val Val Asn Asp Ile Lys Thr Ala
            100                 105                 110 gtg gaa aat agt tgt cca gac aca gtt tct tgt gct gat att ctt gct      384
Val Glu Asn Ser Cys Pro Asp Thr Val Ser Cys Ala Asp Ile Leu Ala
        115                 120                 125 att gca gct gaa ata gct tct gtt ctg gga gga ggt cca gga tgg cca      432
Ile Ala Ala Glu Ile Ala Ser Val Leu Gly Gly Gly Pro Gly Trp Pro
    130                 135                 140 gtt cca tta gga aga agg gac agc tta aca gca aac cga acc ctt gca      480
Val Pro Leu Gly Arg Arg Asp Ser Leu Thr Ala Asn Arg Thr Leu Ala
145                 150                 155                 160 aat caa aac ctt cca gca cct ttc ttc aac ctc act caa ctt aaa gct      528
Asn Gln Asn Leu Pro Ala Pro Phe Phe Asn Leu Thr Gln Leu Lys Ala
                165                 170                 175 tcc ttt gct gtt caa ggt ctc aac acc ctt gat tta gtt aca ctc tca      576
Ser Phe Ala Val Gln Gly Leu Asn Thr Leu Asp Leu Val Thr Leu Ser
            180                 185                 190 ggt ggt cat acg ttt gga aga gct cgg tgc agt aca ttc ata aac cga      624
Gly Gly His Thr Phe Gly Arg Ala Arg Cys Ser Thr Phe Ile Asn Arg
        195                 200                 205 tta tac aac ttc agc aac act gga aac cct gat cca act ctg aac aca      672
Leu Tyr Asn Phe Ser Asn Thr Gly Asn Pro Asp Pro Thr Leu Asn Thr
    210                 215                 220 aca tac tta gaa gta ttg cgt gca aga tgc ccc cag aat gca act ggg      720
Thr Tyr Leu Glu Val Leu Arg Ala Arg Cys Pro Gln Asn Ala Thr Gly
225                 230                 235                 240 gat aac ctc acc aat ttg gac ctg agc aca cct gat caa ttt gac aac      768
Asp Asn Leu Thr Asn Leu Asp Leu Ser Thr Pro Asp Gln Phe Asp Asn
                245                 250                 255
```

```
aga tac tac tcc aat ctt ctg cag ctc aat ggc tta ctt cag agt gac      816
Arg Tyr Tyr Ser Asn Leu Leu Gln Leu Asn Gly Leu Leu Gln Ser Asp
            260                 265                 270 caa gaa ctt ttc tcc act cct ggt gct gat acc att ccc att gtc aat      864
Gln Glu Leu Phe Ser Thr Pro Gly Ala Asp Thr Ile Pro Ile Val Asn
            275                 280                 285 agc ttc agc agt aac cag aat act ttc ttt tcc aac ttt aga gtt tca      912
Ser Phe Ser Ser Asn Gln Asn Thr Phe Phe Ser Asn Phe Arg Val Ser
290                 295                 300 atg ata aaa atg ggt aat att gga gtg ctg act ggg gat gaa gga gaa      960
Met Ile Lys Met Gly Asn Ile Gly Val Leu Thr Gly Asp Glu Gly Glu
305                 310                 315                 320 att cgc ttg caa tgt aat ttt gtg aat gga gac tcg ttt gga tta gct     1008
Ile Arg Leu Gln Cys Asn Phe Val Asn Gly Asp Ser Phe Gly Leu Ala
                325                 330                 335 agt gtg gcg tcc aaa gat gct aaa caa aag ctt gtt gct caa tct aaa     1056
Ser Val Ala Ser Lys Asp Ala Lys Gln Lys Leu Val Ala Gln Ser Lys
            340                 345                 350

<210> SEQ ID NO 22
<211> LENGTH: 352
<212> TYPE: PRT
<213> ORGANISM: Glycine max

<400> SEQUENCE: 22

Met Gly Ser Met Arg Leu Leu Val Val Ala Leu Leu Cys Ala Phe Ala
1               5                   10                  15

Met His Ala Gly Phe Ser Val Ser Tyr Ala Gln Leu Thr Pro Thr Phe
            20                  25                  30

Tyr Arg Glu Thr Cys Pro Asn Leu Phe Pro Ile Val Phe Gly Val Ile
        35                  40                  45

Phe Asp Ala Ser Phe Thr Asp Pro Arg Ile Gly Ala Ser Leu Met Arg
    50                  55                  60

Leu His Phe His Asp Cys Phe Val Gln Gly Cys Asp Gly Ser Val Leu
65                  70                  75                  80

Leu Asn Asn Thr Asp Thr Ile Glu Ser Glu Gln Asp Ala Leu Pro Asn
                85                  90                  95

Ile Asn Ser Ile Arg Gly Leu Asp Val Val Asn Asp Ile Lys Thr Ala
            100                 105                 110

Val Glu Asn Ser Cys Pro Asp Thr Val Ser Cys Ala Asp Ile Leu Ala
        115                 120                 125

Ile Ala Ala Glu Ile Ala Ser Val Leu Gly Gly Pro Gly Trp Pro
    130                 135                 140

Val Pro Leu Gly Arg Arg Asp Ser Leu Thr Ala Asn Arg Thr Leu Ala
145                 150                 155                 160

Asn Gln Asn Leu Pro Ala Pro Phe Phe Asn Leu Thr Gln Leu Lys Ala
                165                 170                 175

Ser Phe Ala Val Gln Gly Leu Asn Thr Leu Asp Leu Val Thr Leu Ser
            180                 185                 190

Gly Gly His Thr Phe Gly Arg Ala Arg Cys Ser Thr Phe Ile Asn Arg
        195                 200                 205

Leu Tyr Asn Phe Ser Asn Thr Gly Asn Pro Asp Pro Thr Leu Asn Thr
    210                 215                 220

Thr Tyr Leu Glu Val Leu Arg Ala Arg Cys Pro Gln Asn Ala Thr Gly
225                 230                 235                 240

Asp Asn Leu Thr Asn Leu Asp Leu Ser Thr Pro Asp Gln Phe Asp Asn
```

```
                   245                 250                 255
Arg Tyr Tyr Ser Asn Leu Leu Gln Leu Asn Gly Leu Leu Gln Ser Asp
            260                 265                 270

Gln Glu Leu Phe Ser Thr Pro Gly Ala Asp Thr Ile Pro Ile Val Asn
        275                 280                 285

Ser Phe Ser Ser Asn Gln Asn Thr Phe Phe Ser Asn Phe Arg Val Ser
    290                 295                 300

Met Ile Lys Met Gly Asn Ile Gly Val Leu Thr Gly Asp Glu Gly Glu
305                 310                 315                 320

Ile Arg Leu Gln Cys Asn Phe Val Asn Gly Asp Ser Phe Gly Leu Ala
                325                 330                 335

Ser Val Ala Ser Lys Asp Ala Lys Gln Lys Leu Val Ala Gln Ser Lys
            340                 345                 350

<210> SEQ ID NO 23
<211> LENGTH: 2419
<212> TYPE: DNA
<213> ORGANISM: Glycine max

<400> SEQUENCE: 23 cataattat agtttgatag cctgctacca tcaaggattg caatgcaagc tttggcacca       60
aaaacaaaat tacgatggct caacctcaac cttaactacc gcatacattg gtataactca     120
ggcgcagttt ggtttgctag tgaaaccact agtgatttgg ttagtgctga tcagactttg     180
agtgactttt ttatgtcgtg ccatttcaa ttaaatgtct aaaattta agataattaa        240 acaactttt tattttaaa aagctaaaac acaaaagaa atgagtactt ttcttgtaaa        300
ttgacaataa tggttttttt tataaaaaaa aaaataagtg tcttacaaaa gaaaattatc     360
caaacataac actaatatgg catggacaat tggccacgag gctgttggcc tcaatttccg     420
ttgaaaagcc taaactgaaa tatggcaaga gtttgatcac agaaaaaaat ggtcggggta     480
aaatcaaact ttcacttatt acattaggac aataggagaa agaccaagga taatgtcata     540
atcaacgaat cataattatg tatcatgggg tggaggatga catcgtgatt tgtgatatta     600
ccaactactc ttgaagagtt tagaccatga aactatagct taagactgga tttagcatga     660
atatgtaatt aaattattct ggatcgagag taacatacca ataaaaaaaa aagaagagga     720
acatcacaag ccacagaaag ctaccggagg cttaaaaagt ttaaggttca ttaggacgga     780
gcataaagtg gattgtcttt tagtaatgag aatgcttcaa cattactact cttgattgac     840
agtacttctt aacgaattga tttctagggc acattatct caaacaataa ttgatctctt     900
ttatatctat aaaaattcat ttttccccatc tttgatttcc acggctaaaa gctaaatatc    960
atcaaagtac tcaaattagc atggctgtca tggttgcatt cttgaatttg atcatcatgt    1020
tttcagtagt ctctacaaca ggcaagtcac tgagcttaaa ctactatgca aaaacatgcc    1080
ctaatgtgga gttcattgtt gccaaggcag taaaggatgc cactgctagg aaaaaaactg    1140
ttccagcagc aattctgcga atgcacttcc atgattgttt cgttcgggta atgctatttt    1200
gacccctcct ccctccttc ctcttgaccg ttccgcctca tttgatgcat catgaaatca    1260
aatcatattg ttttcttttt tcctatactc ttgaaggggt gtgatgcctc tgtgctgcta    1320
aattcaaaag gaaacaacaa agcagaaaaa gacgggccac caaatgtttc tttgcatgca    1380
ttctatgtca ttgtagcagc aaagaaagca ctagaagctt catgccctgg tgtggtctct    1440
tgtgctgaca tctctgctct ggcagcaagg gtcgcagttt ttctggtaag aaaactttga    1500
aaagtaccaa atttctcatc attcagatcc taaactaaac aatcattatg tcttcgagaa    1560
```

```
ttgacaaatg cagctaaggt ggcttgtatt tggaagtctt gactaattgt ataaaatata    1620
ttctgcagtc aggaggacct acatgggatg ttcctaaagg aagaaaggat ggtagaacat    1680
ctaaagccag tgaaaccaga caattgccag caccaacctt caacttatca caactgcggc    1740
aaagtttctc tcaaagagga ctgtcagggg aagacctggt agctctgtca ggtaagctat    1800
tcctaaagtc aaaactgcca aaacttgacc attttccatt tattccaatt tatatctgaa    1860
tagagtttag agtttctcct ttgactcata tgtaggggg cacactttgg gtttctctca    1920
ctgctcatct ttcaagaaca gaatccacaa cttcaatgca acacatgatg ttgacccttc    1980
attaaatcca tcatttgcag caaaactgat ctcaatttgt ccactaaaaa atcaggcaaa    2040
aaatgcaggc acctctatgg acccttcaac aacaacttt gataatacat attacaggtt    2100
gatcctccaa cagaaaggct tgttttcttc tgatcaagtt ttgcttgaca acccagacac    2160
taaaaatctg gttacaaagt ttgccacctc aaaaaaggct ttttatgagg cttttgcgaa    2220
gtccatgatc agaatgagta gctacaatgg tggacaggag gttagaagga ctgctgaatg    2280
atcaattaat aagtcttaaa tcaattcaag ttaaattgat gttccaaaca agttggatca    2340
aatttcctag atgccaagaa tattatgtct ttttcctcta ttaaagaaat atgtatattt    2400
atctgaagtt aataaaatc                                                 2419

<210> SEQ ID NO 24
<211> LENGTH: 4648
<212> TYPE: DNA
<213> ORGANISM: Glycine max

<400> SEQUENCE: 24
aaaatgggat ataatttttc tcagatgttg tttatactgt tttttaatc agaattaaaa      60 ttaatctttta attatcgaca taatttttt tggtgaatat tatcgacata attatttaat    120 acaattttt attgtacata gaagtgatac ttcaatttta atattggaga acagtacgaa    180
aacataaaaa aactgttatt agaagaaaaa atatatggaa aaaggttagc tacatatatt    240
agctaaatta gttgttctaa ttggctatat aaaccctatt gtactctttg taatctcacc    300
tttttcattt aaatacattt ctactttta agttctatat tttctctcaa ttttcttcga    360
taaaccatga aatttaacat ggtatatcag cgataccacc cactttgaaa gccatgtatg    420
gctagtatgg gcagccaaaa tttgccctgg ttcaagcaaa gcaagtgttt atatagatgt    480
gacttttgtt gaggaactca tgccaatggt actgattgtg aaactgagaa actaatttg    540 gagaatttga attatgatca ttaaatactc ctctcctgac taccttcgtc cctcaaattt    600
gtaccatcat tatttcccaa aaatttgatt acaatgcact aattaatgaa tgtttcttac    660
attatcatat tatcatatct gactttttgt ttttactttt tataataatt attttaaaaa    720
gtcatacatg caaataattt tttaatagtt tacagttaaa tttttacagt aaaaatgcat    780
gaaaattaaa ctttattttt ccaagtcatc atttagtcaa atcccaaaac aatgattatt    840
ttttgcaaat gaatgtttat tgaacattta aatgtagcct aattaattct ggttatggtg    900
tcaatgttcc aaaacctaat gcaagatctt agcaagtaca tacatagatc taattttaaa    960
cttatcttta cgcaagagat ataaagatta tacatcagt tttaaacatt aacttttgtt   1020
tttgtgttaa aaaacagtaa cattttctta attttgtaga gtgacgtgct ccaaccatat   1080
taacgaagat tttaattggt attcaagttc atgaactag taaataagtt ttggtcttca   1140
gttttcaatt ttcattacaa catttatgta aaatatcaac gttttctgaa atttgttgct   1200
```

```
                                    -continued
tgtgtgctcc aaccacattt aagagattat agaaattaat tttcaagaag ataagattcc    1260
tactcttgcc tggccctacc atagtacaat aaatccactc ataaatcaac aagtcgtcgt    1320
cataggcaat tgggcatcat atcataaaca atacgtacgt gatattatct agtgtctctc    1380
agtttacttt atgagaaatt attttctttt aaaaaagtt aattaataaa acatttgcg     1440 ataccgtgag ttacaagaaa tccgccgaat tcatctctat aaataaaagg atctatatga    1500
gaggtaaaat catattaact caaaatgggt tccatgcgtc tattagtagt ggcattgttg    1560
tgtgcatttg ctatgcatgc aggttttca gtctcttatg ctcagcttac tcctacgttc     1620
tacagagaaa catgtccaaa tctgttccct attgtgtttg gagtaatctt cgatgcttct    1680
ttcaccgatc cccgaatcgg ggccagtctc atgaggcttc attttcatga ttgctttgtt    1740
caagtacgta ctttttttt tccttccaaa atgccctgca tatttaacaa gattgctttg     1800
ttcacctaga aaatgtgtt tttttcaacg atcttacgta cgtttgtttg gtttgaaaaa     1860
taaatcagaa agagatcaag aaaatagcta gaaagaaagc aacgtttttt taaaaggtat    1920
ttagtgtgag aaaaatatta aaactgaaga gaaagaaatt aataagctt ttcttgaatg     1980 atatttacat gtcttattaa cttaaagtca cctttttct ttaagttgtg cttgaagaaa     2040
aaagatgtct ttcagtttag ttttgattaa tgctaattat attttaatt aattaattaa    2100 tactatatat ctatttacca tattaattat tactatattt catgatgaca acagacaagt    2160
attctaaaga ggtatcggta gatgattaat tttttataa aaaatcttt tgcgtgtata     2220 gatattcttt tataattggt gcagaaactt gtaatgctaa ttgcaattaa tcttacattg    2280
attaactaat agctataatc aatatttagg ttaggtatag gagacaaatc aagtgatctg    2340
aacaaattaa gttgttatat ttgcattgtg acagggttgt gatggatcag ttttgctgaa    2400
caacactgat acaatagaaa gcgagcaaga tgcacttcca aatatcaact caataagagg    2460
attggacgtt gtcaatgaca tcaagacagc ggtggaaaat agttgtccag acacagtttc    2520
ttgtgctgat attcttgcta ttgcagctga aatagcttct gttctggtaa ttaataactc    2580
ctaattaatt cccaaccatt aaaaagttgc atgattggat tcaaaattct atggtattgg    2640
ggttctgata taaatttgta attaaattgc actaaaaaaa attatcatat acttttaata    2700
aaaaaaattt atctaatttta atttattatt aaaactattt ttaaaattca atcctaactc    2760
ttttttaatc ggagcatgta agctggcacc caccgtatat cgttggaaga tgctataaaa    2820
ccatttaatt aatggatgga atcagtcaaa acatttaatt caaaatactc ttaattgtga    2880
ttagtaatca tgttcgggca agttacgttg tgtataatta atttgactta atcagataaa    2940
aaaacaaatg gacgcaagcc ggttggtata gatatcactg gcctgtagaa tatgtggttt    3000 ttcacgtttta aataaaagct agctactata ttatatttag tcttttttt tcttaaaccc    3060 atttaacgtg atttattgac tgtgaaacat gtttccacac acaggcttag aaactcctcg    3120
caactaacat ctccaaaatt tgactattta tttatgaaga taattcatct atgatgttca    3180
actctattat atatatgtat catcgcagta ttaagaatta aatagtcaa atatagaagt     3240 atatcgggta aatgtagttg catgtgcgac ctgtttcgtg taaaatgctt attctatata    3300
gcttttttta ttggaaaata acgatgaact aaaaacgaaa gggtatcata tagttttgact    3360 tttatgttag agagagacat cttaatttgg tcatatgtta aataattaat tacaatgcat    3420
acacaaatat ttatgccata tctaaaaaat gataaaatat cataggtata ctcaactata    3480
tgatatcccc ataacagaaa ttgtactttt cttcaggcaa tgaacttaac atttctgttt    3540
gctaaaaaca aacatccact taagtggtt caacatattt atgtaataat ttacagggag     3600
```

```
gaggtccagg atggccagtt ccattaggaa gaagggacag cttaacagca aaccgaaccc  3660
ttgcaaatca aaaccttcca gcacctttct tcaacctcac tcaacttaaa gcttcctttg  3720
ctgttcaagg tctcaacacc cttgatttag ttacactctc aggtatacat aatcaatttt  3780
ttatttgcta ttagctagca ataaaaagtc tctgatacag acatatttag ataaattaat  3840
ttctccataa acatttataa taaaattatc aatttatgta cttaaaaatt atggattgaa  3900 gctctttca tccaactttt actaaagtta aggtgcatat aatataaaat aaactatctc  3960
ttgtttctta taaaaagatt gaagataagt taaagtctac ttataaatca ttaatatatg  4020
tataggtggt catacgtttg gaagagctcg gtgcagtaca ttcataaacc gattatacaa  4080
cttcagcaac actggaaacc ctgatccaac tctgaacaca acatacttag aagtattgcg  4140
tgcaagatgc ccccagaatg caactgggga taacctcacc aatttggacc tgagcacacc  4200
tgatcaattt gacaacagat actactccaa tcttctgcag ctcaatggct tacttcagag  4260
tgaccaagaa cttttctcca ctcctggtgc tgataccatt cccattgtca atagcttcag  4320
cagtaaccag aatactttct tttccaactt tagagtttca atgataaaaa tgggtaatat  4380
tggagtgctg actggggatg aaggagaaat tcgcttgcaa tgtaattttg tgaatggaga  4440
gctcgtttgg attagctagt gtggcgtcca aagatgctaa acaaaagctt gttgctcaat  4500
ctaaataaac caataattaa tggggatgtg catgctagct agcatgtaaa ggcaaattag  4560
gttgtaaacc tctttgctag ctatattgaa ataaaccaaa ggagtagtgt gcatgtcaat  4620
tcgattttgc catgtacctc ttggaata                                    4648
```